US012347337B2

(12) United States Patent
Emerson et al.

(10) Patent No.: US 12,347,337 B2
(45) Date of Patent: Jul. 1, 2025

(54) ENHANCED TESTING AND CHARACTERIZATION TECHNIQUES FOR PHOTOTHERAPEUTIC LIGHT TREATMENTS

(71) Applicant: KNOW Bio, LLC, Durham, NC (US)

(72) Inventors: David T. Emerson, Durham, NC (US); Nathan Stasko, Chapel Hill, NC (US); Jacob Kocher, Durham, NC (US); Adam Cockrell, Durham, NC (US)

(73) Assignee: KNOW Bio, LLC, Morrisville, NC (US)

( * ) Notice: Subject to any disclaimer, the term of this patent is extended or adjusted under 35 U.S.C. 154(b) by 822 days.

(21) Appl. No.: 17/516,156

(22) Filed: Nov. 1, 2021

(65) Prior Publication Data

US 2022/0189342 A1 Jun. 16, 2022

Related U.S. Application Data

(60) Provisional application No. 63/123,631, filed on Dec. 10, 2020.

(51) Int. Cl.
*G09B 23/28* (2006.01)
*A61N 5/06* (2006.01)

(52) U.S. Cl.
CPC ............. *G09B 23/286* (2013.01); *A61N 5/06* (2013.01); *A61N 2005/0658* (2013.01)

(58) Field of Classification Search
CPC ............................... G09B 23/286; A61N 5/06; A61N 2005/0658; A61N 2005/0662; A61N 5/0613; A61N 5/0624

(Continued)

(56) References Cited

U.S. PATENT DOCUMENTS 1,244,819 A 10/1917 Young
2,884,926 A 5/1959 Grasso
(Continued)

FOREIGN PATENT DOCUMENTS

AU 2016100390 A4 7/2016
CN 101687101 A 3/2010
(Continued)

OTHER PUBLICATIONS

Technical Examination Report for Brazilian Patent Application No. 122020024964-1, mailed Nov. 29, 2022, 6 pages.
(Continued)

*Primary Examiner* — Robert P Bullington
*Assistant Examiner* — Stephen Alvesteffer
(74) *Attorney, Agent, or Firm* — Withrow & Terranova, P.L.L.C.

(57) ABSTRACT

Devices and methods for impinging light on tissue to induce one or more biological effects, and more particularly enhanced testing and characterization techniques for phototherapeutic light treatments are disclosed. Such testing and characterization techniques may be particularly useful in the evaluation and development of light-based treatments for various infectious diseases, including multiple variants of SARS-CoV-2. In particular aspects, testing and characterization techniques are related to the direct testing of differentiated tissue models of human airway epithelia that have been exposed to various pathogens. Phototherapeutic light treatments and corresponding treatment protocols for light are also described that not only inactivate SARS-COV-2 variants in cell-free suspensions, but also inhibit SARS-CoV-2 infections at multiple stages of infection in tissue models of human airway epithelia in a variant-agnostic manner.

21 Claims, 22 Drawing Sheets

(58) Field of Classification Search
USPC .......................................................... 434/262
See application file for complete search history.

(56) References Cited

U.S. PATENT DOCUMENTS

| | | | |
|---|---|---|---|
| 4,466,434 A | 8/1984 | Brownstein |
| 4,493,796 A | 1/1985 | Rinehart, Jr. |
| 4,736,745 A | 4/1988 | Gluckman |
| 5,074,295 A | 12/1991 | Willis |
| 5,228,431 A | 7/1993 | Giarretto |
| 5,282,462 A | 2/1994 | Kudo |
| 5,292,346 A | 3/1994 | Ceravolo |
| 5,541,822 A | 7/1996 | Bamber |
| 5,549,639 A | 8/1996 | Ross |
| 5,611,793 A | 3/1997 | Wilson et al. |
| 5,616,140 A | 4/1997 | Prescott |
| 5,634,711 A | 6/1997 | Kennedy et al. |
| 5,658,148 A | 8/1997 | Neuberger et al. |
| 5,683,436 A | 11/1997 | Mendes et al. |
| 6,026,828 A | 2/2000 | Altshuler |
| 6,045,499 A | 4/2000 | Pitesky |
| 6,096,066 A | 8/2000 | Chen et al. |
| 6,171,332 B1 | 1/2001 | Whitehurst |
| 6,201,764 B1 | 3/2001 | Rice et al. |
| 6,211,626 B1 | 4/2001 | Lys et al. |
| 6,244,865 B1 | 6/2001 | Nelson et al. |
| 6,251,127 B1 | 6/2001 | Biel |
| 6,283,956 B1 | 9/2001 | McDaniel |
| 6,290,496 B1 | 9/2001 | Azar et al. |
| 6,290,713 B1 | 9/2001 | Russell |
| 6,379,376 B1 | 4/2002 | Lubart |
| 6,443,978 B1 | 9/2002 | Zharov |
| 6,462,070 B1 | 10/2002 | Hasan et al. |
| 6,471,716 B1 | 10/2002 | Pecukonis |
| 6,491,618 B1 | 12/2002 | Ganz |
| 6,497,719 B2 | 12/2002 | Pearl et al. |
| 6,551,346 B2 | 4/2003 | Crossley |
| 6,561,808 B2 | 5/2003 | Neuberger |
| 6,623,513 B2 | 9/2003 | Biel |
| 6,645,230 B2 | 11/2003 | Whitehurst |
| 6,663,659 B2 | 12/2003 | McDaniel |
| 6,676,655 B2 | 1/2004 | McDaniel |
| 6,887,260 B1 | 5/2005 | McDaniel |
| 6,890,346 B2 | 5/2005 | Ganz et al. |
| 6,902,397 B2 | 6/2005 | Farrell et al. |
| 6,918,922 B2 | 7/2005 | Oron |
| 6,936,044 B2 | 8/2005 | McDaniel |
| 6,955,684 B2 | 10/2005 | Savage, Jr. et al. |
| 6,977,075 B2 | 12/2005 | Hasan et al. |
| 6,989,023 B2 | 1/2006 | Black |
| 7,090,497 B1 | 8/2006 | Harris |
| 7,107,996 B2 | 9/2006 | Ganz et al. |
| 7,144,248 B2 | 12/2006 | Irwin |
| 7,159,590 B2 | 1/2007 | Rife |
| 7,201,764 B2 | 4/2007 | Pearl et al. |
| 7,201,765 B2 | 4/2007 | McDaniel |
| 7,223,270 B2 | 5/2007 | Altshuler et al. |
| 7,223,281 B2 | 5/2007 | Altshuler et al. |
| 7,226,470 B2 | 6/2007 | Kemeny et al. |
| 7,267,673 B2 | 9/2007 | Pilcher et al. |
| 7,303,578 B2 | 12/2007 | De Taboada et al. |
| 7,304,201 B2 | 12/2007 | Holloway et al. |
| 7,309,348 B2 | 12/2007 | Streeter et al. |
| 7,329,273 B2 | 2/2008 | Altshuler et al. |
| 7,329,274 B2 | 2/2008 | Altshuler et al. |
| 7,422,598 B2 | 9/2008 | Altshuler et al. |
| 7,435,252 B2 | 10/2008 | Krespi et al. |
| 7,467,946 B2 | 12/2008 | Rizoiu et al. |
| 7,494,503 B2 | 2/2009 | McDaniel |
| 7,544,204 B2 | 6/2009 | Krespi et al. |
| D599,954 S | 9/2009 | Michaels et al. |
| 7,763,058 B2 | 7/2010 | Sterenborg et al. |
| D631,604 S | 1/2011 | Michaels et al. |
| 7,914,442 B1 | 3/2011 | Gazdzinski et al. |
| D635,686 S | 4/2011 | Tucker et al. |
| 7,918,229 B2 | 4/2011 | Cumbie et al. |
| 7,950,396 B2 | 5/2011 | Rose et al. |
| D639,751 S | 6/2011 | Tucker et al. |
| D640,793 S | 6/2011 | Britt |
| 8,021,148 B2 | 9/2011 | Goodson et al. |
| 8,021,405 B2 | 9/2011 | White |
| 8,025,686 B2 | 9/2011 | Morgan |
| 8,029,278 B1 | 10/2011 | Levine |
| 8,053,977 B2 | 11/2011 | Lifka et al. |
| 8,068,897 B1 | 11/2011 | Gazdzinski |
| 8,088,122 B2 | 1/2012 | Li et al. |
| 8,109,981 B2 | 2/2012 | Gertner et al. |
| 8,146,607 B2 | 4/2012 | Rabin et al. |
| 8,186,997 B2 | 5/2012 | Binner et al. |
| 8,192,473 B2 | 6/2012 | Tucker et al. |
| 8,214,958 B2 | 7/2012 | Pinyayev et al. |
| 8,240,312 B2 | 8/2012 | Feuerstein et al. |
| 8,252,033 B2 | 8/2012 | Tucker et al. |
| 8,398,264 B2 | 3/2013 | Anderson et al. |
| 8,435,273 B2 | 5/2013 | Lum et al. |
| 8,486,123 B2 | 7/2013 | Vizethum et al. |
| 8,518,029 B2 | 8/2013 | Birmingham et al. |
| 8,535,361 B2 | 9/2013 | Lim et al. |
| 8,556,951 B2 | 10/2013 | Witt et al. |
| 8,641,702 B2 | 2/2014 | Pilcher et al. |
| 8,651,111 B2 | 2/2014 | McDaniel |
| 8,668,727 B2 | 3/2014 | Natale et al. |
| 8,684,577 B2 | 4/2014 | Vayser |
| 8,685,466 B2 | 4/2014 | Piergallini et al. |
| 8,690,933 B2 | 4/2014 | Mitchell |
| 8,710,460 B2 | 4/2014 | Dayton |
| 8,721,696 B2 | 5/2014 | Krespi et al. |
| 8,747,446 B2 | 6/2014 | Chen et al. |
| 8,758,215 B2 | 6/2014 | Legendre et al. |
| 8,771,327 B2 | 7/2014 | Pearl et al. |
| 8,790,381 B2 | 7/2014 | Pierce |
| 8,815,931 B2 | 8/2014 | Grafe et al. |
| D712,561 S | 9/2014 | Hagenauer |
| 8,838,228 B2 | 9/2014 | Beisang, III et al. |
| 8,845,704 B2 | 9/2014 | Dunning et al. |
| D716,493 S | 10/2014 | Michaels et al. |
| 8,858,607 B1 | 10/2014 | Jones |
| 8,900,282 B2 | 12/2014 | Brawn |
| 8,900,283 B2 | 12/2014 | Johnson et al. |
| 8,940,775 B2 | 1/2015 | Fedele et al. |
| 9,017,391 B2 | 4/2015 | McDaniel |
| 9,039,966 B2 | 5/2015 | Anderson et al. |
| 9,040,103 B2 | 5/2015 | Marrot et al. |
| 9,095,704 B2 | 8/2015 | McGuire |
| 9,132,279 B2 | 9/2015 | Roersma et al. |
| 9,144,690 B2 | 9/2015 | McDaniel |
| 9,149,348 B2 | 10/2015 | Wu et al. |
| 9,162,001 B2 | 10/2015 | Sunkara et al. |
| 9,180,308 B1 | 11/2015 | Frost |
| 9,192,780 B2 | 11/2015 | McDaniel |
| 9,198,502 B2 | 12/2015 | Barnes et al. |
| 9,211,420 B2 | 12/2015 | Patel et al. |
| 9,215,921 B2 | 12/2015 | Thiebaut et al. |
| 9,227,082 B2 | 1/2016 | McDaniel |
| D754,897 S | 4/2016 | Michaels et al. |
| 9,308,389 B2 | 4/2016 | Brawn |
| 9,333,274 B2 | 5/2016 | Peterson et al. |
| 9,415,237 B2 | 8/2016 | Wagenaar Cacciola et al. |
| 9,439,989 B2 | 9/2016 | Lalicki et al. |
| 9,474,811 B2 | 10/2016 | Sharma |
| 9,504,752 B2 | 11/2016 | Kanno et al. |
| 9,504,847 B2 | 11/2016 | Pryor et al. |
| D777,339 S | 1/2017 | Chen |
| 9,545,524 B2 | 1/2017 | Maass et al. |
| 9,554,963 B2 | 1/2017 | Pilcher et al. |
| 9,561,077 B2 | 2/2017 | Alfano |
| 9,561,386 B2 | 2/2017 | Pearl et al. |
| 9,616,013 B2 | 4/2017 | Casasanta, III et al. |
| 9,636,522 B2 | 5/2017 | Oversluizen et al. |
| 9,700,641 B2 | 7/2017 | Hawkins et al. |
| 9,724,536 B1 | 8/2017 | Rabin et al. |
| 9,730,780 B2 | 8/2017 | Brawn et al. |
| 9,744,375 B2 | 8/2017 | Oberreiter et al. |
| D804,047 S | 11/2017 | Michaels et al. |

(56) References Cited

U.S. PATENT DOCUMENTS

| | | |
|---|---|---|
| 9,808,646 B2 | 11/2017 | Piergallini et al. |
| 9,808,647 B2 | 11/2017 | Rhodes et al. |
| 9,901,747 B2 | 2/2018 | Gamelin et al. |
| 9,907,976 B2 | 3/2018 | Bourke, Jr. et al. |
| 9,913,994 B2 | 3/2018 | Marchese et al. |
| 9,978,806 B1 | 5/2018 | Rapisarda |
| 10,010,718 B2 | 7/2018 | Basiony |
| 10,220,221 B2 | 3/2019 | Wu |
| 10,258,442 B2 | 4/2019 | Snyder et al. |
| 10,272,262 B2 | 4/2019 | Bourke, Jr. et al. |
| 10,328,276 B2 | 6/2019 | Williams et al. |
| 10,357,661 B2 | 7/2019 | Hellstrom et al. |
| 10,406,379 B2 | 9/2019 | Sentis et al. |
| 10,416,366 B2 | 9/2019 | Rose et al. |
| 10,463,873 B1 | 11/2019 | Yang et al. |
| 10,525,275 B2 | 1/2020 | Stasko et al. |
| 10,561,854 B2 | 2/2020 | Kim et al. |
| 10,569,097 B2 | 2/2020 | Medendorp, Jr. et al. |
| 10,639,498 B2 | 5/2020 | Enwemeka et al. |
| 10,682,203 B2 | 6/2020 | Vazales |
| 10,729,524 B2 | 8/2020 | Brawn et al. |
| 10,780,189 B2 | 9/2020 | Randers-Pehrson et al. |
| 10,981,017 B2 | 4/2021 | Enwemeka et al. |
| 11,058,888 B1 | 7/2021 | Steier et al. |
| 11,147,984 B2 | 10/2021 | Emerson et al. |
| 11,266,855 B2 | 3/2022 | Enwemeka et al. |
| 11,318,325 B2 | 5/2022 | Rezaie et al. |
| 2002/0029071 A1 | 3/2002 | Whitehurst |
| 2002/0128648 A1 | 9/2002 | Weber et al. |
| 2002/0135763 A1 | 9/2002 | MacKinnon et al. |
| 2002/0151941 A1 | 10/2002 | Okawa et al. |
| 2002/0173833 A1 | 11/2002 | Korman et al. |
| 2003/0009205 A1 | 1/2003 | Biel |
| 2003/0023284 A1 | 1/2003 | Gartstein et al. |
| 2003/0045778 A1 | 3/2003 | Ohline et al. |
| 2003/0076281 A1 | 4/2003 | Morgan et al. |
| 2003/0130709 A1 | 7/2003 | D.C. et al. |
| 2003/0153825 A1 | 8/2003 | Mooradian et al. |
| 2003/0167080 A1 | 9/2003 | Hart et al. |
| 2003/0233138 A1 | 12/2003 | Spooner |
| 2003/0236487 A1 | 12/2003 | Knowlton |
| 2004/0009459 A1* | 1/2004 | Anderson ............... G06T 19/00 703/11 |
| 2004/0032750 A1 | 2/2004 | Watts et al. |
| 2004/0039242 A1 | 2/2004 | Tolkoff et al. |
| 2004/0044384 A1 | 3/2004 | Leber et al. |
| 2004/0052798 A1 | 3/2004 | Neuberger |
| 2004/0073079 A1 | 4/2004 | Altshuler et al. |
| 2004/0073278 A1 | 4/2004 | Pachys |
| 2004/0162596 A1 | 8/2004 | Altshuler et al. |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2005/0024853 A1 | 2/2005 | Thomas-Benedict |
| 2005/0045189 A1 | 3/2005 | Jay |
| 2005/0055070 A1 | 3/2005 | Jones et al. |
| 2005/0059731 A1 | 3/2005 | Albrecht et al. |
| 2005/0064371 A1 | 3/2005 | Soukos et al. |
| 2005/0107853 A1 | 5/2005 | Krespi et al. |
| 2005/0231983 A1 | 10/2005 | Dahm |
| 2005/0256553 A1 | 11/2005 | Strisower |
| 2006/0019220 A1 | 1/2006 | Loebel et al. |
| 2006/0085052 A1 | 4/2006 | Feuerstein et al. |
| 2006/0093561 A1 | 5/2006 | Kennedy |
| 2006/0167531 A1 | 7/2006 | Gertner et al. |
| 2006/0183071 A1 | 8/2006 | Hsueh |
| 2006/0194164 A1 | 8/2006 | Altshuler et al. |
| 2006/0239921 A1 | 10/2006 | Mangat et al. |
| 2006/0258896 A1 | 11/2006 | Haber et al. |
| 2006/0287696 A1 | 12/2006 | Wright et al. |
| 2007/0038272 A1 | 2/2007 | Liu |
| 2007/0060819 A1 | 3/2007 | Altshuler et al. |
| 2007/0099154 A1 | 5/2007 | Johnson |
| 2007/0100254 A1 | 5/2007 | Murakami et al. |
| 2007/0105063 A1 | 5/2007 | Pinyayev et al. |
| 2007/0106856 A1 | 5/2007 | Nomura et al. |
| 2007/0135874 A1 | 6/2007 | Bala |
| 2007/0149868 A1 | 6/2007 | Blank et al. |
| 2007/0185553 A1 | 8/2007 | Kennedy |
| 2007/0198004 A1 | 8/2007 | Altshuler et al. |
| 2007/0208396 A1 | 9/2007 | Whatcott et al. |
| 2007/0213792 A1 | 9/2007 | Yaroslavsky et al. |
| 2007/0219600 A1 | 9/2007 | Gertner et al. |
| 2007/0233208 A1 | 10/2007 | Kurtz et al. |
| 2007/0259310 A1 | 11/2007 | Goodson et al. |
| 2007/0260231 A1 | 11/2007 | Rose et al. |
| 2007/0270650 A1 | 11/2007 | Eno et al. |
| 2008/0021370 A1 | 1/2008 | Bornstein |
| 2008/0032252 A1 | 2/2008 | Hayman et al. |
| 2008/0033516 A1 | 2/2008 | Altshuler et al. |
| 2008/0038685 A1 | 2/2008 | Sakaguchi et al. |
| 2008/0065175 A1 | 3/2008 | Redmond et al. |
| 2008/0096156 A1 | 4/2008 | Rose et al. |
| 2008/0097414 A1 | 4/2008 | Li et al. |
| 2008/0145813 A1 | 6/2008 | Crohn |
| 2008/0161748 A1 | 7/2008 | Tolkoff et al. |
| 2008/0210233 A1 | 9/2008 | McCarthy |
| 2008/0214530 A1 | 9/2008 | Colles |
| 2008/0245371 A1 | 10/2008 | Gruber |
| 2008/0254405 A1 | 10/2008 | Montgomery et al. |
| 2008/0269849 A1 | 10/2008 | Lewis |
| 2008/0280260 A1 | 11/2008 | Belikov et al. |
| 2008/0319430 A1 | 12/2008 | Zenzie et al. |
| 2009/0035725 A1 | 2/2009 | Loebel et al. |
| 2009/0093865 A1 | 4/2009 | Krespi et al. |
| 2009/0132011 A1 | 5/2009 | Altshuler et al. |
| 2009/0143842 A1 | 6/2009 | Cumbie et al. |
| 2009/0148808 A1 | 6/2009 | Alexander et al. |
| 2009/0254156 A1 | 10/2009 | Powell et al. |
| 2009/0318802 A1 | 12/2009 | Boyden et al. |
| 2009/0323370 A1 | 12/2009 | Koo |
| 2010/0004645 A1 | 1/2010 | Jeong et al. |
| 2010/0042040 A1 | 2/2010 | Arentz |
| 2010/0049180 A1 | 2/2010 | Wells et al. |
| 2010/0063565 A1 | 3/2010 | Beerwerth et al. |
| 2010/0076526 A1 | 3/2010 | Krespi et al. |
| 2010/0076529 A1 | 3/2010 | Tucker et al. |
| 2010/0081927 A1 | 4/2010 | Hyde et al. |
| 2010/0081928 A1 | 4/2010 | Hyde et al. |
| 2010/0100160 A1 | 4/2010 | Edman et al. |
| 2010/0106077 A1 | 4/2010 | Rabin et al. |
| 2010/0121131 A1 | 5/2010 | Mathes |
| 2010/0136646 A1 | 6/2010 | Tsen et al. |
| 2010/0160838 A1 | 6/2010 | Krespi |
| 2010/0185064 A1 | 7/2010 | Bandic et al. |
| 2010/0204762 A1 | 8/2010 | De Taboada et al. |
| 2010/0222852 A1 | 9/2010 | Vasily et al. |
| 2010/0239998 A1 | 9/2010 | Snyder et al. |
| 2010/0242155 A1 | 9/2010 | Carullo, Jr. |
| 2010/0286673 A1 | 11/2010 | Altshuler et al. |
| 2010/0331928 A1 | 12/2010 | Dunning et al. |
| 2011/0015707 A1 | 1/2011 | Tucker et al. |
| 2011/0020173 A1 | 1/2011 | Pryor et al. |
| 2011/0028798 A1 | 2/2011 | Hyde et al. |
| 2011/0028799 A1 | 2/2011 | Hyde et al. |
| 2011/0029038 A1 | 2/2011 | Hyde et al. |
| 2011/0029044 A1 | 2/2011 | Hyde et al. |
| 2011/0054573 A1 | 3/2011 | Mitchell |
| 2011/0054574 A1 | 3/2011 | Felix |
| 2011/0125229 A1 | 5/2011 | Lytle et al. |
| 2011/0144410 A1 | 6/2011 | Kennedy |
| 2011/0144727 A1 | 6/2011 | Benedict |
| 2011/0160814 A2 | 6/2011 | Tucker et al. |
| 2011/0162155 A1 | 7/2011 | Wai |
| 2011/0215261 A1 | 9/2011 | Lyslo et al. |
| 2011/0264174 A1 | 10/2011 | McNeill et al. |
| 2011/0301673 A1 | 12/2011 | Hoffer et al. |
| 2012/0045738 A1 | 2/2012 | Ho et al. |
| 2012/0059440 A1 | 3/2012 | Hamid |
| 2012/0065709 A1 | 3/2012 | Dunning et al. |
| 2012/0071710 A1 | 3/2012 | Gazdzinski |
| 2012/0088204 A1 | 4/2012 | Ho et al. |
| 2012/0096657 A1 | 4/2012 | So et al. |
| 2012/0126134 A1 | 5/2012 | Deal et al. |

(56) References Cited

U.S. PATENT DOCUMENTS

| | | |
|---|---|---|
| 2012/0191162 A1 | 7/2012 | Villa |
| 2012/0209359 A1 | 8/2012 | Chen et al. |
| 2012/0215292 A1 | 8/2012 | Gustavsson |
| 2012/0223216 A1 | 9/2012 | Flaherty et al. |
| 2012/0263625 A1 | 10/2012 | Aicher et al. |
| 2012/0270183 A1 | 10/2012 | Patel et al. |
| 2012/0310307 A1 | 12/2012 | Zhou |
| 2012/0322018 A1 | 12/2012 | Lowe et al. |
| 2013/0006119 A1 | 1/2013 | Pan et al. |
| 2013/0041432 A1 | 2/2013 | Tucker et al. |
| 2013/0053657 A1 | 2/2013 | Ziarno et al. |
| 2013/0089829 A1 | 4/2013 | Boutoussov et al. |
| 2013/0103120 A1 | 4/2013 | Salteri |
| 2013/0131762 A1 | 5/2013 | Oversluizen et al. |
| 2013/0144364 A1 | 6/2013 | Wagenaar Cacciola et al. |
| 2013/0158358 A1 | 6/2013 | Holland |
| 2013/0172959 A1 | 7/2013 | Azoulay |
| 2013/0196284 A1 | 8/2013 | Brawn |
| 2013/0197495 A1 | 8/2013 | Koifman et al. |
| 2013/0245417 A1 | 9/2013 | Spector |
| 2013/0280671 A1 | 10/2013 | Brawn et al. |
| 2014/0005758 A1 | 1/2014 | Ben-Yehuda et al. |
| 2014/0023983 A1 | 1/2014 | Lowe et al. |
| 2014/0067024 A1 | 3/2014 | Jones et al. |
| 2014/0094879 A1 | 4/2014 | Van Os et al. |
| 2014/0128941 A1 | 5/2014 | Williams |
| 2014/0128942 A1 | 5/2014 | Bembridge et al. |
| 2014/0148879 A1 | 5/2014 | Mersch |
| 2014/0163218 A1 | 6/2014 | Dei et al. |
| 2014/0171926 A1 | 6/2014 | Depfenhart |
| 2014/0194955 A1 | 7/2014 | Povolosky et al. |
| 2014/0243933 A1 | 8/2014 | Ginggen |
| 2014/0267662 A1 | 9/2014 | Lampo |
| 2014/0276247 A1 | 9/2014 | Hall et al. |
| 2014/0276248 A1 | 9/2014 | Hall et al. |
| 2014/0288351 A1 | 9/2014 | Jones |
| 2014/0296524 A1 | 10/2014 | Jones et al. |
| 2014/0303693 A1 | 10/2014 | Haarlander et al. |
| 2014/0323946 A1 | 10/2014 | Bourke, Jr. et al. |
| 2014/0350643 A1 | 11/2014 | Pepitone et al. |
| 2015/0005854 A1 | 1/2015 | Said |
| 2015/0030989 A1 | 1/2015 | Soukos et al. |
| 2015/0045720 A1 | 2/2015 | Kanno et al. |
| 2015/0112411 A1 | 4/2015 | Beckman et al. |
| 2015/0164618 A1 | 6/2015 | Heacock et al. |
| 2015/0217130 A1 | 8/2015 | Gross et al. |
| 2015/0265353 A1 | 9/2015 | Andrews et al. |
| 2015/0297914 A1 | 10/2015 | Hamid et al. |
| 2016/0000214 A1 | 1/2016 | Kim |
| 2016/0015840 A1 | 1/2016 | Gordon |
| 2016/0016001 A1 | 1/2016 | Loupis et al. |
| 2016/0039854 A1 | 2/2016 | McFarland |
| 2016/0051835 A1 | 2/2016 | Tapper et al. |
| 2016/0059031 A1 | 3/2016 | Wescott et al. |
| 2016/0106999 A1 | 4/2016 | Michaels et al. |
| 2016/0114185 A1 | 4/2016 | Mankin |
| 2016/0121108 A1 | 5/2016 | Kondo et al. |
| 2016/0129278 A1 | 5/2016 | Mayer |
| 2016/0151639 A1 | 6/2016 | Scharf et al. |
| 2016/0175609 A1 | 6/2016 | Dye et al. |
| 2016/0235983 A1 | 8/2016 | Berman et al. |
| 2016/0271415 A1 | 9/2016 | Min |
| 2016/0271420 A1 | 9/2016 | Pina |
| 2016/0317832 A1 | 11/2016 | Barneck et al. |
| 2016/0346564 A1 | 12/2016 | Burgmann |
| 2017/0027432 A1 | 2/2017 | Wachs |
| 2017/0028215 A1 | 2/2017 | Medendorp, Jr. et al. |
| 2017/0028216 A1 | 2/2017 | Medendorp, Jr. et al. |
| 2017/0165499 A1 | 6/2017 | Blanche et al. |
| 2017/0173358 A1 | 6/2017 | Demarest et al. |
| 2017/0203132 A1 | 7/2017 | Luttrull et al. |
| 2017/0224206 A1 | 8/2017 | Vayser |
| 2017/0225011 A1 | 8/2017 | Frost |
| 2017/0231490 A1 | 8/2017 | Toth et al. |
| 2017/0290648 A1 | 10/2017 | Kuo |
| 2017/0333728 A1 | 11/2017 | Sentis et al. |
| 2017/0340898 A1 | 11/2017 | Moor et al. |
| 2018/0008847 A1 | 1/2018 | Key |
| 2018/0014777 A1 | 1/2018 | Amir et al. |
| 2018/0036554 A1 | 2/2018 | Krespi |
| 2018/0111003 A1 | 4/2018 | Hewitson |
| 2018/0117355 A1 | 5/2018 | Loupis et al. |
| 2018/0125975 A1* | 5/2018 | Piergallini ............. A61K 47/08 |
| 2018/0146520 A1 | 5/2018 | Williams |
| 2018/0178027 A1 | 6/2018 | Shang |
| 2018/0256208 A1 | 9/2018 | Altschul et al. |
| 2018/0256916 A1 | 9/2018 | Kothari et al. |
| 2018/0264282 A1 | 9/2018 | Bornstein |
| 2018/0289940 A1 | 10/2018 | Spotnitz et al. |
| 2019/0014901 A1 | 1/2019 | Xi et al. |
| 2019/0030359 A1 | 1/2019 | Dijkstra et al. |
| 2019/0065970 A1 | 2/2019 | Bonutti et al. |
| 2019/0083809 A1 | 3/2019 | Zhang |
| 2019/0111255 A1 | 4/2019 | Errico et al. |
| 2019/0124888 A1 | 5/2019 | Coyle |
| 2019/0134419 A1 | 5/2019 | Bourke, Jr. et al. |
| 2019/0142516 A1 | 5/2019 | Boutoussov et al. |
| 2019/0175938 A1 | 6/2019 | Rezaie et al. |
| 2019/0201711 A1 | 7/2019 | Brawn et al. |
| 2019/0209857 A1 | 7/2019 | Brawn et al. |
| 2019/0335551 A1 | 10/2019 | Williams et al. |
| 2020/0101315 A1 | 4/2020 | Reinhardt |
| 2020/0114171 A1 | 4/2020 | Tortora |
| 2020/0155350 A1 | 5/2020 | Neev |
| 2020/0193597 A1 | 6/2020 | Fan et al. |
| 2020/0222714 A1 | 7/2020 | Stasko et al. |
| 2020/0261608 A1 | 8/2020 | Crosby et al. |
| 2020/0298014 A1 | 9/2020 | Stasko et al. |
| 2020/0298016 A1 | 9/2020 | Yoon et al. |
| 2020/0330186 A1 | 10/2020 | Barros et al. |
| 2020/0353112 A1* | 11/2020 | Randers-Pehrson ... A61B 90/80 |
| 2020/0360124 A1 | 11/2020 | Woo et al. |
| 2021/0008384 A1 | 1/2021 | Lee |
| 2021/0128935 A1 | 5/2021 | Stasko et al. |
| 2021/0128936 A1 | 5/2021 | Stasko et al. |
| 2021/0128937 A1 | 5/2021 | Stasko et al. |
| 2021/0128938 A1 | 5/2021 | Stasko et al. |
| 2021/0138259 A1 | 5/2021 | Stasko et al. |
| 2021/0138260 A1 | 5/2021 | Park et al. |
| 2021/0162125 A1 | 6/2021 | Altschul et al. |
| 2021/0196977 A1 | 7/2021 | Zhang |
| 2021/0205487 A1 | 7/2021 | Balme et al. |
| 2021/0228900 A1 | 7/2021 | Kothari et al. |
| 2021/0260398 A1 | 8/2021 | Bilston et al. |
| 2021/0267738 A1 | 9/2021 | Mackie |
| 2021/0283490 A1 | 9/2021 | Lin |
| 2021/0290970 A1 | 9/2021 | Hunter et al. |
| 2021/0290971 A1 | 9/2021 | Cockrell et al. |
| 2021/0290975 A1 | 9/2021 | Hunter et al. |
| 2021/0346500 A1 | 11/2021 | Schikora |
| 2021/0379400 A1 | 12/2021 | Emerson et al. |
| 2021/0402212 A1 | 12/2021 | Schupp et al. |
| 2022/0023660 A1 | 1/2022 | Emerson et al. |
| 2022/0040495 A1 | 2/2022 | Hwang et al. |
| 2022/0088409 A1 | 3/2022 | Dombrowski et al. |
| 2022/0168586 A1 | 6/2022 | Kothari et al. |
| 2022/0226667 A1 | 7/2022 | Kothari et al. |
| 2022/0240838 A1* | 8/2022 | Kohli ....................... F21V 9/02 |
| 2022/0262507 A1 | 8/2022 | Hagen et al. |
| 2023/0149735 A1 | 5/2023 | Miskin |
| 2023/0222654 A1 | 7/2023 | Fan et al. |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 102731405 A | 10/2012 |
| CN | 102802694 A | 11/2012 |
| CN | 103143015 A | 6/2013 |
| CN | 203169848 U | 9/2013 |
| CN | 103601727 A | 2/2014 |
| CN | 103610464 A | 3/2014 |
| CN | 103724356 A | 4/2014 |

(56) References Cited

FOREIGN PATENT DOCUMENTS

| | | |
|---|---|---|
| CN | 103930162 A | 7/2014 |
| CN | 104667432 A | 6/2015 |
| CN | 105664367 A | 6/2016 |
| CN | 108371756 A | 8/2018 |
| DE | 102010010763 A1 | 9/2011 |
| DE | 102013202122 A1 | 6/2014 |
| DE | 102012224183 A1 | 7/2014 |
| EP | 2368598 A1 | 9/2011 |
| EP | 2508229 A1 | 10/2012 |
| EP | 3069762 A1 | 9/2016 |
| EP | 3108931 A1 | 12/2016 |
| GB | 2499921 A | 9/2013 |
| KR | 20100124083 A | 11/2010 |
| KR | 20120090317 A | 8/2012 |
| KR | 101349157 B1 | 1/2014 |
| KR | 20140014689 A | 2/2014 |
| KR | 20190063041 A | 6/2019 |
| WO | 1995010243 A1 | 4/1995 |
| WO | 2004033040 A1 | 4/2004 |
| WO | 2004084752 A2 | 10/2004 |
| WO | 2006047868 A1 | 5/2006 |
| WO | 2006063318 A1 | 6/2006 |
| WO | 2006130340 A2 | 12/2006 |
| WO | 2008024414 A1 | 2/2008 |
| WO | 2008041296 A1 | 4/2008 |
| WO | 2008051918 A2 | 5/2008 |
| WO | 2008066943 A2 | 6/2008 |
| WO | 2008131343 A1 | 10/2008 |
| WO | 2008144157 A1 | 11/2008 |
| WO | 2009047669 A2 | 4/2009 |
| WO | 2010098761 A1 | 9/2010 |
| WO | 2011083378 A1 | 7/2011 |
| WO | 2011083381 A1 | 7/2011 |
| WO | 2012001194 A1 | 1/2012 |
| WO | 2013036558 A1 | 3/2013 |
| WO | 2014021557 A1 | 2/2014 |
| WO | 2014089552 A1 | 6/2014 |
| WO | 2014116659 A1 | 7/2014 |
| WO | 2014136255 A1 | 9/2014 |
| WO | 2014146029 A1 | 9/2014 |
| WO | 2015006309 A1 | 1/2015 |
| WO | 2015134204 A1 | 9/2015 |
| WO | 2016039812 A1 | 3/2016 |
| WO | 2016078603 A1 | 5/2016 |
| WO | 2016081594 A1 | 5/2016 |
| WO | 2016116859 A1 | 7/2016 |
| WO | 2016178472 A1 | 11/2016 |
| WO | 2017019836 A1 | 2/2017 |
| WO | 2017044931 A1 | 3/2017 |
| WO | 2017070155 A1 | 4/2017 |
| WO | 2018026892 A1 | 2/2018 |
| WO | 2019022275 A1 | 1/2019 |
| WO | 2019127427 A1 | 7/2019 |
| WO | 2019145519 A1 | 8/2019 |
| WO | 2019156921 A1 | 8/2019 |
| WO | 2019191820 A1 | 10/2019 |
| WO | 2019234308 A1 | 12/2019 |
| WO | 2020006048 A1 | 1/2020 |
| WO | 2020047659 A1 | 3/2020 |
| WO | 2020081910 A1 | 4/2020 |
| WO | 2021178655 A1 | 9/2021 |

OTHER PUBLICATIONS

Advisory Action and Examiner-Initiated Interview Summary for U.S. Appl. No. 17/410,154, mailed Jan. 10, 2023, 4 pages.
Notice of Allowance for U.S. Appl. No. 17/410,166, mailed Feb. 15, 2023, 8 pages.
Advisory Action for U.S. Appl. No. 17/162,259, mailed Jan. 9, 2023, 3 pages.
Final Office Action for U.S. Appl. No. 17/173,457, mailed Feb. 23, 2023, 9 pages.
Notice of Allowance and Examiner-Initiated Interview Summary for U.S. Appl. No. 17/201,120, mailed Jan. 19, 2023, 21 pages.
Author Unknown, "Visible spectrum," Wikipedia article, en.wikipedia.org/wiki/Visible_spectrum, accessed 2024, 11 pages.
Written Decision on Registration for Korean Patent Application No. 10-2022-7036254, mailed Mar. 20, 2024, 8 pages.
Advisory Action for U.S. Appl. No. 17/117,858, mailed Apr. 26, 2024, 3 pages.
Final Office Action for U.S. Appl. No. 17/148,090, mailed May 6, 2024, 9 pages.
Final Office Action for U.S. Appl. No. 17/201,061, mailed Mar. 11, 2024, 20 pages.
Notice of Allowance for Brazilian Patent Application No. BR112018001874-0, mailed Aug. 28, 2022, 6 pages.
Corrected Notice of Allowability for U.S. Appl. No. 16/709,550, mailed Sep. 21, 2022, 5 pages.
Non-Final Office Action for U.S. Appl. No. 17/148,124, mailed Oct. 13, 2022, 21 pages.
Final Office Action for U.S. Appl. No. 17/410,154, mailed Oct. 11, 2022, 20 pages.
Non-Final Office Action for U.S. Appl. No. 17/410,166, mailed Oct. 18, 2022, 11 pages.
Final Office Action for U.S. Appl. No. 17/162,259, mailed Oct. 19, 2022, 19 pages.
Non-Final Office Action for U.S. Appl. No. 17/162,283, mailed Nov. 8, 2022, 12 pages.
Non-Final Office Action for U.S. Appl. No. 17/173,457, mailed Oct. 17, 2022, 15 pages.
Notice of Allowance for U.S. Appl. No. 16/709,550, mailed Feb. 24, 2022, 8 pages.
Corrected Notice of Allowability for U.S. Appl. No. 16/709,550, mailed Mar. 25, 2022, 5 pages.
Corrected Notice of Allowability for U.S. Appl. No. 16/709,550, mailed Apr. 15, 2022, 5 pages.
Final Office Action for U.S. Appl. No. 16/898,385, mailed Feb. 15, 2022, 13 pages.
Advisory Action for U.S. Appl. No. 16/898,385, mailed Apr. 20, 2022, 4 pages.
Non-Final Office Action for U.S. Appl. No. 17/410,154, mailed Feb. 24, 2022, 21 pages.
Final Office Action for U.S. Appl. No. 17/410,154, mailed May 13, 2022, 18 pages.
Final Office Action for U.S. Appl. No. 17/410,166, mailed Mar. 14, 2022, 13 pages.
Advisory Action for U.S. Appl. No. 17/410,166, mailed May 11, 2022, 3 pages.
Non-Final Office Action for U.S. Appl. No. 17/201,120, mailed Apr. 15, 2022, 23 pages.
Notification of Reasons for Rejection for Japanese Patent Application No. 2021-518715, mailed Apr. 26, 2022, 9 pages.
Non-Final Office Action for U.S. Appl. No. 17/162,259, mailed Oct. 13, 2023, 16 pages.
Final Office Action for U.S. Appl. No. 17/148,108, mailed Oct. 27, 2023, 15 pages.
Final Office Action for U.S. Appl. No. 17/148,133, mailed Oct. 4, 2023, 10 pages.
Advisory Action for U.S. Appl. No. 17/162,259, mailed Sep. 21, 2023, 3 pages.
Non-Final Office Action for U.S. Appl. No. 17/162,259, mailed Oct. 26, 2023, 18 pages.
Non-Final Office Action for U.S. Appl. No. 17/162,283, mailed Sep. 1, 2023, 11 pages.
Notice of Allowance and Examiner-Initiated Interview Summary for U.S. Appl. No. 17/173,457, mailed Oct. 17, 2023, 10 pages.
Non-Final Office Action for U.S. Appl. No. 17/201,061, mailed Nov. 8, 2023, 19 pages.
Advisory Action for U.S. Appl. No. 17/201,061, mailed Sep. 27, 2023, 3 pages.
Arora, Prerna, et al., "B.1.617.2 enters and fuses lung cells with increased efficiency and evades antibodies induced by infection and vaccination," Cell Reports, vol. 37, Oct. 12, 2021, 12 pages.
Caly, Leon, et al., "The FDA-approved drug ivermectin inhibits the replication of SARS-CoV-2 in vitro," Antiviral Research, vol. 178, Apr. 3, 2020, Elsevier B.V., 4 pages.

(56) References Cited

OTHER PUBLICATIONS

Cele, Sandile, et al., "Escape of SARS-CoV-2 501Y.V2 from neutralization by convalescent plasma," Nature, vol. 593, May 6, 2021, 18 pages.
Cheng, Ya-Wen, et al., "D614G Substitution of SARS-CoV-2 Spike Protein Increases Syncytium Formation and Virus Titer via Enhanced Furin-Mediated Spike Cleavage," mBio, vol. 12, Issue 4, Jul. 27, 2021, 11 pages.
Do, et al., "A robust SARS-CoV-2 replication model in primary human epithelial cells at the air liquid interface to assess antiviral agents," Antiviral Research, vol. 192, Jun. 26, 2021, Elsevier, B.V., 8 pages.
Fulcher, et al., "Human Nasal and Tracheo-Bronchial Respiratory Epithelial Cell Culture," Methods in Molecular Biology, vol. 945, Chapter 8, 2012, pp. 109-121.
Gong, et al., "Contribution of single mutations to selected SARS-CoV-2 emerging variants spike antigenicity," Virology, vol. 563, Sep. 11, 2021, Elsevier Inc., 12 pages.
Good, Steven, et al., "AT-527 a Double Prodrug of a Guanosine Nucleotide Analog, Is a Potent Inhibitor of SARS-CoV-2 In Vitro and a Promising Oral Antiviral for Treatment of Covid-19," Antimicrobial Agents and Chemotherapy, vol. 65, Issue 4, Apr. 2021, 12 pages.
Harvey, William, et al., "SARS-CoV-2 variants, spike mutations and immune escape," Nature Reviews: Microbiology, vol. 19, Jul. 2021, pp. 409-424.
Heinen, Natalie, et al., "In Vitro Lung Models and Their Application to Study SARS-CoV-2 Pathogenesis and Disease," Viruses, vol. 13, Apr. 28, 2021, 17 pages.
Hou, Yixuan, et al., "SARS-CoV-2 Reverse Genetics Reveals a Variable Infection Gradient in the Respiratory Tract," Cell, vol. 182, Jul. 23, 2020, Elsevier Inc., 32 pages.
Huang, Ni, et al., "SARS-CoV-2 infection of the oral cavity and saliva," Nature Medicine, vol. 27, May 2021, 27 pages.
Krause, Philip, et al., "SARS-CoV-2 Variants and Vaccines," New England Journal of Medicine, vol. 385, Issue 2, Jul. 8, 2021, Massachusetts Medical Society, pp. 179-186.
Kumar, Sanjeev, et al., "Current status of therapeutic monoclonal antibodies against SARS-CoV-2," PLOS Pathogens, Sep. 3, 2021, 8 pages.
Levin, "Waning Immune Humoral Response to BNT162b2 Covid-19 Vaccine over 6 Months," New England Journal of Medicine, Oct. 6, 2021, Massachusetts Medical Society, 11 pages.
Liu, Haolin, et al., "The Lambda variant of SARS-CoV-2 has a better chance than the Delta variant to escape vaccines," Aug. 26, 2021, bioRxiv, 26 pages.
Liu, Jia, et al., "Hydroxychloroquine, a less toxic derivative of chloroquine, is effective in inhibiting SARS-CoV-2 infection in vitro," Cell Discovery, vol. 6, Issue 16, Mar. 18, 2020, 4 pages.
Liu, Yang, "Delta spike P681R mutation enhances SARS-CoV-2 fitness over Alpha variant," Sep. 5, 2021, bioRxiv, 29 pages.
Marchesan, et al., "The 'oral' history of COVID-19: Primary infection, salivary transmission, and post-acute Implications," Journal of Periodontology, vol. 92, American Academy of Periodontology, Jul. 2021, pp. 1357-1367.
McCullough, Peter, et al., "Pathophysiological Basis and Rationale for Early Outpatient Treatment of SARS-CoV-2 (COVID-19) Infection," The American Journal of Medicine, Review, vol. 134, Issue 1, Jan. 2021, Elsevier Inc., pp. 16-22.
Motozono, Chihiro, et al., "SARS-CoV-2 spike L452R variant evades cellular immunity and increases infectivity," Cell Host and Microbe, vol. 29, Jul. 14, 2021, Elsevier Inc., 24 pages.
Naaber, Paul, et al., "Dynamics of antibody response to BNT162b2 vaccine after six months: a longitudinal prospective study," The Lancet Regional Health—Europe, Sep. 6, 2021, 9 pages.
Planas, Delphine, et al., "Reduced sensitivity of SARS-CoV-2 variant Delta to antibody neutralization," Nature, vol. 596, Jul. 8, 2021, 20 pages.
Plante, Jessica, et al., "Spike mutation D614G alters SARS-CoV-2 fitness," Nature, vol. 592, Oct. 26, 2020, 22 pages.

Pouwels, Koen, et al., "Effect of Delta variant on viral burden and vaccine effectiveness against new SARS-CoV-2 infections in the UK," Nature Medicine, Oct. 14, 2021, 25 pages.
Pruijssers, Andrea, et al., "Remdesivir Inhibits SARS-CoV-2 in Human Lung Cells and Chimeric SARS-CoV Expressing the SARS-CoV-2 RNA Polymerase in Mice," Cell Reports, vol. 32, Jul. 21, 2020, 15 pages.
Sellgren, et al., "A biomimetic multicellular model of the airways using primary human cells," Lab on a Chip, Jun. 2014, The Royal Society of Chemistry, 10 pages.
Sheahan, Timothy, et al., "An orally bioavailable broad spectrum antiviral inhibits SARS-CoV-2 in human airway epithelial cell cultures and multiple coronaviruses in mice," Science Translational Medicine, Research Article, vol. 12, Apr. 29, 2020, 16 pages.
Stasko, Nathan, et al., "A randomized, controlled, feasibility study of RD-X19 in patients with mild-to-moderate COVID-19 in the outpatient setting," Oct. 25, 2021, medRxiv, 30 pages.
Stasko, Nathan, et al., "Visible blue light inhibits infection and replication of SARS-CoV-2 at doses that are well-tolerated by human respiratory tissue," Scientific Reports, vol. 11, Oct. 18, 2021, 14 pages.
Touret, Franck, et al., "Preclinical evaluation of Imatinib does not support its use as an antiviral drug against SARS-CoV-2," Antiviral Research, vol. 193, Jul. 12, 2021, 8 pages.
Touret, Franck, et al., "Replicative Fitness of a SARS-CoV-2 201/501Y.V1 Variant from Lineage B.1.1.7 in Human Reconstituted Bronchial Epithelium," mBio, vol. 12, Issue 4, Jul. 2021, 4 pages.
Wang, Pengfei, et al., "Antibody resistance of SARS-CoV-2 variants B.1.351 and B.1.1.7," Nature, vol. 593, May 6, 2021, 18 pages.
Wildera, Marek, et al., "Limited Neutralization of Authentic Severe Acute Respiratory Syndrome Coronavirus 2 Variants Carrying E484K In Vitro," The Journal of Infectious Diseases, Jul. 5, 2021, pp. 1109-1114.
Final Office Action for U.S. Appl. No. 16/709,550, mailed Dec. 27, 2021, 9 pages.
Advisory Action for U.S. Appl. No. 17/410,154, mailed Jan. 25, 2022, 3 pages.
Non-Final Office Action for U.S. Appl. No. 17/410,166, mailed Jan. 12, 2022, 12 pages.
Examination Report for Australian Patent Application No. 2021239894, mailed Nov. 9, 2021, 3 pages.
First Office Action for Chinese Patent Application No. 202010561507.X, mailed Oct. 19, 2021, 54 pages.
Non-Final Office Action for U.S. Appl. No. 16/709,550, mailed Jul. 12, 2021, 12 pages.
Non-Final Office Action for U.S. Appl. No. 16/898,385, mailed Aug. 16, 2021, 12 pages.
Notice of Allowance for U.S. Appl. No. 17/117,889, mailed Aug. 30, 2021, 9 pages.
Non-Final Office Action for U.S. Appl. No. 17/410,154, mailed Nov. 8, 2021, 16 pages.
Final Office Action for U.S. Appl. No. 17/410,154, mailed Dec. 22, 2021, 15 pages.
Second Office Action for Chinese Patent Application No. 202010561507.X, mailed Jul. 15, 2022, 33 pages.
Advisory Action for U.S. Appl. No. 17/410,166, mailed Sep. 7, 2022, 3 pages.
Final Office Action for U.S. Appl. No. 17/201,120, mailed Sep. 23, 2022, 34 pages.
Ahmed, Imran, et al., "Recent Patents on Light-Based Anti-Infective Approaches," Author Manuscript, Recent Patents on Anti-Infective Drug Discovery, vol. 13, Issue 1, 2018, 28 pages.
Akaberi, Dario, et al., "Mitigation of the replication of SARS-CoV-2 by nitric oxide in vitro," Redox Biology, vol. 37, Sep. 21, 2020, Elsevier B.V., 5 pages.
Author Unknown, "Assessing COVID-19-Related Symptoms in Outpatient Adult and Adolescent Subjects in Clinical Trials of Drugs and Biological Products for Covid-19 Prevention or Treatment," Guidance for Industry, US Department of Health and Human Services, Sep. 2020, 14 pages.
Baric, Ralph, "Emergence of a Highly Fit SARS-CoV-2 Variant," New England Journal of Medicine, vol. 383, Issue 27, Dec. 31, 2020, pp. 2684-2686.

(56) References Cited

OTHER PUBLICATIONS

Fajnzylber, Jesse, et al., "SARS-CoV-2 viral load is associated with increased disease severity and mortality," Nature Communications, vol. 11, Issue 1, Oct. 30, 2020, 9 pages.
Hamblin, Michael, "Mechanisms and Mitochondrial Redox Signaling in Photobiomodulation," Author Manuscript, Photochemistry and Photobiology, vol. 94, Issue 2, Mar. 2018, 31 pages.
Huang, Ni, et al., "Integrated Single-Cell Atlases Reveal an Oral SARS-CoV-2 Infection and Transmission Axis," medrXiv, Oct. 29, 2020, 22 pages.
Kim, Peter, et al., "Therapy for Early COVID-19: A Critical Need," JAMA, vol. 324, Issue 21, Nov. 11, 2020, American Medical Association, pp. 2149-2150.
Quirk, Brendan, et al., "What Lies at the Heart of Photobiomodulation: Light, Cytochrome C Oxidase, and Nitric Oxide—Review of the Evidence," Photobiomodulation, Photomedicine, and Laser Surgery, vol. 38, Issue 9, Jul. 2020, pp. 527-530.
To, KK, et al., "Temporal profiles of viral load in posterior oropharyngeal saliva samples and serum antibody responses during infection by SARS-CoV-2: an observational cohort study," Lancet Infectious Diseases, vol. 20, Issue 5, Mar. 23, 2020, 11 pages.
Wyllie, Anne, et al., "Saliva or nasopharyngeal swab specimens for detection of SARS-Cov-2," New England Journal of Medicine, vol. 383, Issue 13, Sep. 24, 2020, 4 pages.
Xu, Hao, et al., "High expression of ACE2 receptor of 2019-nCoV on the epithelial cells of oral mucosa," International Journal of Oral Science, vol. 12, Issue 8, Feb. 24, 2020, 5 pages.
Soukos, Nikolaos, et al., "Phototargeting Oral Black-Pigmented Bacteria," Antimicrobial Agents and Chemotherapy, Apr. 2005, vol. 49, Issue 4, pp. 1391-1396.
Non-Final Office Action for U.S. Appl. No. 17/117,889, mailed Mar. 19, 2021, 17 pages.
Applicant-Initiated Interview Summary for U.S. Appl. No. 17/117,889, mailed Apr. 19, 2021, 2 pages.
Final Office Action for U.S. Appl. No. 17/117,889, mailed Apr. 30, 2021, 19 pages.
Author Unknown, "Scientific Breakthrough: Phototherapy Device," Facebook Timeline Photo, medicsBLU, Oct. 1, 2020, facebook.com/medicsblu/, 4 pages.
Ankhzaya, "Airway management," slideshow, www.slideshare.net/gasilu/airway-management-111268937, Aug. 24, 2018, 87 pages.
Liu, et al., "Creation of a standardized geometry of the human nasal cavity," Journal of Applied Physiology, vol. 106, Jan. 2009, pp. 784-795.
International Search Report and Written Opinion for International Patent Application No. PCT/US2021/019785, mailed Jun. 15, 2021, 18 pages.
Final Office Action for U.S. Appl. No. 16/709,550, mailed Feb. 17, 2021, 12 pages.
Advisory Action and Examiner-Initiated Interview Summary for U.S. Appl. No. 17/117,889, mailed May 19, 2021, 5 pages.
Advisory Action for U.S. Appl. No. 17/117,889, mailed Jun. 4, 2021, 3 pages.
Non-Final Office Action for U.S. Appl. No. 16/709,550, mailed Apr. 30, 2020, 13 pages.
Notice of Allowance and Applicant-Initiated Interview Summary for U.S. Appl. No. 15/222,243, mailed Dec. 19, 2019, 11 pages.
Final Office Action for U.S. Appl. No. 15/222,243, mailed Jul. 29, 2019, 12 pages.
Notice of Allowance and Applicant-Initiated Interview Summary for U.S. Appl. No. 15/222,199, mailed Sep. 18, 2019, 11 pages.
Final Office Action for U.S. Appl. No. 15/222,199, mailed Jul. 29, 2019, 9 pages.
International Preliminary Report on Patentability for PCT/US2016/044403, mailed Feb. 8, 2018, 7 pages.
Non-Final Office Action for U.S. Appl. No. 15/222,243, mailed Jan. 11, 2019, 10 pages.
Non-Final Office Action for U.S. Appl. No. 15/222,199, mailed Jan. 11, 2019, 9 pages.
Zein, Randa, et al., "Review of light parameters and photobiomodulation efficacy: dive into complexity," Journal of Biomedical Optics, vol. 23, Issue 12, Dec. 2018, 17 pages.
Zupin, Luisa, et al., "Antiviral properties of blue laser in an in vitro model of HSV-1 infection," Microbial Immunal, Letter to the Editor, vol. 62, 2018, pp. 477-479.
Zupin, Luisa, et al., "Photobiomodulation therapy reduces viral load and cell death in ZIKV-infected glioblastoma cell line," Lasers in Medical Science, vol. 33, Jul. 2018, Springer Nature, pp. 2011-2013.
International Search Report and Written Opinion for PCT/US2016/044400, mailed Oct. 4, 2016, 8 pages.
International Preliminary Report on Patentability for PCT/US2016/044400, mailed Feb. 8, 2018, 7 pages.
Final Office Action for U.S. Appl. No. 17/117,858, mailed Feb. 14, 2024, 11 pages.
Advisory Action for U.S. Appl. No. 17/148,108, mailed Jan. 3, 2024, 3 pages.
Applicant-Initiated Interview Summary for U.S. Appl. No. 17/148,108, mailed Jan. 23, 2024, 2 pages.
Non-Final Office Action for U.S. Appl. No. 17/148,108, mailed Feb. 20, 2024, 10 pages.
Notice of Allowance for U.S. Appl. No. 17/148,133, mailed Jan. 24, 2024, 8 pages.
Notice of Allowance for U.S. Appl. No. 17/162,283, mailed Feb. 12, 2024, 8 pages.
Notice of Allowance for U.S. Appl. No. 17/173,457, mailed Jan. 29, 2024, 10 pages.
International Search Report and Written Opinion for International Patent Application No. PCT/US2023/015757, mailed Jun. 30, 2023, 14 pages.
Non-Final Office Action for U.S. Appl. No. 17/148,108, mailed Jul. 19, 2023, 14 pages.
Advisory Action and Examiner-Initiated Interview Summary for U.S. Appl. No. 17/148,124, mailed May 26, 2023, 5 pages.
Non-Final Office Action for U.S. Appl. No. 17/148,133, mailed Jun. 15, 2023, 9 pages.
Final Office Action for U.S. Appl. No. 17/162,259, mailed Jul. 14, 2023, 18 pages.
Advisory Action for U.S. Appl. No. 17/162,283, mailed Jun. 23, 2023, 3 pages.
Non-Final Office Action for U.S. Appl. No. 17/173,457, mailed Jun. 9, 2023, 9 pages.
Final Office Action for U.S. Appl. No. 17/201,061, mailed Jul. 26, 2023, 17 pages.
Examination Report for European Patent Application No. 16831333.6, mailed May 7, 2024, 7 pages.
International Search Report and Written Opinion for International Patent Application No. PCT/US2024/016811, mailed May 29, 2024, 14 pages.
Notice of Allowance for U.S. Appl. No. 17/117,858, mailed May 22, 2024, 7 pages.
Final Office Action for U.S. Appl. No. 17/148,124, mailed May 28, 2024, 23 pages.
Final Office Action for U.S. Appl. No. 17/162,259, mailed May 20, 2024, 22 pages.
Notice of Allowance for U.S. Appl. No. 17/201,061, mailed Jun. 12, 2024, 10 pages.
Final Office Action for U.S. Appl. No. 17/148,124, mailed Mar. 13, 2023, 29 pages.
Notice of Allowance and Examiner-Initiated Interview Summary for U.S. Appl. No. 17/410,154, mailed Mar. 9, 2023, 14 pages.
Non-Final Office Action for U.S. Appl. No. 17/162,259, mailed Apr. 7, 2023, 18 pages.
Final Office Action for U.S. Appl. No. 17/162,283, mailed Apr. 10, 2023, 10 pages.
Advisory Action for U.S. Appl. No. 17/173,457, mailed May 1, 2023, 3 pages.
Non-Final Office Action for U.S. Appl. No. 17/201,061, mailed Apr. 20, 2023, 19 pages.
Abeyakirthi, Sharnika, "Nitric oxide," DermNet NZ, 2009, 4 pages, www.dermnetnz.org/topics/nitric-oxide/.

(56) References Cited

OTHER PUBLICATIONS

Adamskaya, Natalia et al., "Light therapy by blue LED improves wound healing in an excision model in rats," Injury, 2010, 5 pages.
Adusumilli, Nagasai, et al., "Harnessing nitric oxide for preventing, limiting and treating the severe pulmonary consequences of COVID-19," Nitric Oxide, vol. 103, Jul. 2020, Elsevier Inc., 5 pages.
Akerstrom, Sara, et al., "Nitric Oxide Inhibits the Replication Cycle of Severe Acute Respiratory Syndrome Coronavirus," Journal of Virology, vol. 79, Issue 3, Feb. 2005, pp. 1966-1969.
Akerstrom, Sara, et al., "Dual effect of nitric oxide on SARS-CoV replication: Viral RNA production and palmitoylation of the S protein are affected," Virology, vol. 395, Oct. 2009, Elsevier Inc., 9 pages.
Andrew, Penelope J. et al., "Enzymatic function of nitric oxide synthases," Cardiovascular Research, vol. 43, No. 3, Aug. 15, 1999, pp. 521-531.
Author Unknown, "dpl Oral Care—for Healthy Teeth & Gums," Product Brief, Revive Light Therapy, revivelighttherapy.com/product/dpl-oral-care-light-therapy-system-teeth-whitening/, accessed Jan. 31, 2021, 5 pages.
Author Unknown, "Healed by Light," Digi-Key Electronics, Jul. 1, 2014, 4 pages, www.digikey.com/es/articles/techzone/2014/jul/healed-by-light.
Author Unknown, "IPL Hair Removal," Spectrum Science & Beauty, Spectrum Blog, Sep. 16, 2014, 3 pages, www.spectrumsciencebeauty.com.au/ipl-hair-removal/#prettyPhoto.
Author Unknown, "Near—IR Photoluminescent Dyes for Molecular Labeling," NanoQuantum, Technology, 2013, 7 pages, www.nanoquantum.com/Technology.html.
Author Unknown, "Philips Blue Touch," Koninklijke Philips N.V., Version 1.0.1, Sep. 1, 2013, 2 pages.
Author Unknown, "Safety and Efficacy of UVC to Fight Covid-19," Gilbert W. Beebe Webinar Series, Program Agenda, Sep. 16, 2020, 6 pages.
Author Unknown, "Theradome Laser Helmet Review—a 120 Day Continuous Journal," Prevent Hair Loss Products, Jan. 14, 2014, retrieved Jun. 27, 2017, web.archive.org/web/20140610024017/http://preventhairlossproducts.com:80/theradome-laser-helmet-review-120-day-continuous-journal/, pp. 1-4.
Author Unknown, "Vio Orb—Antimicrobial Light Ball," Product Brief, Revive Light Therapy, revivelighttherapy.com/product/envirohygiene-orb-antimicrobial-light-ball/, accessed Jan. 31, 2021, 6 pages.
Avci, Pinar et al., "Low-Level Laser (Light) Therapy (LLLT) for Treatment of Hair Loss," Lasers in Surgery and Medicine, vol. 46, 2014, pp. 144-151.
Avci, Pinar et al., "Low-Level Laser (Light) Therapy (LLLT) in Skin: Stimulating, Healing, Restoring," Seminars in Cutaneous Medicine and Surgery, vol. 32, No. 1, 2013, pp. 41-52.
Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.
Barolet, Daniel, "Light-Emitting Diodes (LEDs) in Dermatology," Seminars in Cutaneous Medicine and Surgery, vol. 27, No. 4, Dec. 1, 2008, pp. 227-238.
Bashkatov et al., "Optical properties of human skin, subcutaneous and mucous tissues in the wavelength range from 400-2000 nm," Journal of Physics D: Applied Physics, vol. 38, Jul. 2005, IOP Publishing Ltd, pp. 2543-2555.
Beck, Sara, et al., "Comparison of UV-Induced Inactivation and RNA Damage in MS2 Phage across the Germicidal UV Spectrum," Applied and Environmental Microbiology, vol. 82, Issue 5, Mar. 2016, pp. 1468-1474.
Beigel, JH, et al., "Remdesivir for the Treatment of Covid-19—Final Report," New England Journal of Medicine, vol. 383, Issue 19, Nov. 5, 2020, pp. 1813-1826.
Besaratinia, Ahmad, et al., "DNA lesions induced by UV A1 and B radiation in human cells: Comparative analyses in the overall genome and in the p53 tumor suppressor gene," PNAS, vol. 102, Issue 29, Jul. 2005, pp. 10058-10063.
Buonnano, Manuela, et al., "Far-UVC light (222 nm) efficiently and safely inactivates airborne human coronaviruses," Scientific Reports, Jun. 24, 2020, 8 pages.
Buonnano, Manuela, et al., "Germicidal Efficacy and Mammalian Skin Safety of 222-nm UV Light," Radiation Research, vol. 187, 2017, Radiation Research Society, 2017, pp. 493-501.
Cals-Grierson, M.-M. et al., "Nitric oxide function in the skin," Nitric Oxide, vol. 10, No. 4, Jun. 2004, pp. 179-193.
Chaves, Maria Emília De Abreu et al., "Effects of low-power light therapy on wound healing: Laser × LED," Anais Brasileiros de Dermatologia, vol. 89, No. 4, Jul./Aug. 2014, pp. 616-623.
Chen, Luni, et al., "Inhalation of Nitric Oxide in the Treatment of Severe Acute Respiratory Syndrome: A Rescue Trial in Beijing," Brief Report, Clinical Infectious Diseases, vol. 39, Oct. 2004, pp. 1531-1535.
Creagh-Brown, Benedict, et al., "Bench-to-bedside review: Inhaled nitric oxide therapy in adults," Critical Care, vol. 13, Issue 3, May 2009, BioMed Central Ltd, 8 pages.
Dai, Tianhong, et al., "Blue light for infectious diseases: Propionibacterium acnes, Helicobacter pylori, and beyond?," NIH-PA, Author Manuscript, 2012, Elsevier Ltd., 31 pages.
Darnelll, Miriam, et al., "Evaluation of inactivation methods for severe acute respiratory syndrome coronavirus in noncellular blood products," Transfusion, vol. 46, Oct. 2006, 8 pages.
De Marco, Federico, "Oxidative Stress and HPV Carcinogenesis," Viruses, vol. 5, Feb. 2013, pp. 708-731.
Donnarumma, G., et al., "Inhibition of HSV-1 Replication by Laser Diode-Irradiation: Possible Mechanism of Action," Journal of Immunopathology and Pharmacology, vol. 23, Issue 4, 2010, Biolife, pp. 1167-1176.
Dorrington, Michael, et al., "NF-KB Signaling in Macrophages: Dynamics, Crosstalk, and Signal Integration," Frontiers in Immunology, vol. 10, Apr. 9, 2019, 12 pages.
Eadie, Ewan, et al., "Extreme Exposure to Filtered Far-UVC: A Case Study," Ninewells Hospital and Medical School, Sep. 25, 2020, 14 pages.
Enwemeka, Chukuka, et al., "Blue 470-nm Light Kills Methicillin-Resistant *Staphylococcus aureus* (MRSA) in Vitro," Photomedicine and Laser Surgery, vol. 27, Issue 2, 2009, 6 pages.
Enwemeka, Chukuka, et al., "Light as a potential treatment for pandemic coronavirus infections: A perspective," Journal of Photochemistry & Photobiology, B: Biology, vol. 207, May 2020, 7 pages.
Enwemeka, Chukuka, et al., "Visible 405 nm SLD Light Photo-Destroys Methicillin-Resistant *Staphylococcus aureus* (MRSA) In Vitro," Lasers in Surgery and Medicine, vol. 40, 2008, pp. 734-737.
Farivar, Shirin et al., "Biological Effects of Low Level Laser Therapy," Journal of Lasers in Medical Sciences, vol. 6, No. 2, Spring 2014, pp. 58-62.
Feelisch, Martin et al., "Concomitant S-, N-, and heme-nitrosis(yl)ation in biological tissues and fluids: implications for the fate of NO in vivo," FASEB, vol. 16, No. 13, Nov. 2002, pp. 1775-1785.
Ferrari-Light, Dana, et al., "The Utility of Near-Infrared Fluorescence and Indocyanine Green During Robotic Pulmonary Resection," Frontiers in Surgery, Review, vol. 6, Aug. 2019, 7 pages.
Finsen, Niels, "The Red Light Treatment of Small-Pox," The British Medical Journal, Dec. 7, 1895, pp. 1412-1414.
Garza, Felix, et al., "Visible Blue Light Therapy: Molecular Mechanisms and Therapeutic Opportunities," Current Medical Chemistry, 2018, vol. 25, Bentham Science Publishers, pp. 5564-5577.
Glazer-Hockstein, "Could Blue Light-Blocking Lenses Decrease the Risk of Age-Related Macular Degeneration," Retina, vol. 26, 2006, 4 pages.
Gupta, Asheesh et al., "History and Fundamentals of Low-Level Laser (Light) Therapy," Handbook of Photomedicine, Chapter 5, CRC Press, 2014, pp. 43-52.
Hamblin, Michael, et al., "Can light-based approaches overcome antimicrobial resistance?," Drug Development Research, Jul. 2018, Wiley Periodicals, Inc., 20 pages.

(56) References Cited

OTHER PUBLICATIONS

Hamblin, Michael, et al., "Mechanisms of Low Level Light Therapy," Proceedings of the SPIE, vol. 6140, Feb. 10, 2006, pp. 614001-1 to 641001-12.
Non-Final Office Action for U.S. Appl. No. 16/898,385, mailed Jun. 7, 2022, 13 pages.
Non-Final Office Action for U.S. Appl. No. 17/410,166, mailed May 27, 2022, 11 pages.
Notice of Acceptance for Australian Patent Application No. 2021239894, mailed Jun. 15, 2022, 3 pages.
International Search Report and Written Opinion for International Patent Application No. PCT/US2022/019428, mailed Jun. 14, 2022, 16 pages.
Examination Report for European Patent Application No. 16831333.6, mailed May 20, 2022, 6 pages.
Advisory Action and Examiner-Initiated Interview Summary for U.S. Appl. No. 17/410,154, mailed Jul. 5, 2022, 4 pages.
Final Office Action for U.S. Appl. No. 17/410,166, mailed Jul. 1, 2022, 16 pages.
Non-Final Office Action for U.S. Appl. No. 17/162,259, mailed Jul. 6, 2022, 17 pages.
Non-Final Office Action for U.S. Appl. No. 17/410,154, mailed Jul. 28, 2022, 21 pages.
Office Action for Canadian Patent Application No. 3174573, mailed Aug. 5, 2024, 4 pages.
Examination Report for European Patent Application No. 21713288.5, mailed Aug. 19, 2024, 4 pages.
Advisory Action for U.S. Appl. No. 17/148,090, mailed Jul. 9, 2024, 3 pages.
Notice of Allowance for U.S. Appl. No. 17/148,108, mailed Jul. 10, 2024, 8 pages.
Advisory Action and Examiner-Initiated Interview Summary for U.S. Appl. No. 17/148,124, mailed Aug. 9, 2024, 6 pages.
Advisory Action for U.S. Appl. No. 17/162,259, mailed Jul. 25, 2024, 3 pages.
Hamblin, Michael, "Mechanisms of Low Level Light Therapy," Aug. 14, 2008, 22 pages, photobiology.info/Hamblin.html.
Hamblin, Michael R., "The Role of Nitric Oxide in Low Level Light Therapy," Proceedings of SPIE, vol. 6846, 2008, pp. 684602-1 to 684602-14.
Hessling, Martin, et al., "Selection of parameters for thermal coronavirus inactivation—a data-based recommendation," GMS Hygiene and Infection Control, vol. 15, 2020, 7 pages.
Horby, Peter, et al., "Dexamethasone in Hospitalized Patients with Covid-19—Preliminary Report," New England Journal of Medicine, Jul. 17, 2020, 11 pages.
Jackson, George, et al., "Prevalidation of an Acute Inhalation Toxicity Test Using the EpiAirway In Vitro Human Airway Model," Applied In Vitro Toxicology, vol. 4, Issue 2, 2018, Mary Ann Liebert, Inc., pp. 149-158.
Jensen, Caleb, et al., "Is it Time to Start Transitioning From 2D to 3D Cell Culture," Frontiers in Molecular Biosciences, Review, vol. 7, Mar. 2020, 15 pages.
Jin, Jin, et al., "Noncanonical NF-KB Pathway Controls the Production of Type I Interferons in Antiviral Innate Immunity," Immunity, vol. 40, Mar. 2014, Elsevier Inc., pp. 342-354.
Karu, Tiina I., "Low-Power Laser Therapy," Biomedical Photonics Handbook, Chapter 48, CRC Press, 2003, pp. 48-1 to 48-25.
Kelm, Malte, "Nitric oxide metabolism and breakdown," Review, Biochimica et Biophysica Acta, vol. 1411, 1999, Elsevier Science B.V., pp. 273-289.
Kingsley, David, et al., "Oxygen-dependent laser inactivation of murine norovirus using visible light lasers," Virology Journal, Jul. 31, 2018, 8 pages.
Kirima, Kazuyoshi et al., "Evaluation of systemic blood NO dynamics by EPR spectroscopy: HbNO as an endogenous index of NO," American Journal of Physiology Heart and Circulatory Physiology, vol. 285, No. 2, Aug. 2003, pp. H589-H596.
Kitchel, Elaine, "The Effects of Blue Light on Ocular Health," Journal of Visual Impairment and Blindness, Jun. 2000, AFB, pp. 399-403.
Klein, Eili, et al., "The frequency of influenza and bacterial coinfection: a systematic review and meta-analysis," Influenza and Other Respiratory Viruses, vol. 10, Issue 5, May 2016, John Wiley & Sons Ltd., pp. 394-403.
Kovacs, Izabella et al., "Nitric oxide-based protein modification: formation and site-specificity of protein S-nitrosylation," Frontiers in Plant Science, vol. 4, Article 137, May 14, 2013, 10 pages.
Leong, Mimi, "Effects of Light-Emitting Diode Photostimulation on Burn Wound Healing," Thesis, The University of Texas Graduate School of Biomedical Sciences at Galveston, May 2006, 92 pages.
Li, Jie, et al., "Involvement of the Toll-Like Receptor/Nitric Oxide Signaling Pathway in the Pathogenesis of Cervical Cancer Caused by High-Risk Human Papillomavirus Infection," Biomed Research International, 2017, Hindawi, 9 pages.
Lubart, et al., "A Possible Mechanism for the Bactericidal Effect of Visible Light," Review Article, Laser Therapy, vol. 20, 2011, pp. 17-22.
Mandel, Arkady, et al., "A renaissance in low-level laser (light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Marullo, Rosella, et al., "HPV16 E6 and E7 proteins induce a chronic oxidative stress response via NOX2 that causes genomic instability and increased susceptibility to DNA damage in head and neck cancer cells," Carcinogenesis, vol. 36, Issue 11, 2015, Oxford University Press, pp. 1397-1406.
Moseley, Harry, et al., "Population reference intervals for minimal erythemal doses in monochromator phototesting," Photodermatology, Photoimmunology & Photomedicine, vol. 25, 2009, pp. 8-11.
Narita, Kouji, et al., "Chronic irradiation with 222-nm UVC light induces neither DNA damage nor epidermal lesions in mouse skin, even at high doses," Research Article, PLOS One, doi.org/10.1371/journal.pone.0201259, Jul. 25, 2018, 9 pages.
Narita, Kouji, et al., "Disinfection and healing effects of 222-nm UVC light on methicillin-resistant Staphylococcus aureus infection in mouse wounds," Dissertation, Hirosaki University Graduate School of Medicine, 2017, Elsevier, 36 pages.
Narita, Kouji, et al., "Ultraviolet C light with wavelength of 222 nm inactivates a wide spectrum of microbial pathogens," Journal of Hospital Infection, vol. 105, Mar. 31, 2020, Elsevier Ltd., pp. 459-467.
Perdiz, Daniel, et al., "Distribution and Repair of Bipyrimidine Photoproducts in Solar UV-irradiated Mammalian Cells," Journal of Biological Chemistry, vol. 275, Issue 35, Sep. 2000, pp. 26732-26742.
Pfeifer, Gerd, et al., "UV wavelength-dependent DNA damage and human non-melanoma and melanoma skin cancer," Author Manuscript, Journal of Photochemistry and Photobiology, vol. 11, Issue 1, Jan. 2012, 14 pages.
Phurrough, Steve et al., "Decision Memo for Infrared Therapy Devices (CAG-00291N)," Centers for Medicare & Medicaid Services, Oct. 24, 2006, 37 pages.
Poyton, Robert O. et al., "Therapeutic Photobiomodulation: Nitric Oxide and a Novel Function of Mitochondrial Cytochrome C Oxidase," Discovery Medicine, Feb. 20, 2011, 11 pages.
Ramakrishnan, Praveen, et al., "Cytotoxic responses to 405 nm light exposure in mammalian and bacterial cells: Involvement of reactive oxygen species," Toxicology in Vitro, vol. 33, Feb. 2016, Elsevier B.V., pp. 54-62.
Ravanant, Jean-Luc, et al., "Direct and indirect effects of UV radiation on DNA and its components," Journal of Photochemistry and Photobiology, vol. 63, 2001, pp. 88-102.
Richardson, Tobias, et al., "Inactivation of murine leukaemia virus by exposure to visible light," Virology, vol. 341, 2005, Elsevier Inc., pp. 321-329.
Sabino, Caetano, et al., "Light-based technologies for management of COVID-19 pandemic crisis," Journal of Photochemistry and Photobiology, Aug. 2020, Elsevier B.V., 8 pages.

(56) References Cited

OTHER PUBLICATIONS

Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.

Saura, Marta, et al., "An Antiviral Mechanism of Nitric Oxide: Inhibition of a Viral Protease," Immunity, vol. 10, Jan. 1999, Cell Press, 8 pages.

Serrage, Hannah, et al., "Under the spotlight: mechanisms of photobiomodulation concentrating on blue and green light," Photochemical and Photobiological Sciences, Jun. 2019, 43 pages.

St. Denis, Tyler, et al., "Killing Bacterial Spores with Blue Light: When Innate Resistance Meets the Power of Light," Photochemistry and Photobiology, vol. 89, Issue 1, Sep. 2012, Wiley Preiodicals, Inc., 7 pages.

Tomb, Rachael, et al., "Inactivation of Streptomyces phage φC31 by 405 nm light," Bacteriophage, vol. 4, Jul. 2014, Landes Bioscience, 7 pages.

Tomb, Rachael, et al., "New Proof-of-Concept in Viral Inactivation: Virucidal Efficacy of 405 nm Light Against Feline Calicivirus as a Model for Norovirus Decontamination," Food Environ Virol, Dec. 2016, pp. 159-167.

Tomoroni, et al., "A Novel Laser Fiberscope for Simultaneous Imaging and Phototherapy of Peripheral Lung Cancer," Chest, vol. 156, Issue 3, Sep. 2019, 8 pages.

Tsen, KT, et al., "Inactivation of viruses by coherent excitations with a low power visible femtosecond laser," Virology Journal, Jun. 2007, BioMed Central Ltd., 5 pages.

Tsen, Shaw-Wei, et al., "Chemical-free inactivated whole influenza virus vaccine prepared by ultrashort pulsed laser treatment," Journal of Biomedical Optics, vol. 20, Issue 5, May 2015, 8 pages.

Tsen, Shaw-Wei, et al., "Inactivation of enveloped virus by laser-driven protein aggregation," Journal of Biomedical Optics, vol. 17, Issue 12, Dec. 2012, 8 pages.

Tsen, Shaw-Wei, "Pathogen Reduction in Human Plasma Using an Ultrashort Pulsed Laser," PLOS One, vol. 9, Issue 11, Nov. 2014, 8 pages.

Tsen, Shaw-Wei, et al., "Prospects for a novel ultrashort pulsed laser technology for pathogen inactivation," Journal of Biomedical Science, Jul. 2012, 11 pages.

Tsen, Shaw-Wei, et al., "Studies of inactivation mechanism of non-enveloped icosahedral virus by a visible ultrashort pulsed laser," Virology Journal, vol. 11, Issue 20, Feb. 2014, BioMed Central Ltd., 9 pages.

Vatansever, Fatma, et al., "Antimicrobial strategies centered around reactive oxygen species—bactericidal antibiotics, photodynamic therapy, and beyond," FEMS Microbiology Reviews, vol. 37, Issue 6, 2013, pp. 955-989.

Wei, Xue-Min, et al., "Relationship between nitric oxide in cervical microenvironment and different HPV types and effect on cervical cancer cells," Zhonghua Fu Chan Ke Za Zhi, vol. 46, Issue 4, Apr. 2011, pp. 260-265 (Abstract Only).

Williams, Vonetta, et al., "Human Papillomavirus Type 16 E6* Induces Oxidative Stress and DNA Damage," Journal of Virology, vol. 88, Issue 12, Jun. 2014, pp. 6751-6761.

Willoughby, Jamin, "Predicting Respiratory Toxicity Using a Human 3D Airway (EpiAirway) Model Combined with Multiple Parametric Analysis," Applied In Vitro Toxicology, vol. 1, Issue 1, 2015, pp. 55-65.

Wolf, Yuri, et al., "Origins and Evolution of the Global RNA Virome," mBio, vol. 9, Issue 6, Nov. 2018, 31 pages.

Office Action for Canadian Patent Application No. 3174573, mailed Oct. 20, 2023, 4 pages.

Notice of Allowance for Brazilian Patent Application No. BR1122020024964-1, mailed Nov. 27, 2023, 4 pages.

Non-Final Office Action for U.S. Appl. No. 17/148,090, mailed Dec. 13, 2023, 12 pages.

Non-Final Office Action for U.S. Appl. No. 17/148,124, mailed Dec. 18, 2023, 24 pages.

Advisory Action for U.S. Appl. No. 17/148,133, mailed Dec. 8, 2023, 3 pages.

Non-Final Office Action for U.S. Appl. No. 18/181,079, mailed Nov. 12, 2024, 14 pages.

Non-Final Office Action for U.S. Appl. No. 17/148,090, mailed Oct. 31, 2024, 12 pages.

Non-Final Office Action for U.S. Appl. No. 18/508,418, mailed Oct. 25, 2024, 10 pages.

* cited by examiner

| | 425nm Light | | | |
|---|---|---|---|---|
| | PRNT$_{50}$ | | PRNT$_{90}$ | |
| | Dose (J/cm$^2$) | Fold Change Over WA1 | Dose (J/cm$^2$) | Fold Change Over WA1 |
| WA1 | 2.8 | 0.00 | 6.2 | 0.00 |
| Alpha | 2.4 | <0 | 4.7 | <0 |
| Beta | 1.9 | <0 | 5.3 | <0 |
| Delta | 2.2 | <0 | 5.6 | <0 |
| Gamma | 1.2 | <0 | 2.9 | <0 |
| Lambda | 2.5 | <0 | 6.2 | <0 |

FIG. 3

ENHANCED TESTING AND CHARACTERIZATION TECHNIQUES FOR PHOTOTHERAPEUTIC LIGHT TREATMENTS

RELATED APPLICATIONS

This application claims the benefit of provisional patent application Ser. No. 63/123,631, filed Dec. 10, 2020, the disclosure of which is hereby incorporated herein by reference in its entirety.

FIELD OF THE DISCLOSURE

The present disclosure relates generally to devices and methods for impinging light on tissue to induce one or more biological effects, and more particularly to enhanced testing and characterization techniques for phototherapeutic light treatments.

BACKGROUND

Microorganisms, including disease-causing pathogens, can typically invade tissues of the human body via mucosal surfaces within body cavities, such as mucous membranes or mucosae of the respiratory tract. A number of respiratory diseases and infections, including viral and bacterial, can be attributed to such disease-causing pathogens. Examples include Orthomyxoviridae (e.g., influenza), common colds, coronaviridae (e.g., coronavirus), picornavirus infections, tuberculosis, pneumonia, bronchitis, and sinusitis. Most respiratory tract infections begin when a subject is exposed to pathogen particles, which can enter the body through the mouth and nose. For viral infections, cells at the site of infection must be accessible, susceptible, and permissive for virus infection and replication, and local host anti-viral defense systems must be absent or initially ineffective. Conventional treatments for infections typically involve systemic administration of antimicrobials, such as antibiotics for bacterial infections, that can sometimes lead to drug resistance and in some instances gastro-intestinal distress. Other conventional treatment protocols may involve managing and enduring symptoms while waiting for infections to clear, particularly for viral infections.

Upper respiratory tract infections, including the common cold, influenza, and those resulting from exposure to coronaviridae are widely prevalent infections that continually impact the worldwide population. In some instances, upper respiratory tract infections can progress to cause serious and sometimes fatal diseases that develop in the lower respiratory tract or elsewhere in the body. The art continues to seek improved treatment options for upper respiratory tract conditions that are capable of overcoming challenges associated with conventional treatment options.

SUMMARY

The present disclosure relates generally to devices and methods for impinging light on tissue to induce one or more biological effects, and more particularly to enhanced testing and characterization techniques for phototherapeutic light treatments. Such testing and characterization techniques may be particularly useful in the evaluation and development of light-based treatments for various infectious diseases, including multiple variants of SARS-CoV-2. In particular aspects, testing and characterization techniques are related to the direct testing of differentiated tissue models of human airway epithelia that have been exposed to various pathogens. Phototherapeutic light treatments and corresponding treatment protocols for light are also described that not only inactivate SARS-COV-2 variants in cell-free suspensions, but also inhibit SARS-CoV-2 infections at multiple stages of infection in tissue models of human airway epithelia in a variant-agnostic manner.

In one aspect, a method comprises: administering a first dose of light to a surface of a human tissue model to induce a biological effect in the human tissue model; and determining an efficacy of the first dose of light in the human tissue model based on the biological effect that is induced in the human tissue model. In certain embodiments, the biological effect comprises at least one of inactivating microorganisms, inhibiting replication of microorganisms, upregulating a local immune response, stimulating enzymatic generation of nitric oxide to increase endogenous stores of nitric oxide, releasing nitric oxide from endogenous stores of nitric oxide, and inducing an anti-inflammatory effect. In certain embodiments: the first dose of light is administered to the surface of the human tissue model after a virus stock in a first diluent is exposed to the surface of the human tissue model and after the virus stock and the first diluent have been removed from the human tissue model; and determining the efficacy of the first dose of light comprises correlating a first viral load in the human tissue model by quantifying a viral load in a first apical wash of the human tissue model, wherein the first apical wash comprises a second diluent that is a same solution as the first diluent.

In certain embodiments, the human tissue model is exposed to the virus stock for a first time period; and the first dose of light is administered at an end of a second time period from when the virus stock is exposed to the human tissue model. In certain embodiments, the end of the second time period is in a range from 30 minutes to 90 minutes after an end of the first time period. In certain embodiments, the first apical wash is completed at an end of a third time period from when the virus stock is exposed to the human tissue model. The method may further comprise administering a second dose of light to the surface of the human tissue model after the first apical wash. The method may further comprise: correlating a second viral load in the human tissue model at an end of a fourth time period after the virus stock is exposed to the human tissue model by quantifying a viral load in a second apical wash of the human tissue model, wherein the second apical wash comprises a third diluent that is a same solution as the first diluent.

In certain embodiments, the human tissue model comprises a human airway epithelia model. In certain embodiments, the virus stock comprises at least one of influenza and coronaviridae that is applied to the human airway epithelia model. In certain embodiments, the first dose of light comprises a peak wavelength in a range from 400 nanometers (nm) to 450 nm that is irradiated on the surface of the human tissue model after the at least one of the influenza and the coronaviridae is removed. In certain embodiments, the first diluent and the second diluent comprise minimum essential medium with a fetal bovine serum additive.

In another aspect, a method comprises: administering a plurality of light doses to a surface of a human tissue model to induce a biological effect in the human tissue model; and determining an efficacy of the plurality of light doses in the human tissue model based on the biological effect that is induced in the human tissue model. In certain embodiments, the biological effect comprises at least one of inactivating microorganisms, inhibiting replication of microorganisms, upregulating a local immune response, stimulating enzymatic generation of nitric oxide to increase endogenous stores of nitric oxide, releasing nitric oxide from endogenous stores of nitric oxide, and inducing an anti-inflammatory effect.

In certain embodiments, the plurality of light doses are administered to the surface of the human tissue model after a virus stock in a first diluent is exposed to the surface of the human tissue model and after the virus stock and the first diluent have been removed from the human tissue model; and determining the efficacy of the plurality of light doses comprises correlating a viral load in the human tissue model at a plurality of time intervals by quantifying an amount of a viral load in a plurality of apical washes; wherein each apical wash of the plurality of apical washes is followed by administering at least one light dose of the plurality of light doses up until a last apical wash of the plurality of apical washes.

In certain embodiments, at least two light doses of the plurality of light doses are administered to the surface of the human tissue model before a first apical wash of the plurality of apical washes. In certain embodiments, at least two additional light doses of the plurality of light doses are administered to the surface of the human tissue model after the first apical wash of the plurality of apical washes and before a second apical wash of the plurality of apical washes. In certain embodiments, each apical wash of the plurality of apical washes is performed at successive 24-hour intervals after the virus stock is exposed to the human tissue model. In certain embodiments, the plurality of apical washes comprise a solution that is the same as the first diluent. In certain embodiments, a first apical wash of the plurality of apical washes is performed before any light does of the plurality of light doses are administered.

In certain embodiments, the human tissue model comprises a human airway epithelia model. In certain embodiments, the virus stock comprises at least one of influenza and coronaviridae that is applied to the human airway epithelia model. In certain embodiments, a first dose of light comprises a peak wavelength in a range from 400 nanometers (nm) to 450 nm that is irradiated on the surface of the human airway epithelia model after the at least one of the influenza and the coronaviridae is removed.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 3 is a table comparing the PRNT light treatment results of FIGS. 1A-1F.

DETAILED DESCRIPTION

Figure 1A:
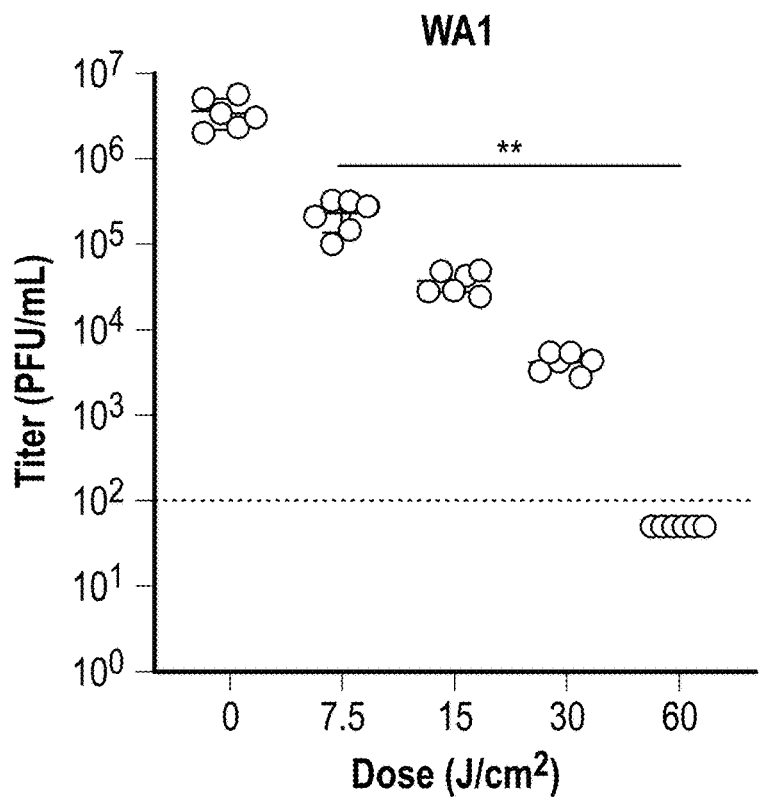
FIGS. 1A to 1H illustrate data from plaque reduction neutralization tests (PRNTs) where 425 nanometer (nm) light treatments were administered to multiple variants of SARS-CoV-2, including WA1, Alpha, Beta, Delta, Gamma, and Lambda, as well as human rhinovirus and human adenovirus.
Figure 1B:
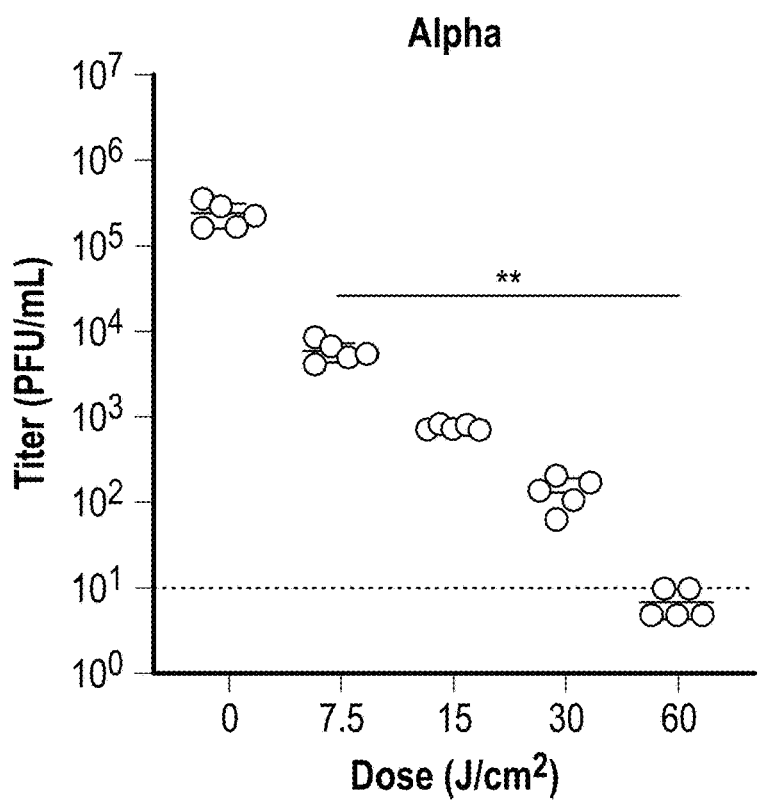
Figure 1C:
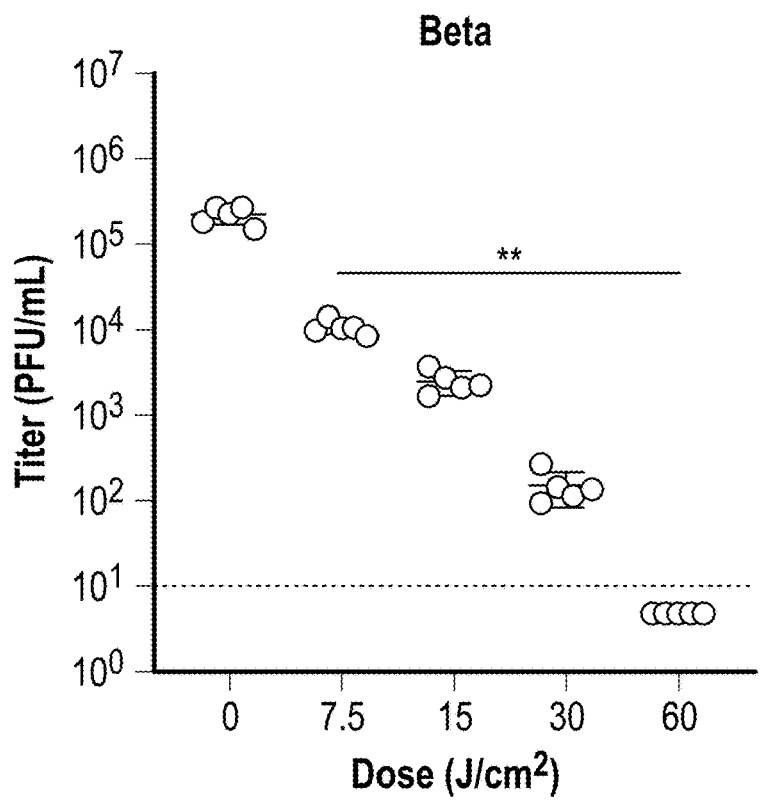
Figure 1D:
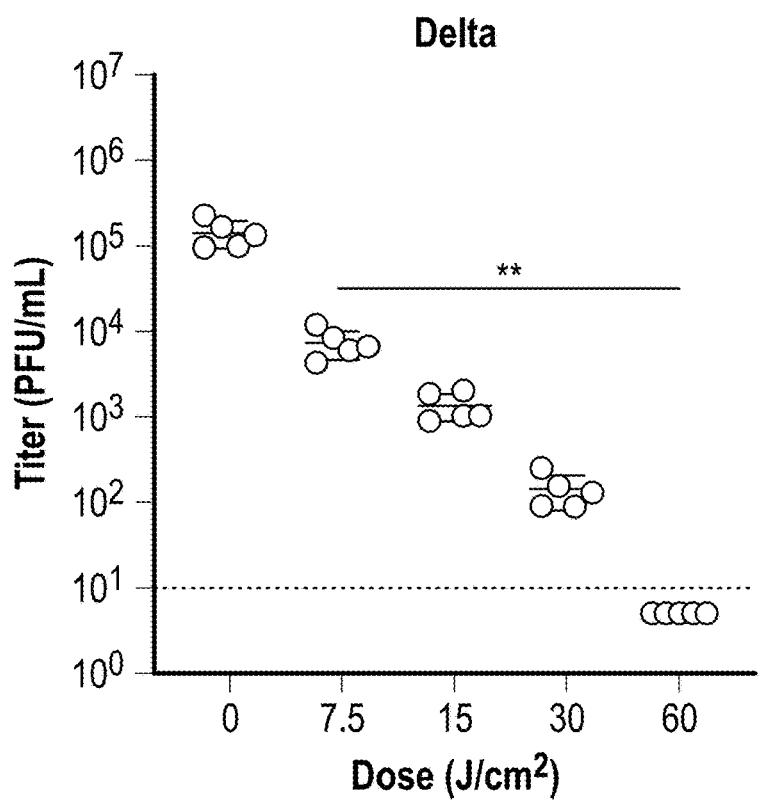
Figure 1E:
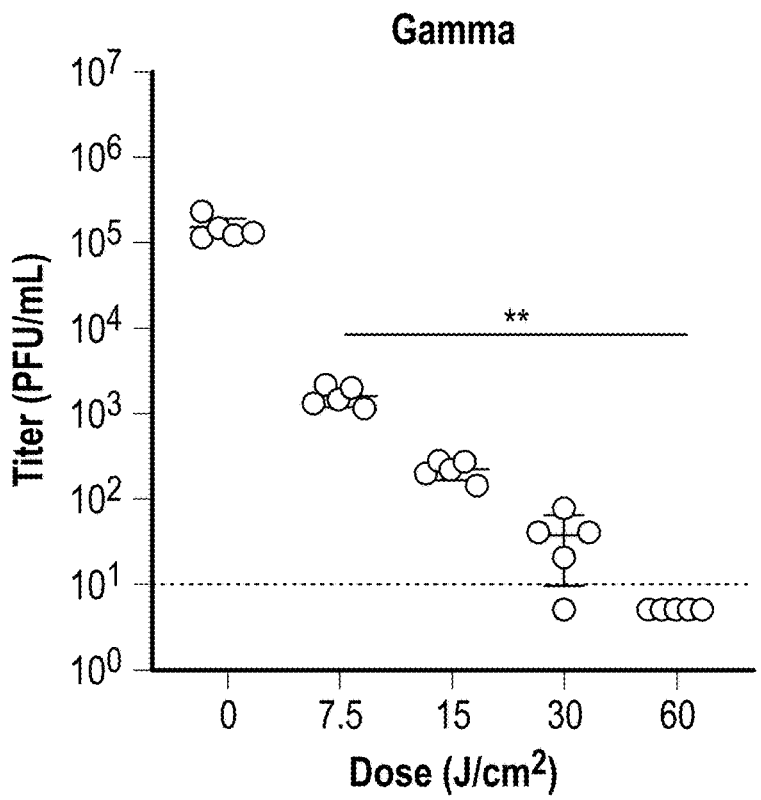
Figure 1F:
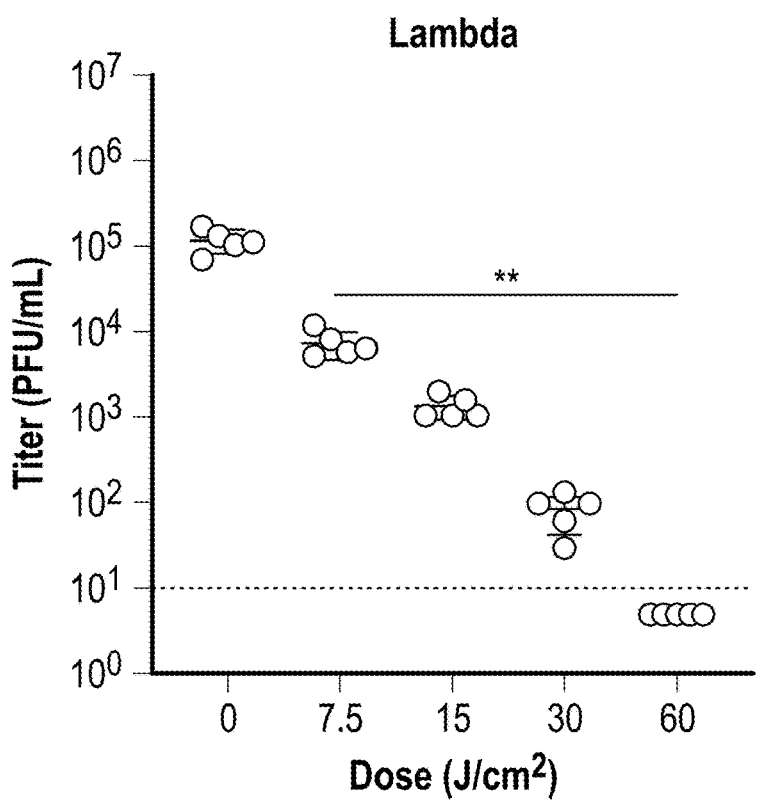
Figure 1G:
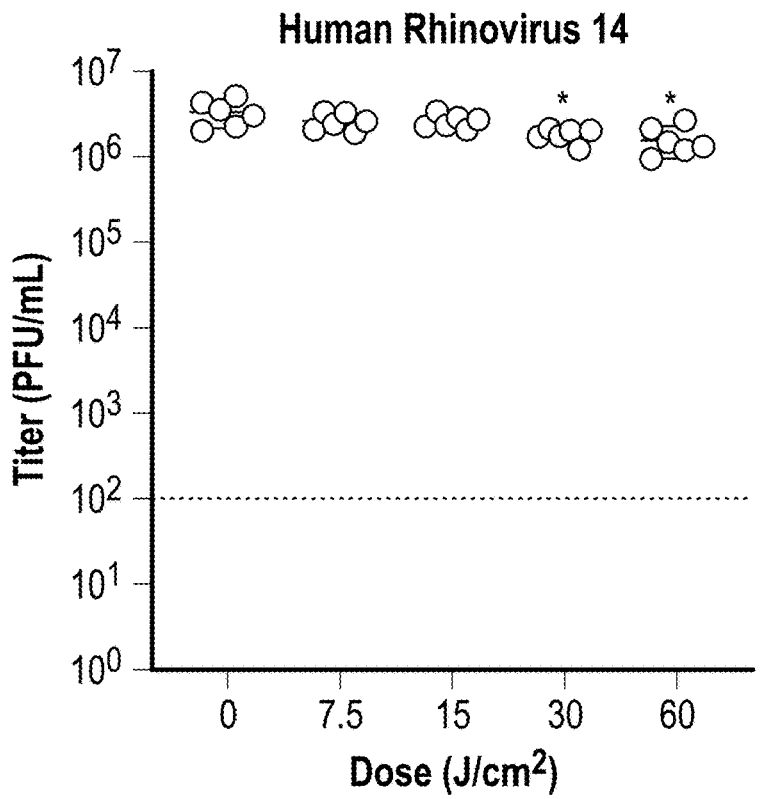

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

The present disclosure relates generally to devices and methods for impinging light on tissue to induce one or more biological effects, and more particularly to enhanced testing and characterization techniques for phototherapeutic light treatments. Such testing and characterization techniques may be particularly useful in the evaluation and development of light-based treatments for various infectious diseases, including multiple variants of SARS-CoV-2. In particular aspects, testing and characterization techniques are related to the direct testing of differentiated tissue models of human airway epithelia that have been exposed to various pathogens. Phototherapeutic light treatments and corresponding treatment protocols for light are also described that not only inactivate SARS-COV-2 variants in cell-free suspensions, but also inhibit SARS-CoV-2 infections at multiple stages of infection in tissue models of human airway epithelia in a variant-agnostic manner.

Light, or phototherapeutic light, may be administered at one or more wavelengths with one or more corresponding doses to induce one or more biological effects for recipient tissue. Biological effects may include at least one of inactivating and inhibiting growth of one or more combinations of microorganisms and pathogens, including but not limited to viruses, bacteria, fungi, and other microbes, among others. Biological effects may also include one or more of upregulating and/or downregulating a local immune response, stimulating enzymatic generation of nitric oxide to increase endogenous stores of nitric oxide, releasing nitric oxide from endogenous stores of nitric oxide, and inducing an anti-inflammatory effect. In certain aspects, light may be referred to as nitric oxide modulating light to increase concentrations of unbound nitric oxide within living tissue. Light may also be administered at one or more wavelengths as a pre-exposure prophylaxis or a post-exposure prophylaxis in order to eliminate pathogens in or on tissue of the upper respiratory tract and/or amplify host defense systems. Embodiments of the present disclosure may be used to prevent and/or treat respiratory infections and other infectious diseases.

Wavelengths of light may be selected based on at least one intended biological effect for one or more of the targeted tissues and the targeted microorganisms and/or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments include those that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Aspects of the present disclosure generally relate to devices and methods for treating, preventing, and/or reducing the biological activity of pathogens while they are in one or more areas of the upper respiratory tract and hopefully before they travel to the lungs or elsewhere in the body. In certain aspects, related devices and methods may prevent or reduce infections by reducing microbial load, decreasing the ability for penetration into cells at the site of infection, and amplifying host defense systems, all of which may minimize or avoid the need for traditional antimicrobial medicines. In further aspects, related devices and methods for light irradiation of tissues may be provided to supplement and/or enhance the effects of traditional antimicrobial medicines.

The term "phototherapy" relates to the therapeutic use of light. As used herein, phototherapy may be used to treat and/or prevent microbial infections. The mechanisms by which certain wavelengths of light are effective can vary, depending on the wavelength that is administered and the targeted microorganisms and/or pathogens. Biological effects, including antimicrobial effects, can be provided over a wide range of wavelengths, including ultraviolet (UV) ranges, visible light ranges, and infrared (IR) ranges, and combinations thereof.

The term "peak wavelength" is generally used herein to refer to the wavelength that is of the greatest radiometric power of the light emitted by a light emitter. The term "dominant wavelength" may refer to the perceived color of a spectrum, i.e., the single wavelength of light which produces a color sensation most similar to the color sensation perceived from viewing light emitted by the light source (i.e., it is roughly akin to "hue"), as opposed to "peak wavelength", which refers to the spectral line with the greatest power in the spectral power distribution of the light source. Because the human eye does not perceive all wavelengths equally (e.g., it perceives yellow and green light better than red and blue light), and because the light emitted by many solid state light emitters (e.g., LEDs) is actually a range of wavelengths, the color perceived (i.e., the dominant wavelength) is not necessarily equal to (and often differs from) the wavelength with the highest power (peak wavelength). A truly monochromatic light such as a laser may have the same dominant and peak wavelengths. For the purposes of this disclosure, unless otherwise specified herein, wavelength values are discussed as peak wavelength values.

Various wavelengths of visible light may be irradiated on human tissue with little or no impact on tissue viability. In certain embodiments, various wavelengths of visible light may elicit antimicrobial and/or anti-pathogenic behavior in tissue of the respiratory tract, including any of the aforementioned biological effects. For example, light with a peak wavelength in a range from 400 nanometers (nm) to 450 nm may inactivate microorganisms that are in a cell-free environment and/or inhibit replication of microorganisms that are in a cell-associated environment and/or stimulate enzymatic generation of nitric oxide, while also upregulating a local immune response in target tissue. In this regard, light with a peak wavelength in a range from 400 nm to 450 nm may be well suited for fighting invading viral pathogens and corresponding diseases that may originate in the respiratory tract, including Orthomyxoviridae (e.g., influenza), common colds, coronaviridae (e.g., coronavirus), picornavirus infections, tuberculosis, pneumonia, bronchitis, and sinusitis. Depending on the pathogen and corresponding disease, light with a peak wavelength in a range from 315 nm to 600 nm, or in a range from 315 nm to 500 nm, or in a range from 315 nm to 450 nm may also be used, although tissue viability could be a concern for various doses with peak wavelengths below about 400 nm. In certain embodiments, red or near-infrared (NIR) light (e.g., peak wavelength range from 600 nm to 1600 nm) may be useful to provide anti-inflammatory effects and/or to promote vasodilation. Anti-inflammatory effects may be useful in treating disorders, particularly microbial disorders that result in inflammation along the respiratory tract. In this regard, red and/or NIR light may be used as part of treatment protocols that reduce any tissue inflammation that may result from exposure to blue light, which may positively impact cell viability, thereby lowering cytotoxicity even further. A decrease in inflammation can be beneficial when treating viral infections, particularly when a virus can elicit a cytokine storm and/or inflammation can result in secondary bacterial infections. Accordingly, the combination of blue light, such as light at around 425 nm, and red light at one or more anti-inflammatory wavelengths, can provide a desirable combination of biological effects.

Depending on the application, other wavelength ranges of light may also be administered to human tissue. For example, UV light (e.g., UV-A light having a peak wavelength in a range of from 315 nm to 400 nm, UV-B light having a peak wavelength in a range of from 280 nm to 315 nm, and UV-C light having a peak wavelength in a range from 200 nm to 280 nm) may be effective for inactivating microorganisms that are in a cell-free environment and/or inhibit replication of microorganisms that are in a cell-associated environment and/or stimulate enzymatic generation of nitric oxide. However, overexposure to UV light may lead to cytotoxicity concerns in associated tissue. It may therefore be desirable to use shorter cycles and/or lower doses of UV light than corresponding treatments with only visible light.

Doses of light to induce one or more biological effects may be administered with one or more light characteristics, including peak wavelengths, radiant flux, and irradiance to target tissues. Irradiances to target tissues may be provided in a range from 0.1 milliwatts per square centimeter (mW/cm$^2$) to 200 mW/cm$^2$, or in a range from 5 mW/cm$^2$ to 200 mW/cm$^2$, or in a range from 5 mW/cm$^2$ to 100 mW/cm$^2$, or in a range from 5 mW/cm$^2$ to 60 mW/cm$^2$, or in a range from 60 mW/cm$^2$ to 100 mW/cm$^2$, or in a range from 100 mW/cm$^2$ to 200 mW/cm$^2$. Such irradiance ranges may be administered in one or more of continuous wave and pulsed configurations, including light-emitting diode (LED)-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in another range specified herein. Depending on the configuration of one or more of the light sources, the corresponding illumination device, and the distance away from a target tissue, the radiant flux value for the light source may be higher than the irradiance value at the tissue.

While certain peak wavelengths for certain target tissue types may be administered with irradiances up to 1 W/cm$^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 W/cm$^2$ to 10 W/cm$^2$ may be safely pulsed to target tissue.

Administered doses of light, or light doses, may be referred to as therapeutic doses of light in certain aspects. Doses of light may include various suitable combinations of the peak wavelength, the irradiance to the target tissue, and the exposure time period. Particular doses of light are disclosed that are tailored to provide safe and effective light for inducing one or more biological effects for various types of pathogens and corresponding tissue types. In certain aspects, the dose of light may be administered within a single time period in a continuous or a pulsed manner. In further aspects, a dose of light may be repeatably administered a number of times to provide a cumulative or total dose over a cumulative time period. By way of example, a single dose of light as disclosed herein may be provided over a single time period, such as in a range from 10 microseconds to no more than an hour, or in a range from 10 seconds to no more than an hour, while the single dose may be repeated at least twice to provide a cumulative dose over a cumulative time period, such as a 24-hour time period. In certain embodiments, doses of light are described that may be provided in a range from 0.5 joules per square centimeter (J/cm$^2$) to 100 J/cm$^2$, or in a range from 0.5 J/cm$^2$ to 50 J/cm$^2$, or in a range from 2 J/cm$^2$ to 80 J/cm$^2$, or in a range from 5 J/cm$^2$ to 50 J/cm$^2$, while corresponding cumulative doses may be provided in a range from 1 J/cm$^2$ to 1000 J/cm$^2$, or in a range from 1 J/cm$^2$ to 500 J/cm$^2$, or in a range from 1 J/cm$^2$ to 200 J/cm$^2$, or in a range from 1 J/cm$^2$ to 100 J/cm$^2$, or in a range from 4 J/cm$^2$ to 160 J/cm$^2$, or in a range from 10 J/cm$^2$ to 100 J/cm$^2$, among other disclosed ranges. In a specific example, a single dose may be administered in a range from 10 J/cm$^2$ to 20 J/cm$^2$, and the single dose may be repeated twice a day for four consecutive days to provide a cumulative dose in a range from 80 J/cm$^2$ to 160 J/cm$^2$. In another specific example, a single dose may be administered at about 30 J/cm$^2$, and the single dose may be repeated twice a day for seven consecutive days to provide a cumulative dose of 420 J/cm$^2$.

In still further aspects, light for inducing one or more biological effects may include administering different doses of light to a target tissue to induce one or more biological effects for different target pathogens. Notably, light doses as disclosed herein may provide non-systemic and durable effects to targeted tissues. Light can be applied locally and without off-target tissue effects or overall systemic effects associated with conventional drug therapies which can spread throughout the body. In this regard, phototherapy may induce a biological effect and/or response in a target tissue without triggering the same or other biological responses in other parts of the body. Phototherapy as described herein may be administered with safe and effective doses that are durable. For example, a dose may be applied for minutes at a time, one to a few times a day, and the beneficial effect of the phototherapy may continue in between treatments.

Light sources may include one or more of LEDs, organic LEDs (OLEDs), lasers and other lamps according to aspects of the present disclosure. Lasers may be used for irradiation in combination with optical fibers or other delivery mechanisms. LEDs are solid state electronic devices capable of emitting light when electrically activated. LEDs may be configured across many different targeted emission spectrum bands with high efficiency and relatively low costs. Accordingly, LEDs may be used as light sources in photonic devices for phototherapy applications. Light from an LED is administered using a device capable of delivering the requisite power to a targeted treatment area or tissue. High power LED-based devices can be employed to fulfill various spectral and power needs for a variety of different medical applications. LED-based photonic devices described herein may be configured with suitable power to provide irradiances as high as 100 mW/cm$^2$ or 200 mW/cm$^2$ in the desired wavelength range. An LED array in this device can be incorporated into an irradiation head, hand piece and/or as an external unit.

In addition to various sources of light, the principles of the present disclosure are also applicable to one or more other types of directed energy sources. As used herein, a directed energy source may include any of the various light sources previously described, and/or an energy source capable of providing one or more of heat, IR heating, resistance heating, radio waves, microwaves, soundwaves, ultrasound waves, electromagnetic interference, and electromagnetic radiation that may be directed to a target body tissue. Combinations of visual and non-visual electromagnetic radiation may include peak wavelengths in a range from 180 nm to 4000 nm. Illumination devices as disclosed herein may include a light source and another directed energy source capable of providing directed energy beyond visible and UV light. In other embodiments, the other directed energy source capable of providing directed energy beyond visible and UV light may be provided separately from illumination devices of the present disclosure.

Various therapeutics are continually being developed to counteract various respiratory diseases and infections, including influenza, common colds, coronaviridae (e.g., coronavirus), picornavirus infections, tuberculosis, pneumonia, bronchitis, and sinusitis. However, in some instances, conventional development of therapeutics may not be able to keep pace with rapid spreading and/or progressions of certain respiratory diseases and infections. For example, in late 2019, the severe acute respiratory syndrome coronavirus 2 (SARS-CoV-2), the causative agent of Coronavirus Disease 2019 (COVID-19), emerged and rapidly spread around the globe. Due to hot spots of uncontrolled spread, novel variants have emerged displaying various combinations of increased replication, increased virulence, increased transmission, and the ability to evade immune response from previous infections or vaccination. The Delta variant rapidly became the dominant global strain in 2021, unleashing increased waves of infections, hospitalizations, mortality, and economic instability. While the worst effects of the Delta variant have been in unvaccinated populations, this variant has also resulted in many breakthrough cases in vaccinated populations as well. The unabated proliferation of SARS- CoV-2, especially among unvaccinated populations, provides ample opportunities for new variants to emerge (e.g., Lambda and Mu) capable of reinfecting previously exposed patients through immune evasion and threatening the global advancements made during the ongoing pandemic.

Much effort has been placed at the development of vaccines and other therapeutics to reduce the prevalence and disease severity of SARS-CoV-2. Several vaccines derived from the original, parental strain have been developed and distributed worldwide with promising effects on the global disease burden. Despite the rapid development of successful and deployable vaccines, only fractions of the worldwide population are fully vaccinated and recent studies have suggested waning protection in the vaccinated population. Further, therapeutic development has lagged; several approaches have shown promise in laboratory or small-scale clinical studies with the best success in early onset disease and via a combination of therapeutic modalities. Two therapeutics that are currently in use for the treatment of COVID-19 are therapeutic monoclonal antibodies and remdesivir. Each of these approaches come with their own limitations, including intravenous infusions, cost, susceptibility to variant escape, and limited utility outside of inpatient settings. These limitations highlight a critical need for therapeutics in the fight against COVID-19, particularly for a variant-agnostic countermeasure that can be easily administered in the home setting for mild-to-moderate cases of COVID-19.

Visible light has been investigated as a tool to inactivate SARS-CoV-2 on surfaces and environments to help curtail aerosol or fomite spread. However, light therapy has also shown the potential as an efficacious and easy-to-administer treatment that reduces viral shedding and provides symptomatic relief in vivo. It has previously been reported that certain wavelength ranges of light, including those with 425 nm-emitting LED arrays, or light with a peak wavelength in a range from 400 nm to 450 nm, is effective for inactivating initial variants of SARS-CoV-2 in cell-free and cell-associated formats. It has also been demonstrated that such wavelengths of light are well-tolerated by a human tracheobronchial tissue model and may induce host interleukins IL-1a and IL-1B in a human buccal tissue model. Additionally, it has been demonstrated that human airway models can tolerate up to 256 $J/cm^2$ of 425 nm light given in a twice daily 32 $J/cm^2$ regimen for four days.

According to aspects of the present disclosure, improved testing and characterization techniques for phototherapeutic light treatments are described. Such testing and characterization techniques may be particularly useful in the evaluation of light-based treatments for various infectious diseases, including multiple variants of SARS-CoV-2. In particular aspects, testing and characterization techniques are related to testing of differentiated models of human airway epithelia. As a starting point, experimental results are presented for plaque reduction neutralization tests (PRNT) that demonstrate the effectiveness of 425 nm light in consistently inactivating each of the known major SARS-CoV-2 variants. In order to validate the effectiveness of such results in an environment that more closely mimics diseases in the respiratory tract, testing and characterization techniques are disclosed herein that validate the PRNT findings in translationally relevant three-dimensional, differentiated models of human tracheobronchial epithelia.

Figure 1H:
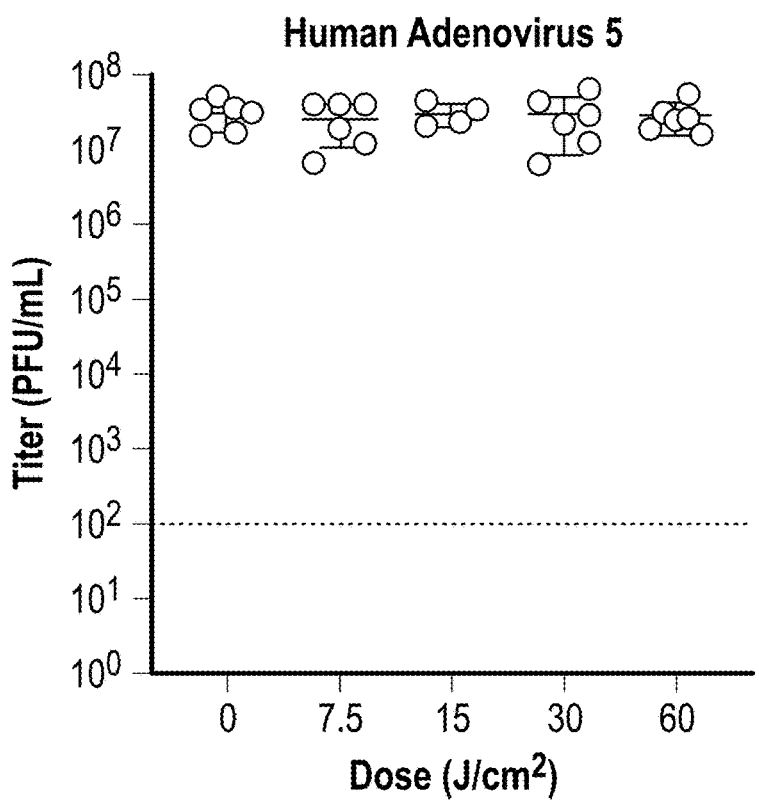

FIGS. 1A to 1J illustrate a comparison of PRNT results for 425 nm light treatments for multiple variants of SARS-CoV-2. The PRNT results were collected for a panel of SARS-CoV-2 variants including WA1 (FIG. 1A), Alpha (FIG. 2B), Beta (FIG. 1C), Delta (FIG. 1D), Gamma (FIG. 1E), and Lambda (FIG. 1F) as well as human rhinovirus 14 (FIG. 1G) and human adenovirus 5 (FIG. 1H). Biological light units were adapted to evenly distribute light over an entire surface area of a 24-well plate and used to evaluate various energy densities in the classic PRNT assay method to measure inactivation of cell-free SARS-CoV-2 variants. The SARS-CoV-2 samples were diluted and illuminated with varying doses of 425 nm light prior to infectious titer enumeration with plaque assay. As illustrated, the 425 nm light treatment reduced SARS-CoV-2 infectious titers in a dose-dependent manner: >1 $\log_{10}$ at 7.5 $J/cm^2$, >2 $\log_{10}$ at 15 $J/cm^2$, >3 $\log_{10}$ at 30 $J/cm^2$, and >4 $\log_{10}$ at 60 $J/cm^2$. However, the same doses did not inactivate the non-enveloped RNA virus human rhinovirus 14 (FIG. 1G) indicating an envelope-dependent mechanism of inactivation and preservation of viral RNA. Similarly, no inactivation of the non-enveloped DNA virus human adenovirus 5 (FIG. 1H) was demonstrated, indicating that these doses of 425 nm light may not be damaging to DNA. In this manner, FIGS. 1A to 1F demonstrate inactivation of a panel of SARS-CoV-2, including those with mutations that are associated with immune evasion. Accordingly, such mutations may not convey viral resistance to light therapies as described herein.

Figure 1I:
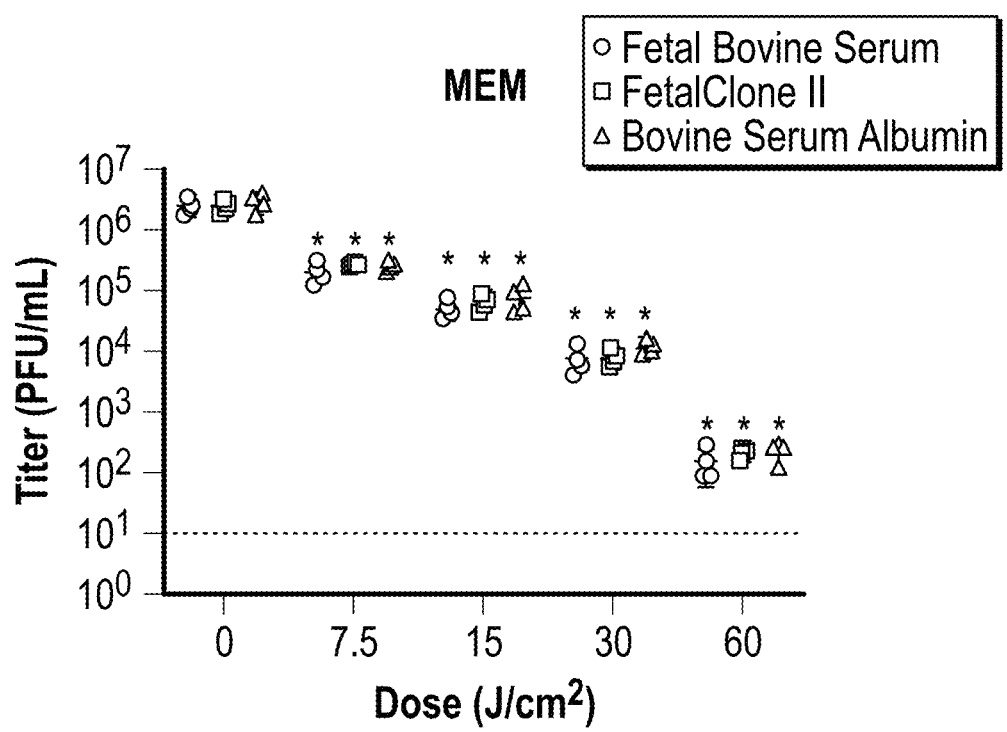
FIGS. 1I to 1J illustrate data from PRNT assays where 425 nm light treatments were applied to SARS-CoV-2 Beta in different compositions of basal media and with various serum supplementations.
Figure 1J:
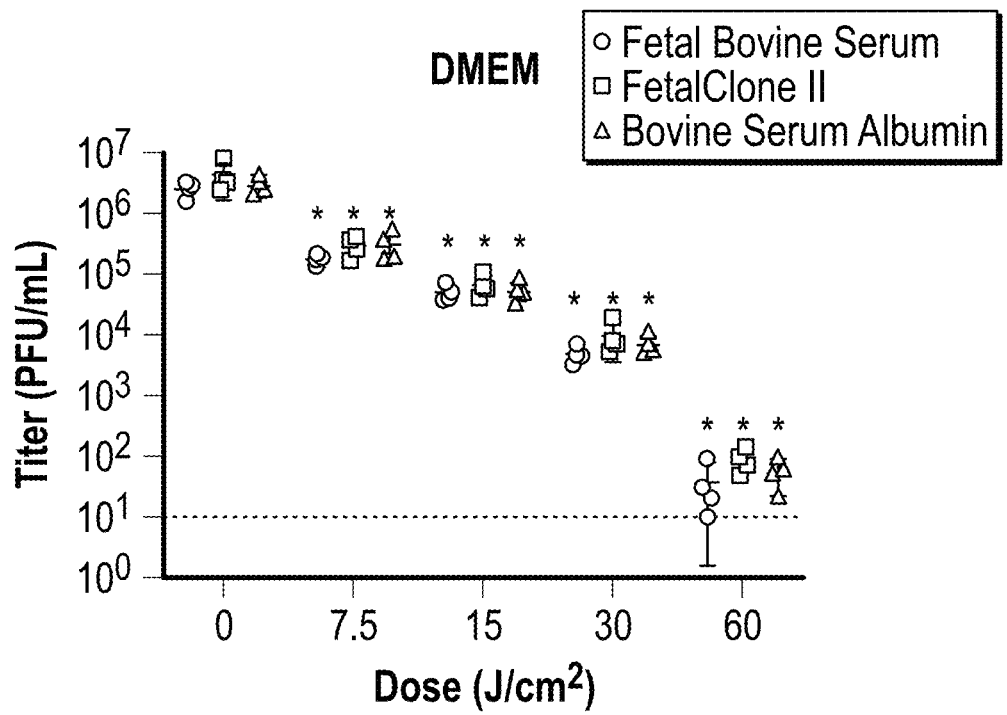

In order to evaluate any potential influence of a basal media type, PRNT assays were repeated for the Beta variant of SARS-CoV-2 for different basal media types and different serum supplementations. FIG. 1I illustrates data from a PRNT assay where 425 nm light treatments were applied to SARS-CoV-2 Beta in a minimum essential medium (MEM) with various serum supplementations of Fetal Bovine Serum, FetalClone II, and Bovine Serum Albumin. FIG. 1J illustrates data for a similar PRNT assay as FIG. 1I, but with Dulbecco's modified Eagle's medium (DMEM). The results of FIGS. 1I and 1J, in a similar manner with FIG. 1C for SARS-CoV-2 Beta, demonstrate no difference in impact of media type, indicating the effectiveness of 425 nm light may not be related to any potential photosynthesizer action of the media itself. In this regard, 425 light may provide direct inactivation of SARS-CoV-2 virion independent of potential differences in media composition such as increased amino acids or lot-specific serum factors.

Figure 2:
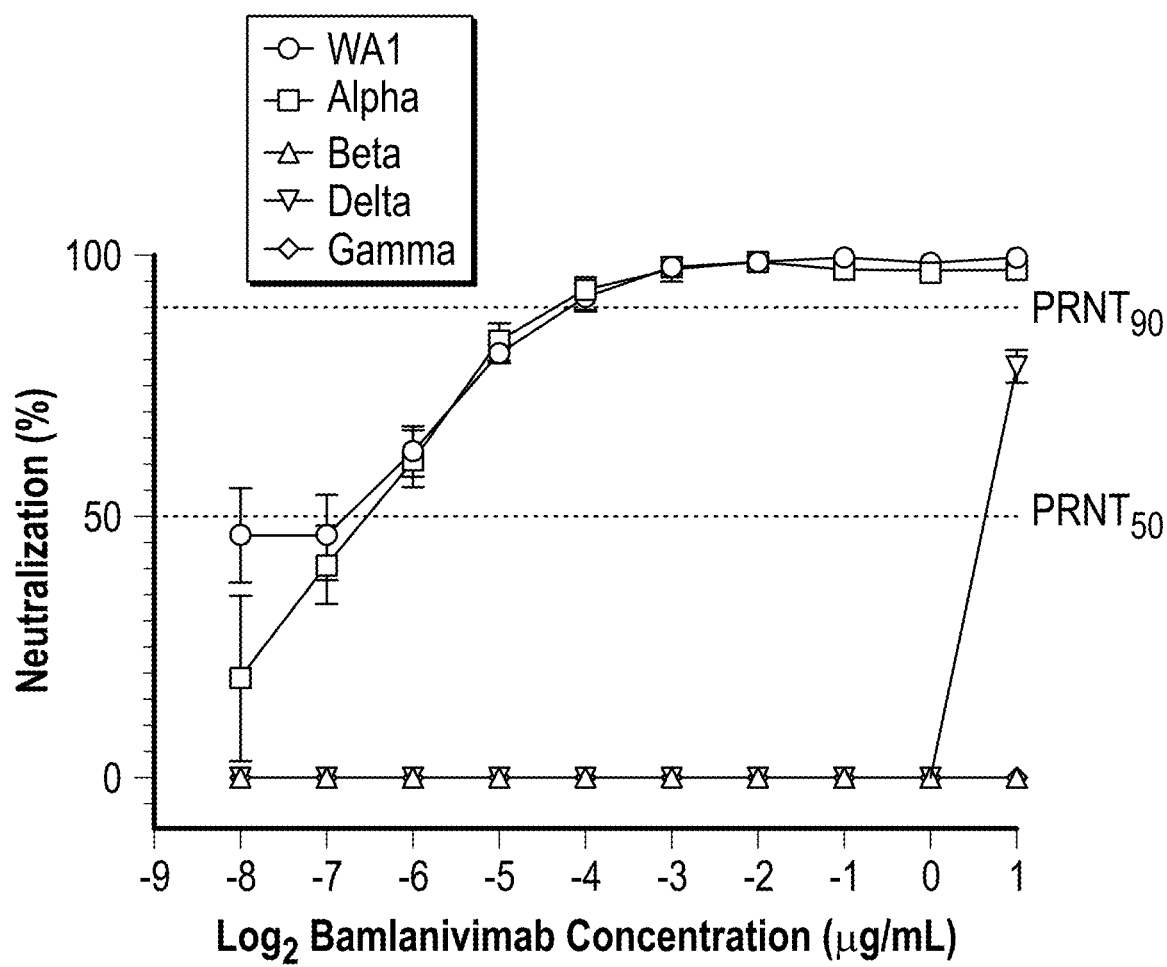
FIG. 2 illustrates data from PRNT assays that are similar to FIGS. 1A to 1J, but where therapeutic monoclonal antibody treatments were implemented instead of 425 nm light treatments for multiple variants of SARS-CoV-2.

FIG. 2 illustrates data from PRNT assays that are similar to FIGS. 1A to 1J, but where therapeutic monoclonal antibody treatments were implemented instead of 425 nm light treatments for multiple variants of SARS-CoV-2. For the date of FIG. 2, the PRNT assays for SARS-CoV-2 WA1, Alpha, Beta, Delta, and Gamma variants were incubated with bamlanivimab. Notably, bamlanivimab is a monoclonal antibody treatment that was developed for original strains of SARS-CoV-2, such as SARS-CoV-2 WA1. As illustrated, the effectiveness of bamlanivimab is specific to SARS-CoV-2 WA1 and SARS-CoV-2 Alpha, while later variants are capable of evading such therapeutic monoclonal antibody treatments.

FIG. 3 is a table comparing the PRNT light treatment results of FIGS. 1A-1F. As illustrated, the $PRNT_{50}$ and $PRNT_{90}$ titers for doses of 425 nm light for Alpha, Beta, Delta, Gamma, or Lambda variants were below the dose required to inactivate the parental WA1 strain, indicating that SARS-CoV-2 variants do not escape 425 nm light inactivation. In contrast, with each progressing variant, initial monoclonal antibody treatments lose effectiveness.

Figure 4A:
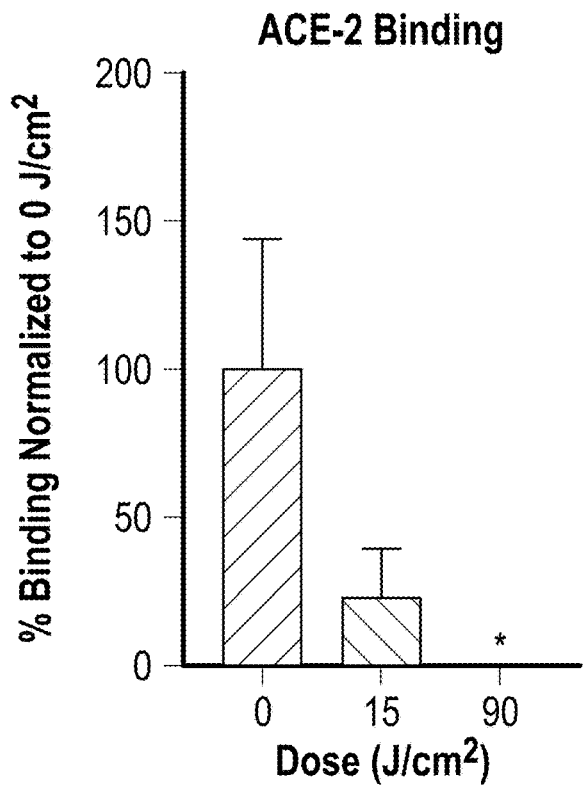
FIGS. 4A to 4I represent testing data that was performed to investigate the mechanism of 425 nm light inactivation of cell-free SARS-CoV-2 with regard to angiotensin-converting enzyme 2 (ACE-2) binding and cell-associated SARS-CoV-2 RNA.

FIGS. 4A to 4I represent testing data that was performed to investigate the mechanism of 425 nm light inactivation of cell-free SARS-CoV-2. For the testing, cell-free SARS-CoV-2 Beta was illuminated with two different doses (i.e., 15 $J/cm^2$ or 90 $J/cm^2$) of 425 nm light and its ability to bind angiotensin-converting enzyme 2 (ACE-2) and enter host cells was assessed. FIG. 4A represents a human ACE-2 receptor-ligand binding assay performed to determine if illuminated SARS-CoV-2 Beta maintained ACE-2 binding integrity.

Figure 4B:
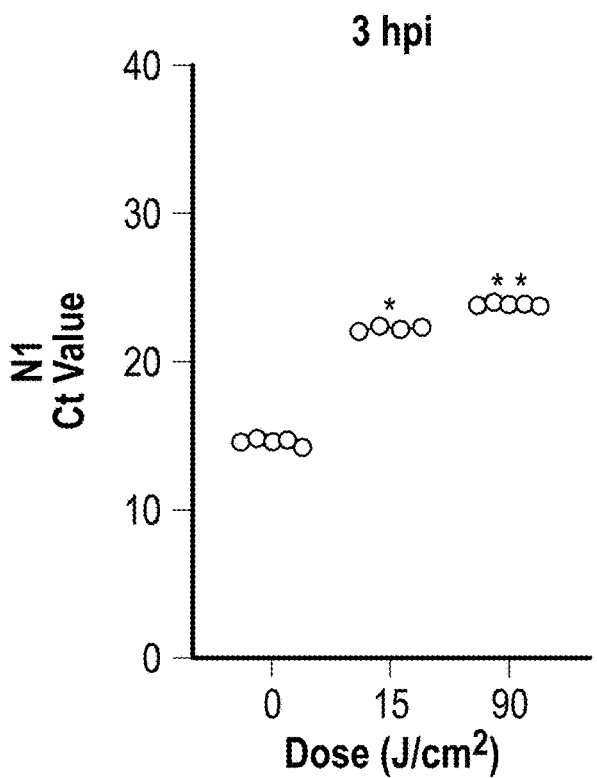
Figure 4C:
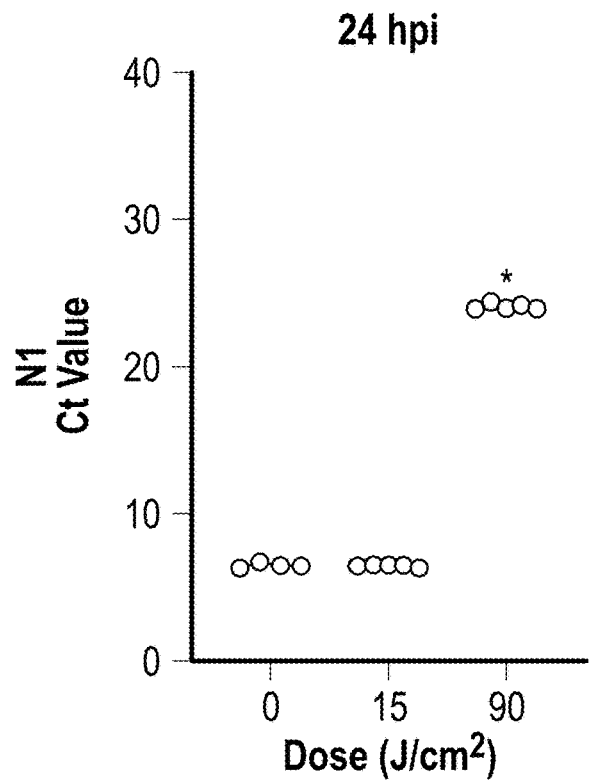
Figure 4D:
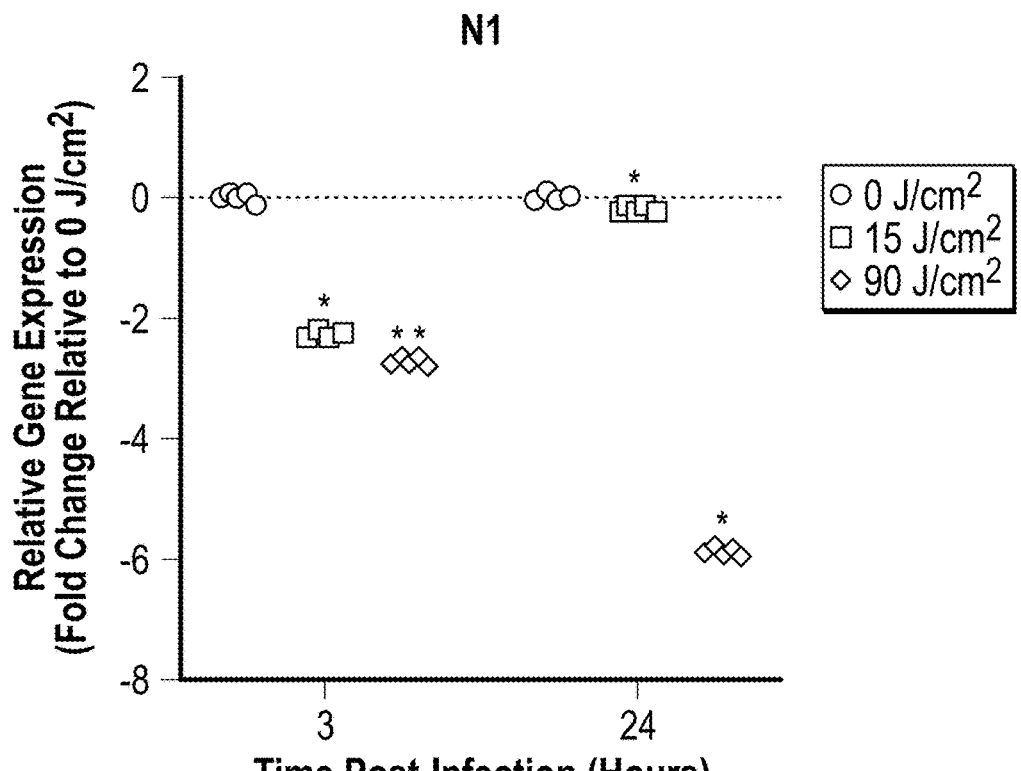
Figure 4E:
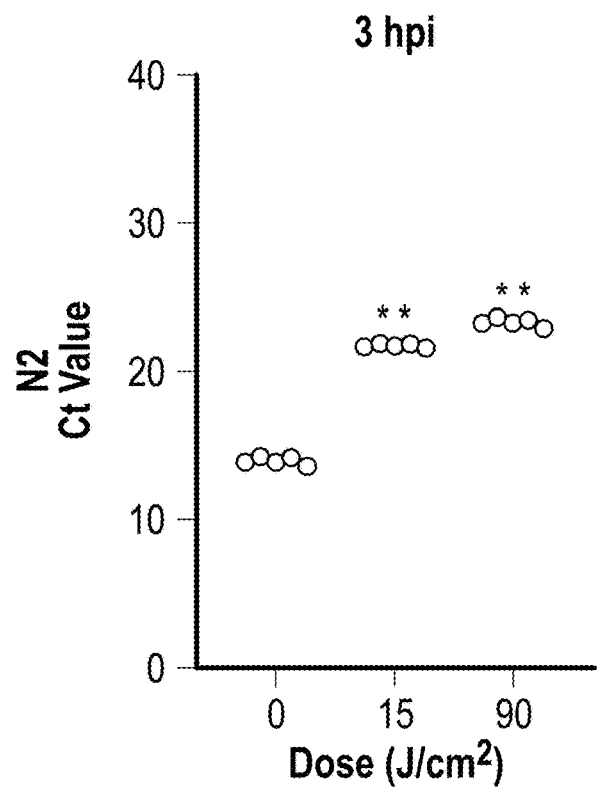
Figure 4F:
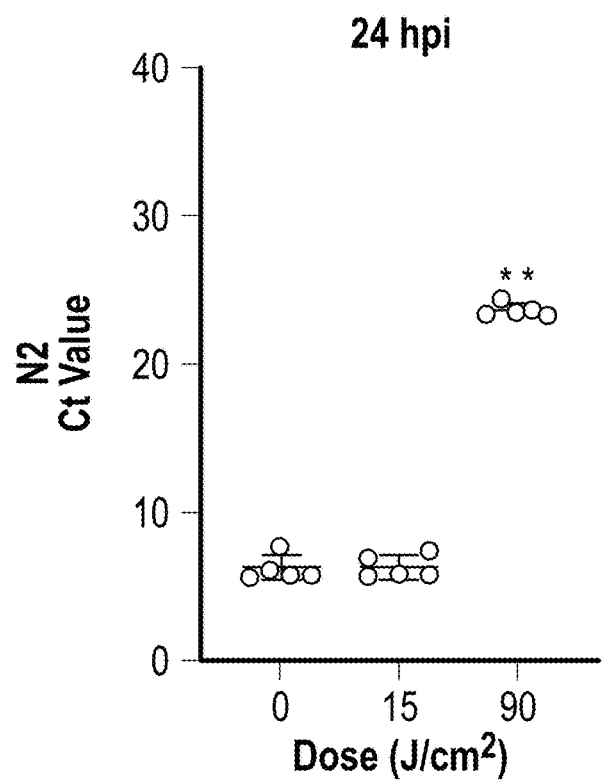
Figure 4G:
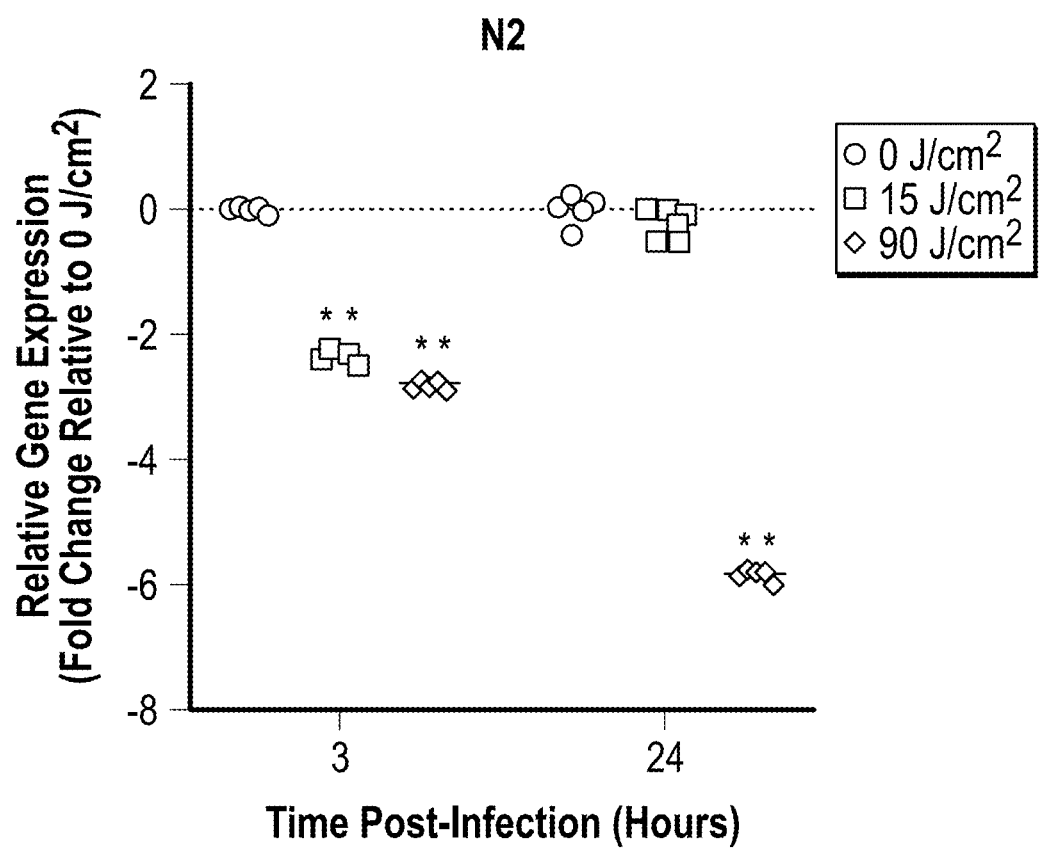
Figure 4H:
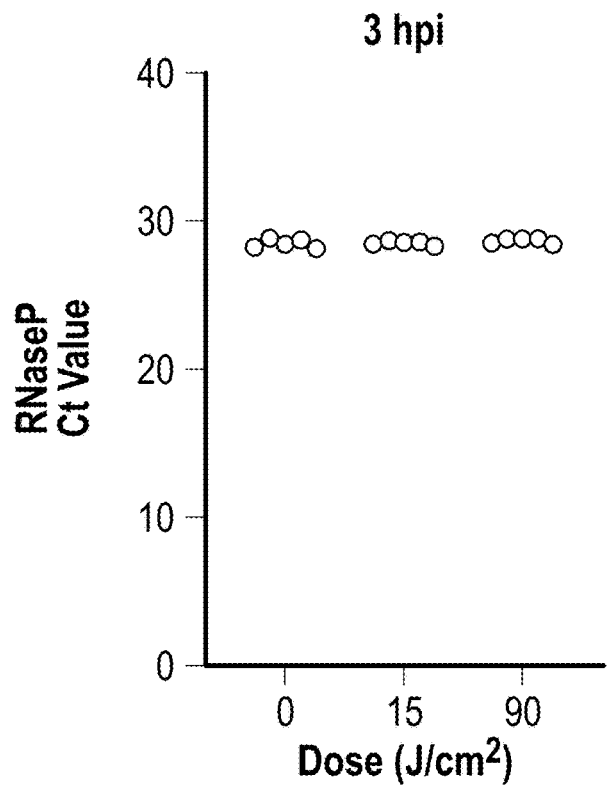
Figure 4I:
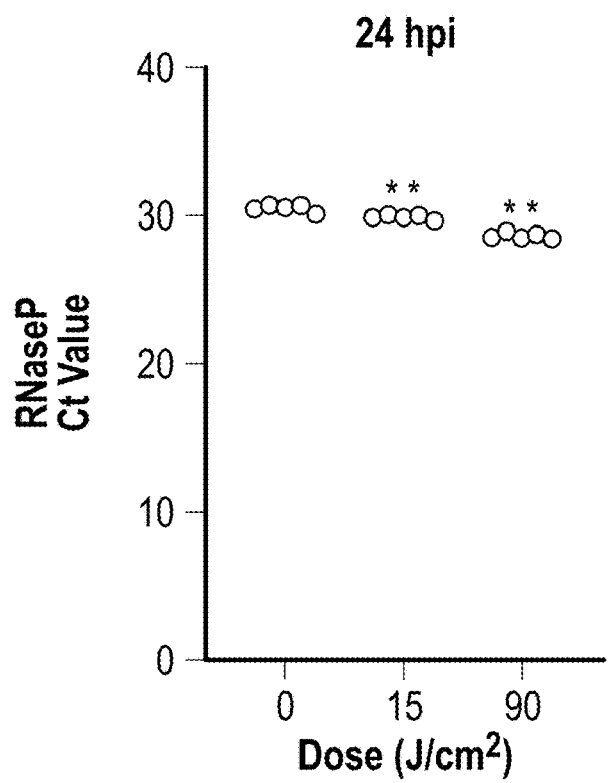

The doses were selected as a generally non-virucidal dose of 15 J/cm$^2$ and a virucidal dose of 90 J/cm$^2$ to ensure complete inactivation for these assays. As illustrated, Illumination with 425 nm light reduced SARS-CoV-2 Beta binding to ACE-2 in a dose-dependent manner, as 15 J/cm$^2$ reduced binding by about 80% and 90 J/cm$^2$, a dose to ensure full inactivation, eliminated all ACE-2 binding. Statistical significance was determined with the Mann-Whitney ranked sum test and is indicated by * ($p \leq 0.05$). Using the same light doses, Vero E6 cells were inoculated with light-treated virus and cell-associated SARS-CoV-2 RNA at 3 hours post infection (hpi) as illustrated in FIG. 4B and at 24 hpi as illustrated in FIG. 4C was evaluated. Results were determined for total RNA extracted from inoculated cultures by N1 qRT-PCR analysis. At 3 hpi, both doses significantly reduced detectable viral RNA compared to the unilluminated control as illustrated by increases in cycle threshold (Ct), which is inversely proportional to viral RNA. However, at 24 hpi, viral RNA from 15 J/cm$^2$ had similar amounts of viral RNA as cells inoculated with unilluminated virus suspensions. Conversely, SARS-CoV-2 illuminated with 90 J/cm$^2$ of 425 nm light had significantly lower amounts of detectable viral RNA and did not change significantly from 3 hpi to 24 hpi, suggesting impaired viral entry into the host cell following inactivation. FIG. 4D represents gene expression normalized to host RNaseP for confirmation of the results of FIGS. 4B and 4C where detectable RNA reduced by 2 logs for the 15 J/cm$^2$ dose at 3 hpi and reduced by 2 logs and 6 logs at 3 hpi and 24 hpi, respectively for the 90 J/cm$^2$ dose. Similar trends were observed with the N2 qRT-PCR as illustrated in FIGS. 4E to 4G, but a dose dependent effect was not observed in RNaseP as illustrated in FIGS. 4H and 4I. In this regard, the 425 nm light may inactivate SARS-CoV-2 by inhibiting viral binding and entry to the host cell.

While the previous testing results are provided for cell-free associations, enhanced testing and characterization techniques for phototherapeutic light treatments in primary human tissue models is disclosed herein. In various aspects, human tissue models, such as well-differentiated models of the human large airway epithelia, are infected with viruses and phototherapeutic light treatments are subsequently applied. Various harvesting techniques are also disclosed that are unique to phototherapeutic light testing. In this regard, phototherapeutic light treatment protocols may be rapidly developed and refined by implementation of such testing techniques in human tissue models in order to keep up with ever changing challenges of proliferating infectious diseases.

Figure 5:
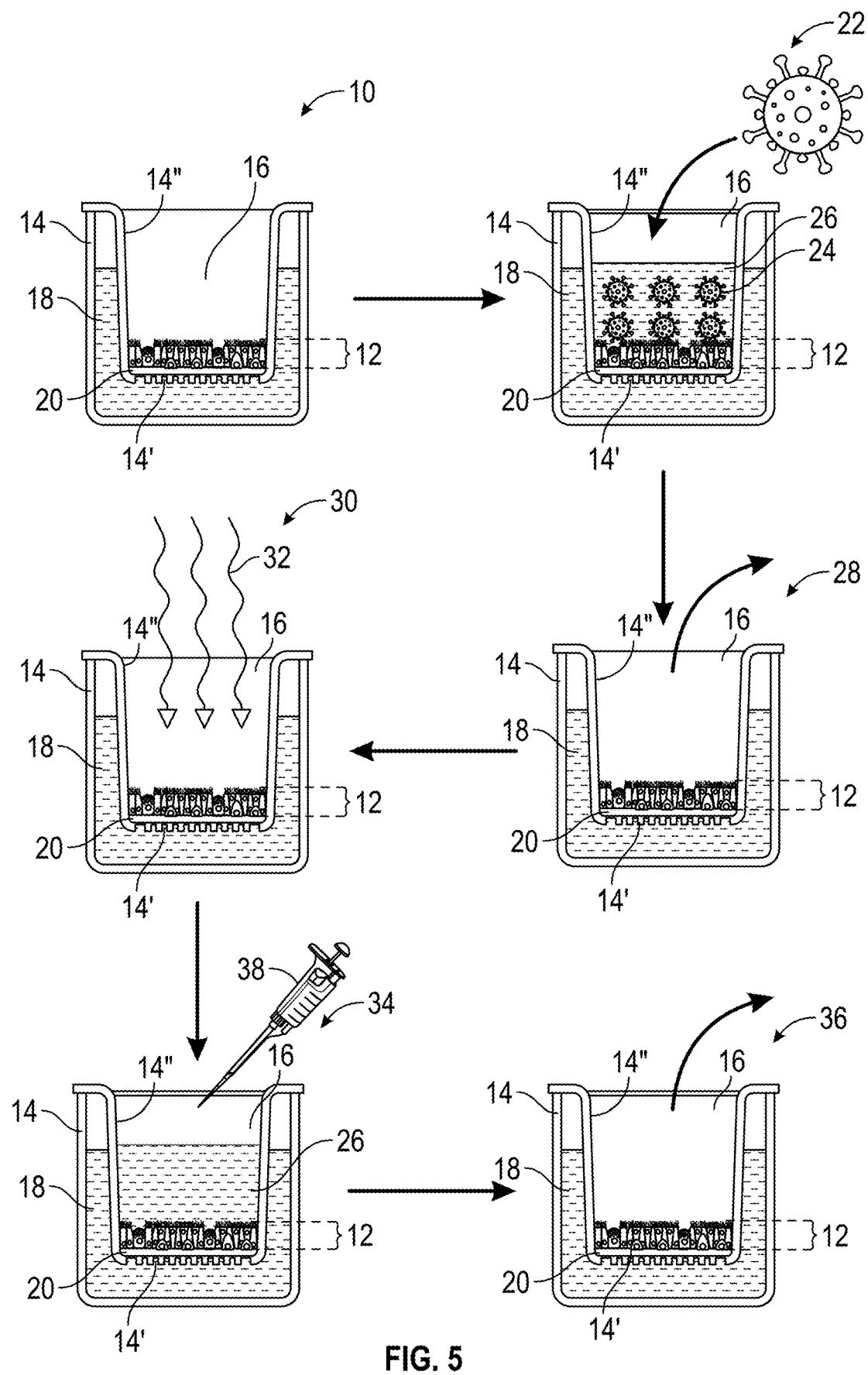
FIG. 5 is a generalized process flow for a testing and characterization technique for phototherapeutic light treatments of primary human tissue models according to principles of the present disclosure.

FIG. 5 is a generalized process flow for a testing and characterization technique for phototherapeutic light treatments of primary human tissue models. In a first step 10, a primary human tissue model 12, such as a tissue model derived from large airway epithelial cells of a human donor, is placed within a container 14. The container may form a hollow opening 16 in which the human tissue model 12 resides. The container 14 may include a double-walled structure that houses a media 18, or a basolateral media, that is provided on a bottom side of the human tissue model 12, for example by way of one or more openings 14' in an inner wall 14" of the container 14 that are underneath the human tissue model 12. In this manner, the media 18 may be applied to the bottom side of the human tissue model 12 while an opposing top side of the human tissue model 12 is exposed to air within the opening 16, thereby mimicking epithelial tissue, such as within the respiratory tract. In certain embodiments, a porous membrane 20, such as a collagen membrane, may be placed between the human tissue model and the one or more openings 14' of the inner wall 14". In practice, the container 14 may comprise a transwell insert or a millicell insert without deviating from the principles disclosed.

In a second step 22, a virus stock 24 in a diluent 26 is applied to the top side of the human tissue model 12 within the opening 16 by way of a pipette, or other dispensing tool. In certain embodiments, the diluent 26 may be a similar or even a same material or solution as the media 18. In certain embodiments, the diluent 26 may comprise a MEM with a small percentage (e.g., 2%) of fetal bovine serum additive to provide a low protein environment and a small percentage (e.g., 1%) of antibiotic-antimycotic. The virus stock 24 and diluent 26 may be left in contact with the human tissue model 12 for a period of time to promote incubation, such as 1 to 3 hours, before advancement to a third step 28. In the third step 28, the virus stock 24 and diluent 26 are removed from the human tissue model 12.

In a fourth step 30, a dose of light 32 may be applied to the human tissue model 12 through the opening 16. In certain embodiments, a time delay may be provided after removal of the virus stock 24 and diluent 26 of the third step 28 and the light treatment of the fourth step 30. By way of example, the time delay may be in a range of about 30 minutes to about 90 minutes, or about 1 hour. At any time period thereafter, a viral load in the human tissue model 12 may be quantified by a harvesting sequence as illustrated in a fifth step 34 and sixth step 36. In the fifth step 34, diluent 26 that is free of the virus stock 24 may be added back to the human tissue model 12 by way of a pipette 38 or the like. The diluent 26 may be left in contact with the human tissue model 12 for a period of time before it is removed in the sixth step 36. In this regard, the harvesting steps of the fifth and sixth steps 34, 36 in essence performs an apical wash of the human tissue model 12 that collects any virus shedding from the human tissue model 12. In this manner, a quantity of a viral load within the apical wash removed from the human tissue model 12 may be enumerated via plaque assay and this quantity may be correlated to a viral load in the human tissue model 12. Notably, the diluent 26 in the fifth step 34 comprises a same solution or composition of materials as the diluent 26 used in the second step 22. By using a same type of the diluent 26 in the fifth step 34 as in the second step 22, the apical wash procedure may be performed with reduced stress on the human tissue model 12 and without impacting a chemistry of the human tissue model 12.

In certain embodiments, the process flow of the fourth step 30 through the sixth step 36 may be repeated on the same human tissue model 12 to evaluate the effectiveness for reducing viral loads of multiple doses of the light 32 at various time intervals post infection from the second step 22. Importantly, the harvesting steps of the fifth and sixth steps 34, 36 may be performed immediately prior to any subsequent light treatment according to the third fourth step 30 in order to accurately quantify viral loads from the previous light treatment. This sequence may be repeated up to a last harvesting step (e.g., apical wash and plaque assay) that is performed at a time period after a last dose of the light 32.

In a particular example, the above-described process flow may be well suited for applications where the human tissue model 12 comprises a human airway epithelia model and the virus stock 24 comprises at least one of influenza and coronaviridae. In such examples, the light 32 may be administered with a peak wavelength in a range from 400 nm to 450 nm, and the dose may be in a range from 0.5 J/cm$^2$ to 100 J/cm$^2$. In other examples, any of the previously described wavelength ranges and doses may be implemented, depending on the nature of the testing and characterization.

Figure 6:
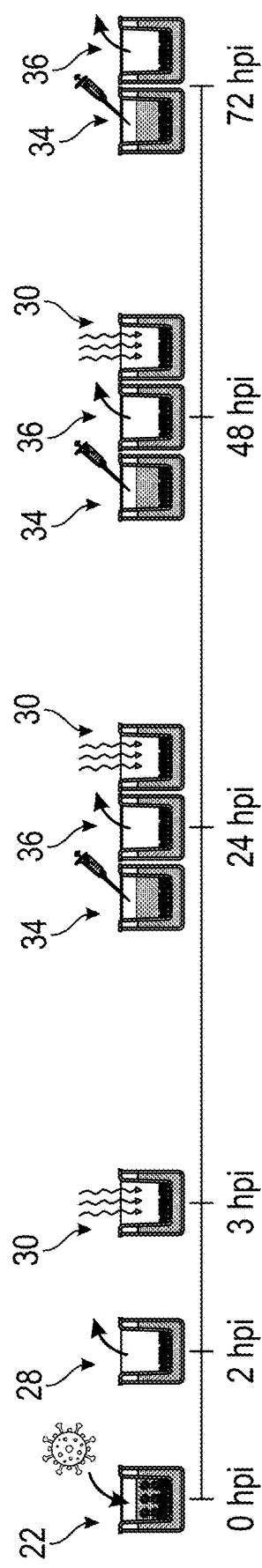
FIG. 6 is a process flow for testing and characterization of phototherapeutic light treatments in primary human tissue models as described for FIG. 5 for once daily light treatments after infection.
Figure 7:
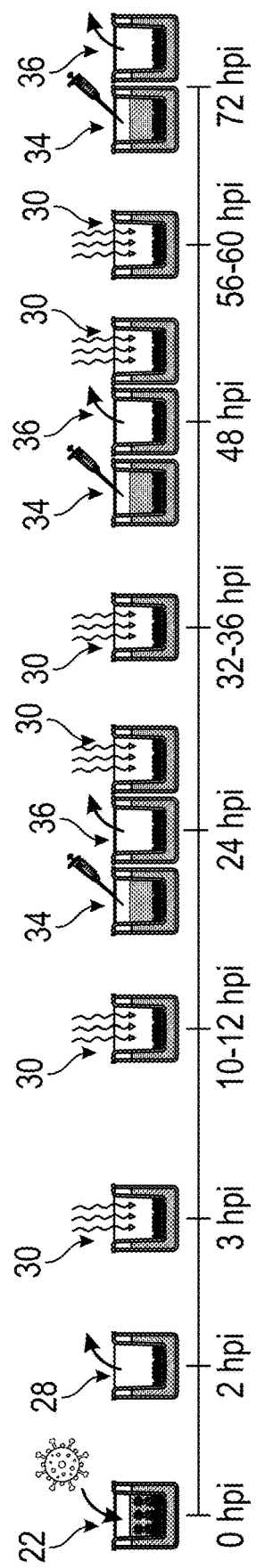
FIG. 7 is a process flow for testing and characterization of phototherapeutic light treatments in primary human tissue models that is similar to FIG. 6 but modified for twice daily light treatments after infection.

FIGS. 6 and 7 illustrate certain testing sequences where various steps as illustrated in FIG. 5 are repeated at particular time intervals post infection. In this regard, FIGS. 6 and 7 are provided as exemplary sequences for the testing and characterization for the effectiveness of light-based treatments in the reduction of viral loads in human tissue models. FIGS. 6 and 7 represent two of many different testing sequences that may be performed according to the different steps described in FIG. 5.

FIG. 6 is a process flow for testing and characterization of phototherapeutic light treatments in primary human tissue models as described for FIG. 5 for once daily light treatments after infection. As illustrated, the second step 22 of infection of the tissue model is labeled as 0 hours-post-infection (hpi). At a first time interval (e.g., at 2 hpi in FIG. 6), the third step 28 of removing the virus stock and diluent is performed. During the first time interval when the virus stock and diluent are in contact with the human tissue model, viral incubation is promoted at a constant temperature (e.g., about 37° C.) in an environment of about 5% carbon dioxide ($CO_2$). After a second time interval, (e.g., at 3 hpi), the fourth step 30 of applying a dose of light to the tissue is performed. While a 1-hour differential between the third step 28 and the fourth step 30 is illustrated, the time difference could be other values, such as in a range from 30 minutes to 12 hours, or in a range from 30 minutes to 6 hours, or in a range from 30 minutes to 90 minutes. In certain embodiments, the viral load may be characterized in the human tissue model at various intervals thereafter. In FIG. 6, the harvesting sequence of the fifth step 36 and sixth step 38 is performed in daily intervals post infection (e.g., 24 hpi, 48 hpi, and 72 hpi). Notably, after each harvesting sequence, another light treatment according to the fourth step 30 may be performed.

FIG. 7 is a process flow for testing and characterization of phototherapeutic light treatments in primary human tissue models that is similar to FIG. 6 but modified for twice daily light treatments after infection. In this regard, a second light treatment according to the fourth step 30 may be performed each day. In certain embodiments, the second light treatments each day may be administered at approximately half-day intervals from the other light treatments, such as at 10-12 hpi, 32-36 hpi, and 56-60 hpi.

Figure 8A:
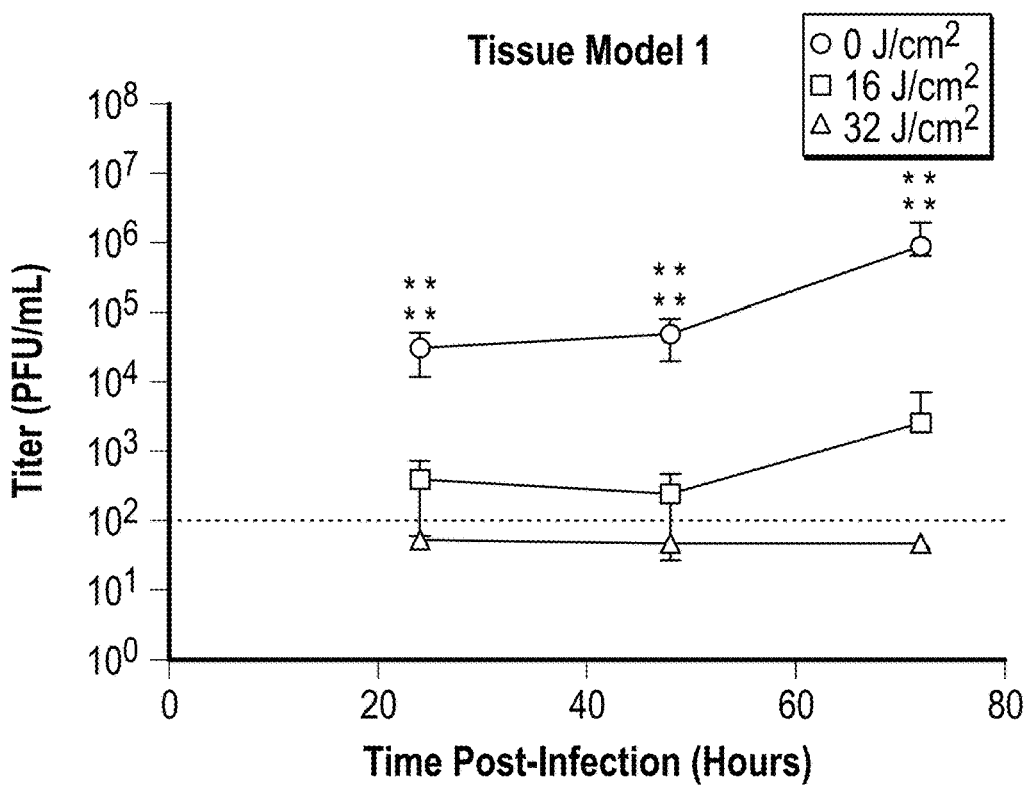
FIGS. 8A and 8B represent an exemplary therapeutic efficacy study where plaque assays were performed on two different human tissue models infected with SARS-CoV-2 WA1 with once daily light treatments.
Figure 8B:
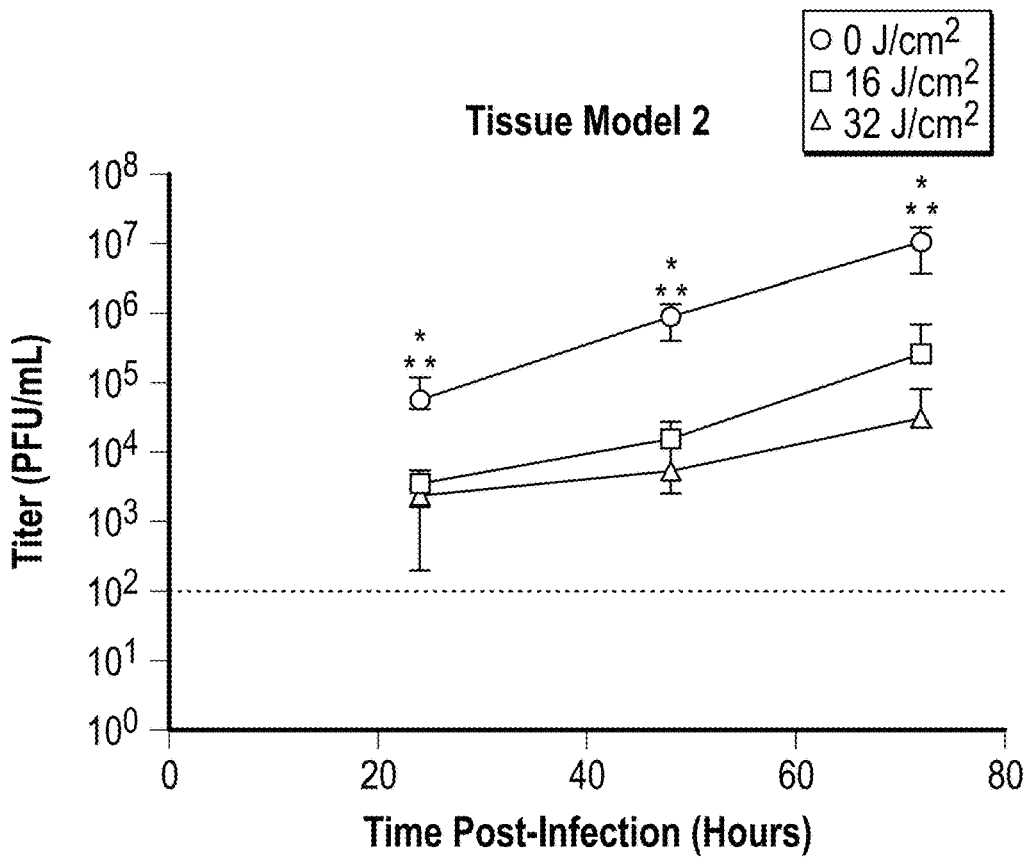

The testing and characterization principles of the present disclosure as described in FIGS. 5 to 7 may be well suited to evaluate the effectiveness of light treatments for reducing viral loads of any number of infectious diseases in human tissue models. In certain embodiments, evaluation of viral replication in different types of human tissue models may be performed to assist in the selection of a suitable human tissue model for a particular experiment. For example, FIGS. 8A and 8B represent an exemplary therapeutic efficacy study where plaque assays were performed on two human tissue models infected with SARS-CoV-2 WA1 with once daily 425 nm light treatments at doses of 16 J/cm$^2$, 32 J/cm$^2$, and a control population that did not receive a light treatment (i.e., 0 J/cm$^2$). As illustrated, single daily doses of 16 J/cm$^2$ and 32 J/cm$^2$ 425 nm light significantly reduced SARS-CoV-2 WA1 titers through 72 hpi in both tissue models, though the reductions in the Tissue Model 1 of FIG. 8A appeared greater. However, consistent replication kinetics and higher peak titers were observed with the Tissue Model 2 of FIG. 8B, providing a more robust and stringent model for 425 nm efficacy and safety evaluation. In this manner, the Tissue Model 2 of FIG. 8B was utilized for all SARS-CoV-2 variant infection experiments described below.

Figure 9A:
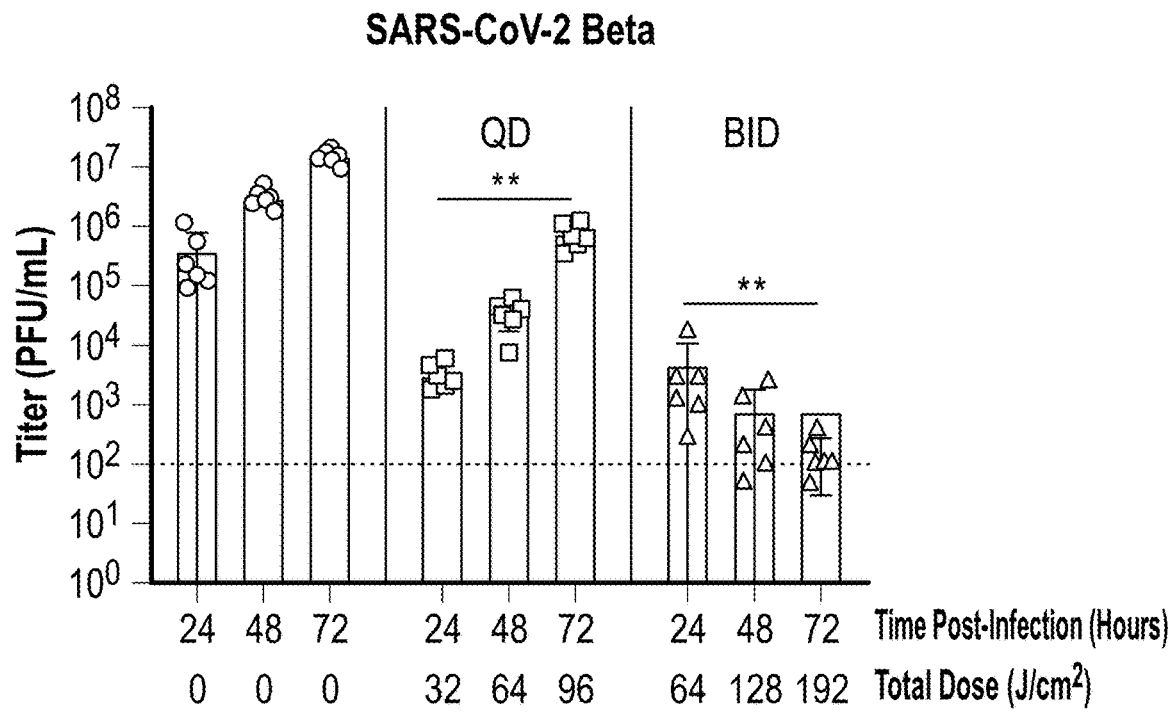
FIG. 9A is a comparison chart summarizing an experiment to evaluate the testing and characterization protocols described in FIGS. 6 and 7 in the context of 425 nm light for reducing viral loads of SARS-CoV-2 Beta in human tissue models.

FIG. 9A is a comparison chart summarizing an experiment to evaluate the testing and characterization protocols described in FIGS. 6 and 7 in the context of 425 nm light for reducing viral loads of SARS-CoV-2 Beta in human tissue models. For the study, samples of the Tissue Model 2 of FIG. 8B were infected with SARS-CoV-2 Beta with multiplicity of infection (MOI) values of 0.1. Light treatments at 425 nm were applied according to either the FIG. 6 sequence for quaque die (QD) or once daily treatments, or the FIG. 7 sequence for bis in die (BID) or twice daily treatments. Light treatments were administered at 32 J/cm$^2$ daily doses and the x-axis in FIG. 9A represents a total or cumulative dose. For comparison, a control population was also provided that did not receive any light treatments (i.e., 0 J/cm$^2$). Data is presented as mean viral titer calculated in plaque-forming units per milliliter (PFU/mL)+/−SD (n=6). Statistical significance was determined with the Mann-Whitney ranked sum test and is indicated by ** (p≤0.01) in FIG. 9A. While the QD regimen reduced titers by >1 $\log_{10}$ at 72 hpi, the BID regimen reduced titers by >4 $\log_{10}$ at 72 hpi. Importantly, the SARS-CoV-2 titers in BID-treated tissues decreased from 24 hpi to 72 hpi, indicating the inhibition of the SARS-CoV-2 Beta replication with the twice daily regimen. In this regard, these results demonstrate that twice daily light treatments with a dosing regimen of 32 J/cm$^2$ for 425 nm light may be sufficient to inhibit SARS-CoV-2 Beta in well-differentiated airway tissue models.

Figure 9B:
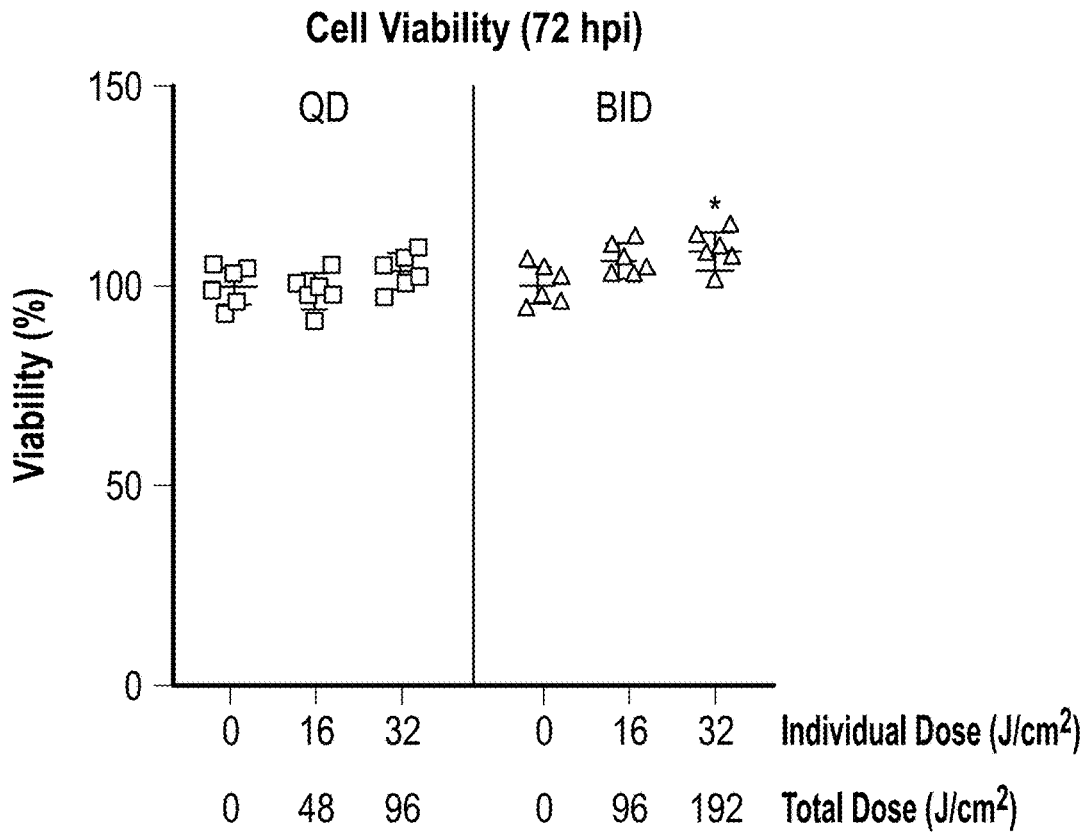
FIG. 9B is a comparison chart summarizing a companion cytotoxicity study for the chart of FIG. 9A where uninfected tissue models were treated in parallel with twice daily doses of light for three days.

FIG. 9B is a comparison chart summarizing a companion cytotoxicity study for the chart of FIG. 9A where uninfected tissue models were treated in parallel with twice daily doses of 32 J/cm$^2$ of 425 nm light for three days. Data is presented as PFU/mL+/−SD (n=6) and statistical significance was determined with the Mann-Whitney ranked sum test and is indicated by * (p≤0.05) in FIG. 9B. As illustrated, no light-induced cytotoxicity in time-matched, uninfected tissue models was observed after 3 days of repeat dosing. In this manner, FIGS. 9A and 9B represent one of many different types of studies that may be performed according to testing and characterization protocols of the present disclosure.

Figure 10A:
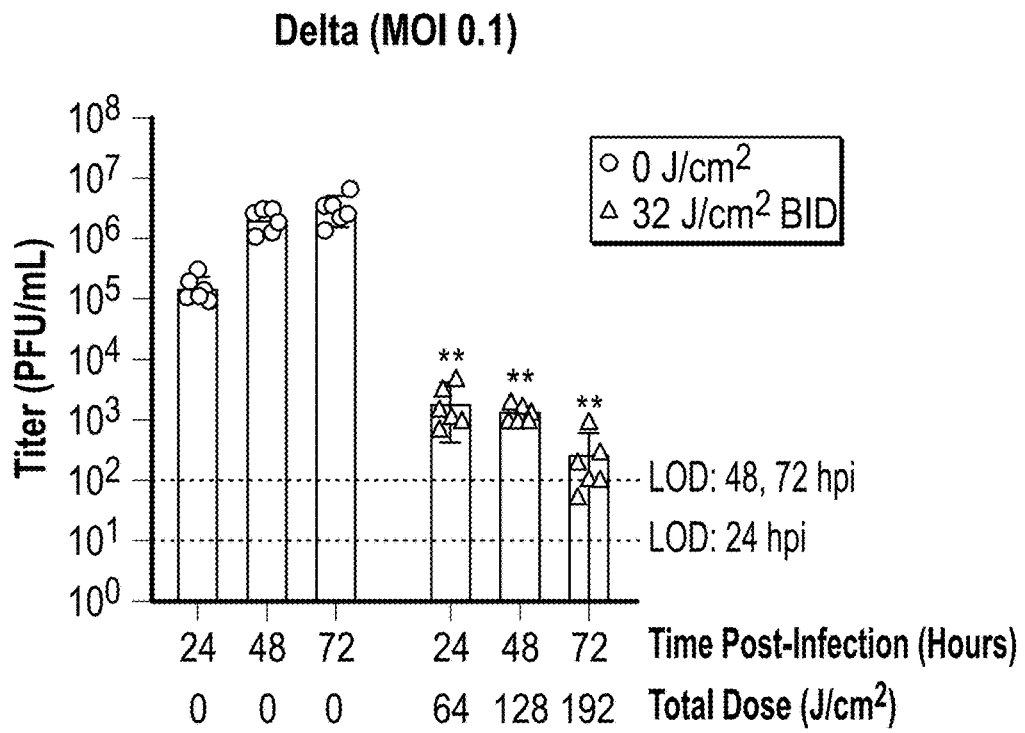
FIGS. 10A to 10C represent another study that was performed in a similar manner to the study summarized in FIG. 8A, but for SARS-CoV-2 Delta infections at multiple starting infectious titers in the same tissue models.
Figure 10B:
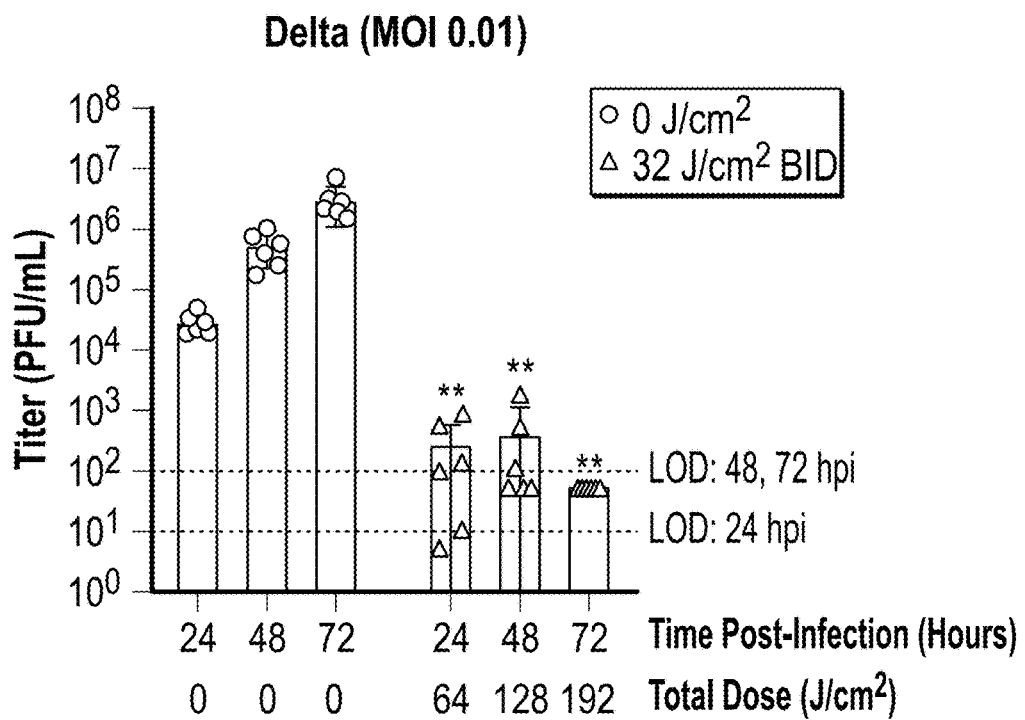
Figure 10C:
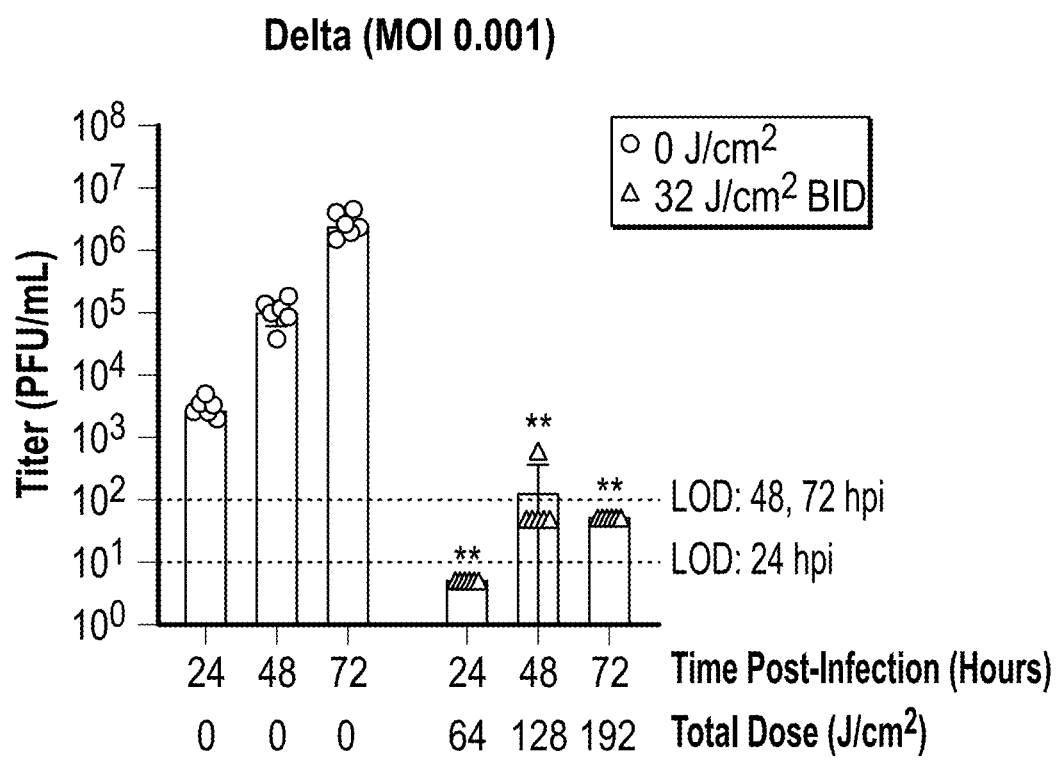
Figure 11:
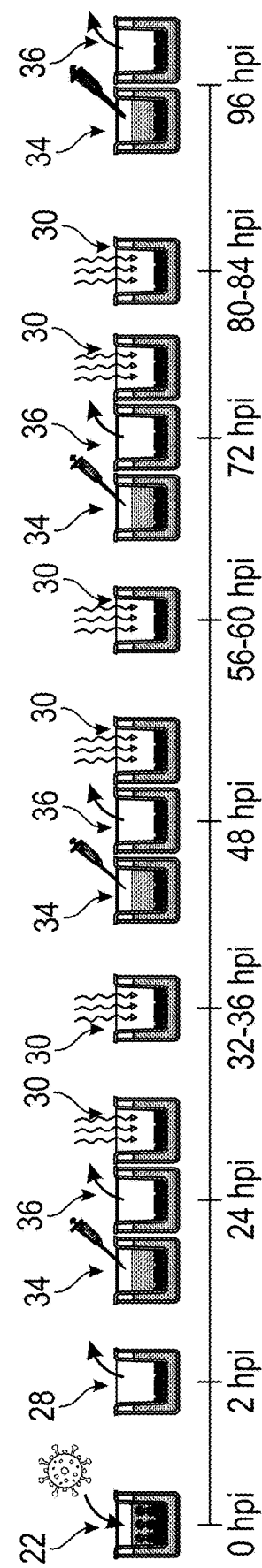
FIG. 11 is a process flow for testing and characterization of phototherapeutic light treatments in primary human tissue models that is similar to FIG. 7 but where light treatments begin at one day post infection.

FIGS. 10A to 10C represent another study that was performed in a similar manner to the study summarized in FIG. 8A, but for SARS-CoV-2 Delta infections at multiple starting infectious titers (MOIs of 0.1, 0.01, and 0.001) in the same tissue models. For the study, BID or twice daily light treatments were administered for three days with 32 J/cm$^2$ of 425 nm light starting at 3 hpi according to FIG. 7. Apical rinses were collected daily and enumerated via plaque assay. Data presented are mean viral titer calculated in PFU/mL+/−SD (n=6). Statistical significance was determined with the Mann-Whitney ranked sum test and is indicated by ** (p≤0.01) in FIGS. 10A to 10C. Concordant with the SARS-CoV-2 Beta of FIG. 8A, 32 J/cm$^2$ twice daily doses reduced SARS-CoV-2 Delta (MOI=0.1) infectious titers by >4 $\log_{10}$ at 72 hpi and infectious SARS-CoV-2 Delta titers also declined from 24 hpi to 72 hpi as illustrated in FIG. 10A. At the lower MOIs of FIGS. 10B and 10C, 425 nm light dramatically reduced infectious SARS-CoV-2 Delta after 3 days of twice daily repeat dosing below limits of detection (LOD).

Figure 12A:
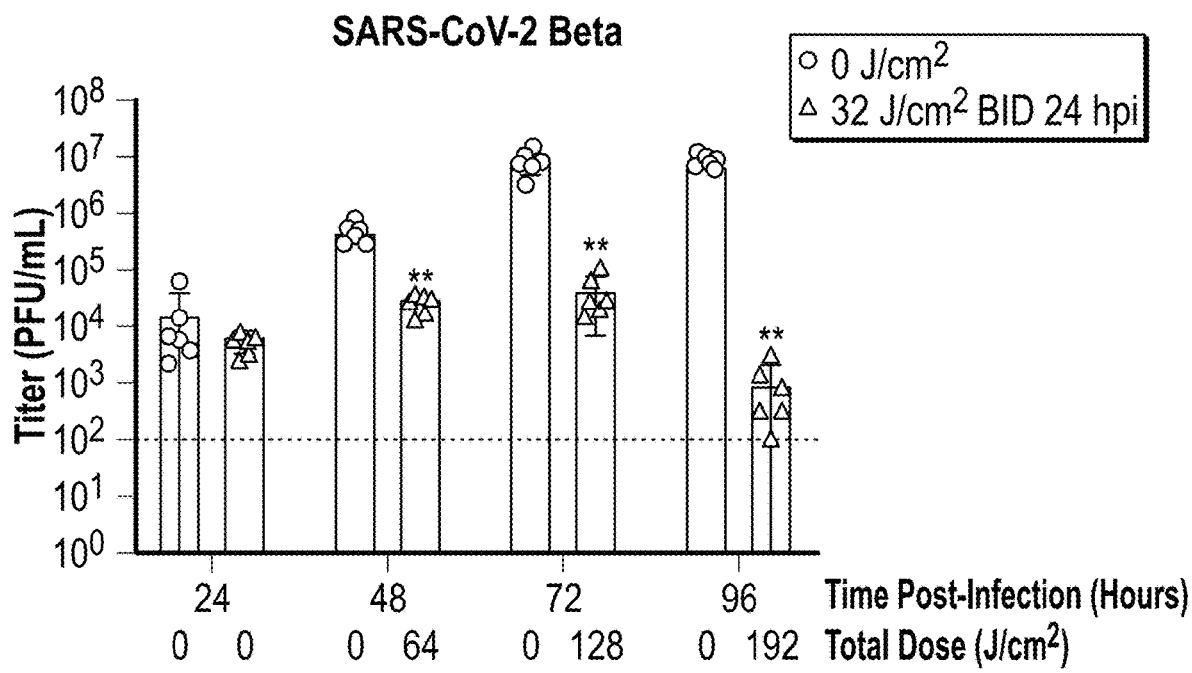
FIG. 12A represents data collected for the process flow of FIG. 1I for SARS-CoV-2 Beta in the primary human tissue model.
Figure 12B:
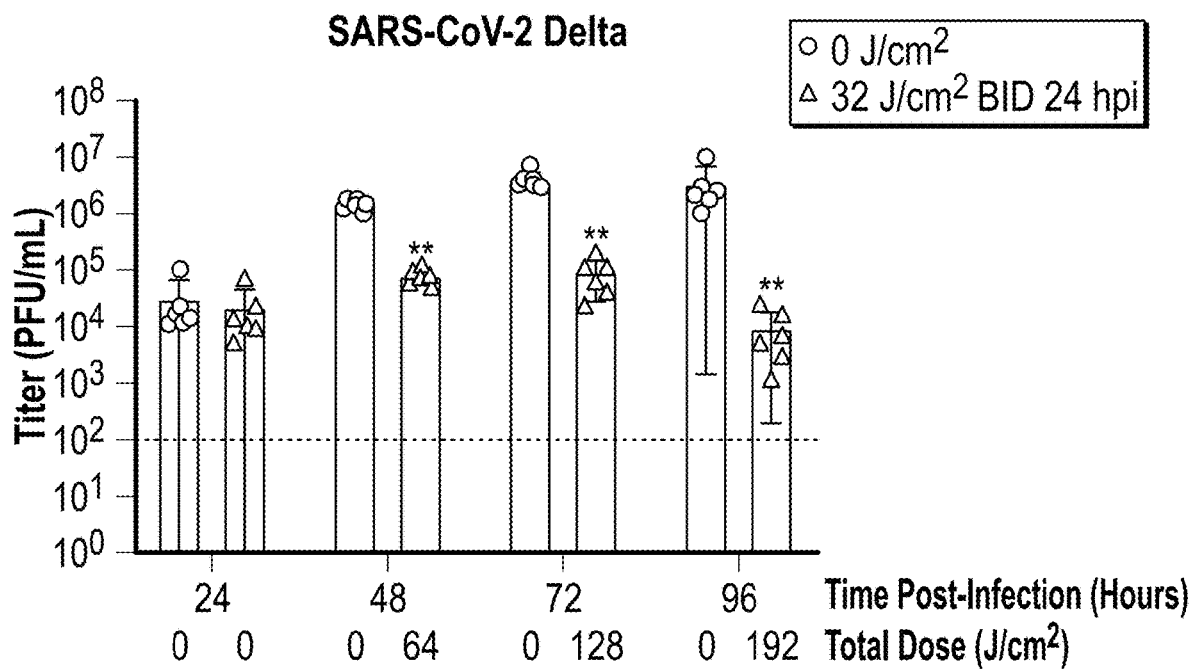
FIG. 12B represents data collected for the process flow of FIG. 1I for SARS-CoV-2 Delta in the primary human tissue model.

While FIGS. 9A to 10C demonstrate the therapeutic potential in reducing and/or inhibiting viral replication following administration of 425 nm light during early infection (3 hpi), testing and characterization protocols according to the present disclosure may be readily modified to evaluate light treatments for more established infections. In the regard, FIG. 1I is a process flow for testing and characterization of phototherapeutic light treatments in primary human tissue models that is similar to FIG. 7 but where twice daily light treatments begin at 24 hpi. Human tissue models were infected with SARS-CoV-2 Beta or SARS-CoV-2 Delta with MOI values of 0.001 and first therapeutic light doses were delayed to 24 hpi. FIG. 12A represents the data collected for SARS-CoV-2 Beta and FIG. 12B represents the data collected for SARS-CoV-2 Delta. For each variant, the doses of light were administered at 32 J/cm$^2$ for 425 nm light and apical rinses were collected daily and enumerated via plaque assay. Data is presented as PFU/mL+/−SD (n=6). Statistical significance was determined with the Mann-Whitney ranked sum test and is indicated by ** ($p \leq 0.01$). As shown in FIG. 12A, a delayed first dose reduced SARS-CoV-2 Beta infectious titers by >1 $\log_{10}$ at 48 hpi, by >2 $\log_{10}$ at 72 hpi, and by >3 $\log_{10}$ at 96 hpi. Similar results were seen with SARS-CoV-2 Delta as shown in FIG. 12B where infectious titers were significantly reduced by >1 $\log_{10}$ at 48 hpi, by >1 $\log_{10}$ at 72 hpi and by >2 $\log_{10}$ at 96 hpi. In this regard, these overall results provided in FIGS. 9A-10C and FIGS. 12A-12B suggest that 425 nm light therapy may inhibit SARS-CoV-2 replication at multiple stages during the viral replication cycles, in a variant-agnostic manner.

The rapid development and deployment of vaccines, improvements in standards of care, and increased focus on therapeutics have helped stem the spread of SARS-CoV-2 and the resulting worldwide economic burden. However, inequitable distribution of vaccines and therapeutics has contributed to pockets of uncontrolled viral spread and the emergence of novel variants, some of which are able to evade existing vaccines and therapeutics. Accordingly, novel therapeutics that will work broadly against variants, including those that have not yet emerged, without reformulation are needed. In this manner, the testing and characterization techniques for light-based treatments as disclosed herein may be utilized to rapidly develop protocols for SARS-CoV-2 as well as other infectious diseases.

The disease state at which the novel therapeutic would be most effective must also be considered. SARS-CoV-2 may infect the oral cavity, upper respiratory tract, and large airway prior to spread to the lower respiratory tract and the late-stage development of acute respiratory distress. Sustained replication in the oral and nasal cavities is likely a key contributor to the increased transmissibility of SARS-CoV-2 compared to other coronaviruses. For these reasons, a targeted approach for acute SARS-CoV-2 infection of the upper airway epithelia to halt progression via the oral-lung transmission axis is an attractive aim. A therapeutic that works during the early stages of infection is not only essential to reduce disease burden in the treated individual, but also to limit person-to-person transmission and decrease the potential for additional variants to emerge. As described herein, phototherapeutic light treatments and corresponding treatment protocols for light may not only inactivate all SARS-COV-2 variants of concern in cell-free suspensions, but targeted energy densities may inhibit SARS-CoV-2 infections at multiple stages of infection in tissue models of human airway epithelia. In this regard, targeted doses of light (e.g., 425 nm) could anchor treatment therapies without damage to host tissue.

While the above discussion is provided in the context of SARS-CoV-2, the principles described herein are applicable in the development of light-based treatments for many different types of infectious diseases and/or for inducing a variety of biological effects in human tissue models. As used herein, biological effects may comprise at least one of inactivating microorganisms including pathogens, inhibiting replication of microorganisms including pathogens, upregulating a local immune response, stimulating enzymatic generation of nitric oxide to increase endogenous stores of nitric oxide, releasing nitric oxide from endogenous stores of nitric oxide, and inducing an anti-inflammatory effect The principles described herein may be applied to rapidly test and characterize the effectiveness of different wavelengths of light in a dose-dependent manner for such biological effects in human tissue models. In this regard, light-based treatment protocols may be rapidly developed and refined according to principles of the present disclosure in a preclinical environment. Additionally, such light-based treatments may be administered in an on/off approach and at set time intervals, rather than small molecule drug approaches that may be left in basolateral media for consistent application throughout testing.

Figure 13:
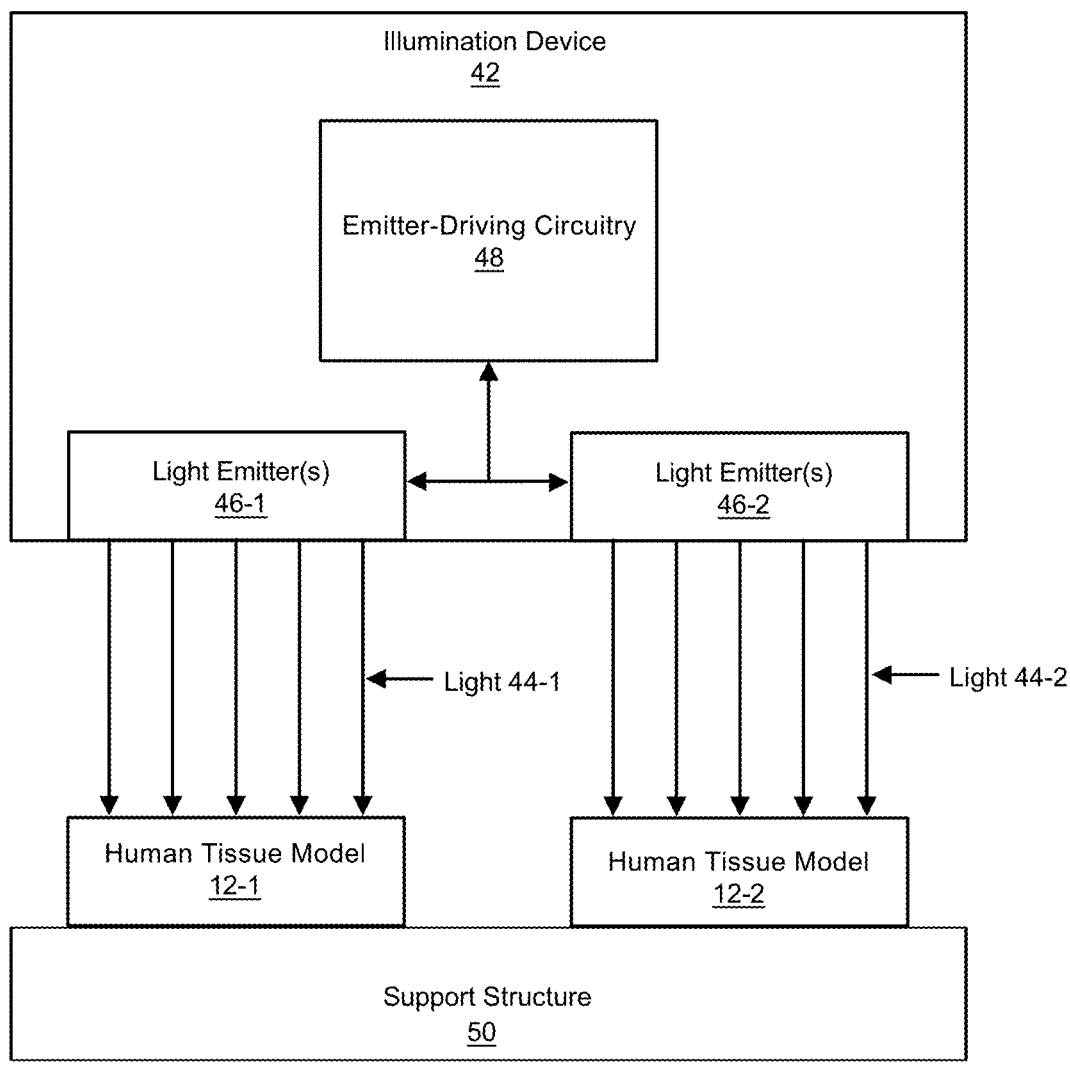
FIG. 13 is an illustration of an exemplary system that is configured to implement various light-based treatments on one or more human tissue models according to aspects of the present disclosure.

FIG. 13 is an illustration of an exemplary system 40 that is configured to implement various light-based treatments on one or more human tissue models 12-1, 12-2 according to aspects of the present disclosure. Such light-based testing may advantageously be implemented to determine an efficacy of light for inducing one or more biological effects in the human tissue models 12-1, 12-2. The system 40 may include an illumination device 42 for delivering light 44-1, 44-2 to the one or more human tissue models 12-1, 12-2 The illumination device 42 may include one or more light emitters 46-1, 46-2, such as LEDs, that are operable to emit the light 44-1, 44-2. The light emitters 46-1, 46-2 may be positioned so that one or more portions of the light 44-1, 44-2 may impinge the corresponding human tissue models 12-1, 12-2 with an angle of incidence of 90 degrees with a tolerance of plus or minus 10 degrees, although other angles of incidence may also be implemented. The illumination device 42 may further include emitter-driving circuitry 48 that is operable to control output of the light emitters 46-1, 46-2.

In certain embodiments, the light emitters 46-1, 46-2 may be configured to emit different wavelengths of light and/or different doses of light depending on the nature of a particular experiment. For example, in the exemplary data provided above for FIGS. 9A to 10C, the light emitters 46-1, 46-2 may be configured to emit a same peak wavelength such as 425 nm, but with different light doses to different ones of the human tissue models 12-1, 12-2. In other examples, the light emitters 46-1, 46-2 may be configured to emit different peak wavelengths of light to different ones of the human tissue models 12-1, 12-2, at same light doses or at different light doses depending on the nature of the experiment. In this manner, the system 40 may be capable of simultaneously testing multiple human tissue models 12-1, 12-2 with different light-based treatments. In the case of evaluating a biological response relative to microorganisms, pathogens, and/or viruses, each of the human tissue models 12-1, 12-2 may be exposed to a particular microorganism, pathogen, and/or virus at a same initial time, followed by concurrent light-based treatments. In certain embodiments, each of the human tissue models 12-1, 12-2 may be positioned on a support structure 50 with a spacing that corresponds with a spacing of the different light emitters 46-1, 46-2 of the illumination device 42. While FIG. 13 is illustrated with two light emitters 12-1, 12-2 for illustrative purposes, the principles described are applicable to any number of light emitters, including a single light emitter, and a plurality of light emitters that form an array for testing a corresponding array of human tissue models.

Figure 14:
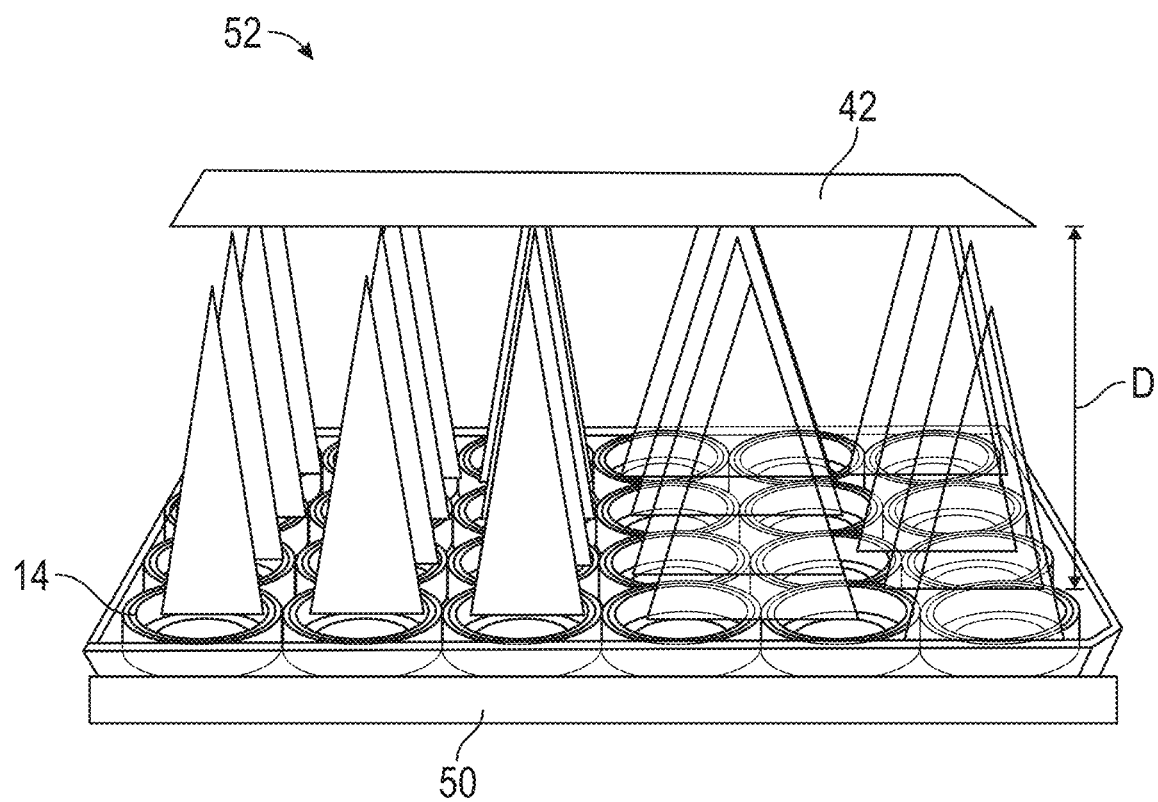
FIG. 14 illustrates a perspective view of a testing set-up for a system that is similar to the system of FIG. 13 where the illumination device is provided with an array of light emitters.

FIG. 14 illustrates a perspective view of a testing set-up for a system 52 that is similar to the system 40 of FIG. 13 where the illumination device 42 is provided with an array of light emitters. For experiments as described above for FIGS. 5 to 12B, the support structure 50 may be configured to support a plurality of the containers 14, each of which including a human tissue model. The illumination device 42 may include one or more LED arrays arranged to emit light separately to each of the containers 14 for the purposes of determining an efficacy of the light in inducing a biological effect in the human tissue models. In addition to the design of the LED arrays of the illumination device 42, including the emission spectrums, other important conditions that may be subject to experimentation include a distance D of the LED arrays of the illumination device 42 from the human tissue models in the containers 14, an illumination power of the LED arrays, and administered doses. In this manner, the system 52 may be well suited for performing the testing and characterization sequences described above for FIGS. 5 to 12B.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. A method comprising:
   administering a first dose of light to a surface of a human tissue model to induce a biological effect in the human tissue model after a virus stock in a first diluent is exposed to the surface of the human tissue model and after the virus stock and the first diluent have been removed from the human tissue model; and
   determining an efficacy of the first dose of light in the human tissue model based on the biological effect that is induced in the human tissue model by correlating a first viral load in the human tissue model by quantifying a viral load in a first apical wash of the human tissue model, wherein the first apical wash comprises a second diluent that is a same solution as the first diluent.

2. The method of claim 1, wherein the biological effect comprises at least one of inactivating microorganisms, inhibiting replication of microorganisms, upregulating a local immune response, stimulating enzymatic generation of nitric oxide to increase endogenous stores of nitric oxide, releasing nitric oxide from endogenous stores of nitric oxide, and inducing an anti-inflammatory effect.

3. The method of claim 1, wherein:
   the human tissue model is exposed to the virus stock for a first time period; and
   the first dose of light is administered at an end of a second time period from when the virus stock is exposed to the human tissue model.

4. The method of 3, wherein the end of the second time period is in a range from 30 minutes to 90 minutes after an end of the first time period.

5. The method of claim 3, wherein the first apical wash is completed at an end of a third time period from when the virus stock is exposed to the human tissue model.

6. The method of claim 1, further comprising administering a second dose of light to the surface of the human tissue model after the first apical wash.

7. The method of claim 6, further comprising:
   correlating a second viral load in the human tissue model at an end of a fourth time period after the virus stock is exposed to the human tissue model by quantifying a viral load in a second apical wash of the human tissue model, wherein the second apical wash comprises a third diluent that is a same solution as the first diluent.

8. The method of claim 1, wherein the human tissue model comprises a human airway epithelia model.

9. The method of claim 8, wherein the virus stock comprises at least one of influenza and coronaviridae that is applied to the human airway epithelia model.

10. The method of claim 9, wherein the first dose of light comprises a peak wavelength in a range from 400 nanometers (nm) to 450 nm that is irradiated on the surface of the human tissue model after the at least one of the influenza and the coronaviridae is removed.

11. The method of claim 1, wherein the first diluent and the second diluent comprise minimum essential medium with a fetal bovine serum additive.

12. A method comprising:
   administering a plurality of light doses to a surface of a human tissue model to induce a biological effect in the human tissue model after a virus stock in a first diluent is exposed to the surface of the human tissue model and after the virus stock and the first diluent have been removed from the human tissue model; and
   determining an efficacy of the plurality of light doses in the human tissue model based on the biological effect that is induced in the human tissue model by correlating a viral load in the human tissue model at a plurality of time intervals by quantifying an amount of a viral load in a plurality of apical washes, wherein each apical wash of the plurality of apical washes is followed by administering at least one light dose of the plurality of light doses up until a last apical wash of the plurality of apical washes.

13. The method of claim 12, wherein the biological effect comprises at least one of inactivating microorganisms, inhibiting replication of microorganisms, upregulating a local immune response, stimulating enzymatic generation of nitric oxide to increase endogenous stores of nitric oxide, releasing nitric oxide from endogenous stores of nitric oxide, and inducing an anti-inflammatory effect.

14. The method of claim 12, wherein at least two light doses of the plurality of light doses are administered to the surface of the human tissue model before a first apical wash of the plurality of apical washes.

15. The method of claim 14, wherein at least two additional light doses of the plurality of light doses are administered to the surface of the human tissue model after the first apical wash of the plurality of apical washes and before a second apical wash of the plurality of apical washes.

16. The method of claim 12, wherein each apical wash of the plurality of apical washes is performed at successive 24-hour intervals after the virus stock is exposed to the human tissue model.

17. The method of claim 12, wherein the plurality of apical washes comprise a solution that is the same as the first diluent.

18. The method of claim 12, wherein a first apical wash of the plurality of apical washes is performed before any light does of the plurality of light doses are administered.

19. The method of claim 12, wherein the human tissue model comprises a human airway epithelia model.

20. The method of claim 19, wherein the virus stock comprises at least one of influenza and coronaviridae that is applied to the human airway epithelia model.

21. The method of claim 20, wherein a first dose of light comprises a peak wavelength in a range from 400 nanometers (nm) to 450 nm that is irradiated on the surface of the human airway epithelia model after the at least one of the influenza and the coronaviridae is removed.

* * * * *